United States Patent
Birol et al.

(10) Patent No.: US 12,280,090 B2
(45) Date of Patent: Apr. 22, 2025

(54) ANTIMICROBIAL PEPTIDES

(71) Applicants: PROVINCIAL HEALTH SERVICES AUTHORITY, Vancouver (CA); UVIC INDUSTRY PARTNERSHIPS INC., Victoria (CA)

(72) Inventors: Inanc Birol, Vancouver (CA); Caren C. Helbing, Victoria (CA); Stewart Austin Hammond, Saskatoon (CA)

(*) Notice: Subject to any disclaimer, the term of this patent is extended or adjusted under 35 U.S.C. 154(b) by 817 days.

(21) Appl. No.: 17/312,806

(22) PCT Filed: Dec. 10, 2019

(86) PCT No.: PCT/CA2019/051778
§ 371 (c)(1),
(2) Date: Jun. 10, 2021

(87) PCT Pub. No.: WO2020/118427
PCT Pub. Date: Jun. 18, 2020

(65) Prior Publication Data
US 2022/0125873 A1 Apr. 28, 2022

Related U.S. Application Data

(60) Provisional application No. 62/778,450, filed on Dec. 12, 2018.

(51) Int. Cl.
| | |
|---|---|
| *A61K 38/17* | (2006.01) |
| *A61P 31/04* | (2006.01) |
| *G01N 33/50* | (2006.01) |
| *G01N 33/569* | (2006.01) |
| *G16B 15/30* | (2019.01) |

(52) U.S. Cl.
CPC .......... *A61K 38/1703* (2013.01); *A61P 31/04* (2018.01); *G01N 33/5011* (2013.01); *G01N 33/56911* (2013.01); *G16B 15/30* (2019.02); *G01N 2500/04* (2013.01)

(58) Field of Classification Search
CPC .. A61K 38/1703; A61K 38/00; C07K 14/463; A61P 31/04; G16B 15/30; G01N 33/5011; G01N 33/56911; G01N 2500/04
See application file for complete search history.

(56) References Cited

U.S. PATENT DOCUMENTS

| | | | |
|---|---|---|---|
| 7,862,826 B2 | 1/2011 | Murphy et al. | |
| 2007/0207209 A1* | 9/2007 | Murphy | A61K 9/06 514/17.7 |
| 2014/0142028 A1* | 5/2014 | Eckert | A61P 33/02 514/2.7 |

FOREIGN PATENT DOCUMENTS

| | | |
|---|---|---|
| WO | 2013039857 A1 | 3/2013 |
| WO | 2018209127 A1 | 11/2018 |

OTHER PUBLICATIONS

GenBank: ABB89058.1, ranatuerin 2CHb precursor, partial [Lithobates chiricahuensis], 2007 (Year: 2007).*
Epand et al., "Liposomes as Models for Antimicrobial Peptides", Methods in Enzymology, 2003, pp. 124-133 (Year: 2003).*
Pierce, "Protein stability and storage", Technical Resource, 3 pages, 2005 (Year: 2005).*
Kumar et al., "Antimicrobial Peptides: Diversity, Mechanism of Action and Strategies to Improve the Activity and Biocompatibility In Vivo", Biomolecules, 2018, 24 pages (Year: 2018).*
Paulstrin-2AM protein, GenBank: AEP84609.1 (Year: 2016).*
Hainanensisin-D1_2 antimicrobial peptide GenBank: ADV36156.1 (Year: 2011).*
Aittomaki et al., "Proprotein Convertase Furin1 Expression in the *Drosophila* Fat Body is Essential for a Normal Antimicrobial Peptide Response and Bacterial Host Defense," FASEB Journal, Nov. 2017, vol. 31 (11), pp. 4770-4782.
Andersson et al., "Mechanisms and Consequences of Bacterial Resistance to Antimicrobial Peptides," Drug Resistance Updates, May 2016, vol. 26, pp. 43-57.
"Antimicrobial Resistance: Global Report on Surveillance," World Health Organization, 2014, 265 pages.
Bahar et al., "Antimicrobial Peptides," Pharmaceuticals, 2013, vol. 6 (12), pp. 1543-1575.
Batista et al., "A Novel Heterodimeric Antimicrobial Peptide From the Tree-Frog Phyllomedusa Distincta, " FEBS Letters, 2001, vol. 494, pp. 85-89.
Beckloff et al., "Computational Analysis Suggests Beta-Defensins are Processed to Mature Peptides by Signal Peptidase," Protein and Peptide Letters, 2008, vol. 15 (5), pp. 536-540.
Brandenburg et al., "Peptides With Dual Mode of Action: Killing Bacteria and Preventing Endotoxin-Induced Sepsis," Biochimica et Biophysica Acta (BBA)—Biomembranes, May 2016, vol. 1858 (5), pp. 971-979.
Calhoun et al., "Role of Antimicrobial Peptides in Amphibian Defense Against Trematode Infection," EcoHealth, 2016, vol. 13 (2), pp. 383-391.
Cameron et al., "Defining the Interaction of the Treponema pallidum Adhesin Tp0751 with Laminin," Infection and Immunity, Nov. 2005, vol. 73 (11), pp. 7485-7494.

(Continued)

*Primary Examiner* — Li N Komatsu
(74) *Attorney, Agent, or Firm* — Borden Ladner Gervais LLP; Kathleen E. Marsman

(57) ABSTRACT

Antimicrobial peptides (AMPs), small compounds that often exhibit broad spectrum antimicrobial activity, are garnering interest as potential therapeutics against antibiotic-resistant bacterial pathogens. Development of new AMPs is arduous due to the practical limitations of classical protein-based discovery approaches. A high throughput bioinformatics approach is described which is able to confirm identification of known AMPs from the North American bullfrog (*Rana* (*Lithobates*) *catesbeiana*) genome, and a bioinformatics approach is used to develop new AMPs. The described AMPs exhibit antimicrobial activity against *Mycobacterium smegmatis* via microtitre broth dilution assays, indicating broader efficacy.

13 Claims, 9 Drawing Sheets

Specification includes a Sequence Listing.

(56) References Cited

OTHER PUBLICATIONS

Clark et al., "Ranalexin. A Novel Antimicrobial Peptide From Bullfrog (Rana catesbeiana) Skin, Structurally Related to the Bacterial Antibiotic, Polymyxin," Journal of Biological Chemistry, 1994, vol. 269 (14), pp. 10849-10855.
Cockerill et al., Methods for Dilution Antimicrobial Susceptibility Tests for Bacteria That Grow Aerobically: Approved Standard, Clinical and Laboratory Standards Institute—Tenth Edition, 2015, CLSI Document M07-A10, 110 pages.
Conlon et al., "Antimicrobial Peptides From the Skins of North American Frogs," Biochimica et Biophysica Acta, Aug. 2009, vol. 1788 (8), pp. 1556-1563.
Conlon et al., "Evaluation of the Skin Peptide Defenses of the Oregon Spotted Frog Rana Pretiosa Against Infection by the Chytrid Fungus Batrachochytrium Dendrobatidis," Journal of Chemical Ecology, 2013, vol. 39 (6), pp. 797-805.
Conlon et al., "Host Defense Peptides From Lithobates Forreri, Hylarana Luctuosa, and Hylarana Signata (Ranidae): Phylogenetic Relationships Inferred From Primary Structures of Ranatuerin-2 and Brevinin-2 Peptides," Comparative biochemistry and physiology. Part D Genomics Proteomics, 2014, vol. 9, pp. 49-57.
Conlon et al., "Host-Defense Peptides With Therapeutic Potential From Skin Secretions of Frogs From the Family Pipidae," Pharmaceuticals (Basel), Jan. 2014, vol. 7 (1), pp. 58-77.
Durr et al., "LL-37, The Only Human Member of the Cathelicidin Family of Antimicrobial Peptides," Biochimica et Biophysica Acta, 2006, vol. 1758 (9), pp. 1408-1425.
Finn et al., "The Pfam Protein Families Database: Towards a More Sustainable Future," Nucleic Acids Research, Jan. 2016, vol. 44 (D1), pp. D279-D285.
Ge et al., "Balteatide: A Novel Antimicrobial Decapeptide From the Skin Secretion of the Purple-Sided Leaf Frog, Phyllomedusa Baltea," The Scientific World Journal, 2014, pp. 1-9.
"Global Action Plan on Antimicrobial Resistance," World Health Organization, 2015, 28 pages.
Goraya et al., "Ranatuerins: Antimicrobial Peptides Isolated from the Skin of the American Bullfrog,Rana catesbeiana," Biochemical and Biophysical Research Communications, 1998, vol. 250 (3), pp. 589-592.
Hammond et al., "The North American Bullfrog Draft Genome Provides Insight Into Hormonal Regulation of Long Noncoding RNA," Nature Communications, 2017, vol. 8 (1): 1433, 8 pages.
Haney et al., "Mechanism of Action of Puroindoline Derived Tryptophan-Rich Antimicrobial Peptides," Biochimica et Biophysica Acta, Aug. 2013, vol. 1828 (8), pp. 1802-1813.
Holden et al., "Development of Antimicrobial Peptide Defenses of Southern Leopard Frogs, Rana Sphenocephala, Against the Pathogenic Chytrid Fungus, Batrachochytrium Dendrobatidis," Developmental and Comparative Immunology, Jan. 2015, vol. 48 (1), pp. 65-75.
International Patent Application No. PCT/CA2019/051778, International Search Report and Written Opinion dated Apr. 6, 2020.
International Patent Application No. PCT/CA2019/051778, International Preliminary Report on Patentability dated Jun. 3, 2021.
Jackman et al., "Transcriptomics Investigation of Thyroid Hormone Disruption in the Olfactory System of the Rana [lithobates] Catesbeiana Tadpole," Aquatic Toxicology, 2018, vol. 202, pp. 46-56.
Jantaruk et al., "Potential Role of an Antimicrobial Peptide, KLK in Inhibiting Lipopolysaccharide-Induced Macrophage Inflammation," PLoS One, Aug. 2017, vol. 12 (8) : e0183852, 17 pages.
Jones et al., "Interproscan 5: Genome-Scale Protein Function Classification," Bioinformatics, 2014, vol. 30 (9), pp. 1236-1240.
Joo et al., "Bacterial Strategies of Resistance to Antimicrobial Peptides," Philosophical Transactions of the Royal Society of London. Series B, Biological Cciences, May 2016, vol. 371 (1695), pp. 1-11.
Katzenback et al., "Regulation of the Rana Sylvatica Brevinin-1SY Antimicrobial Peptide During Development and in Dorsal and Ventral Skin in Response to Freezing, Anoxia and Dehydration," The Journal of Experimental Biology, 2014, vol. 217, pp. 1392-1401.
Kosciuczuk et al., "Cathelicidins: Family of Antimicrobial Peptides. A Review," Molecular Biology Reports, 2012, vol. 39 (12), pp. 10957-10970.
Krause A., "Isolation and Biochemical Characterization of LEAP-2, A Novel Blood Peptide Expressed in the Liver," Protein Science, 2003, vol. 12 (1), pp. 143-152.
Liang et al., "Molecular Cloning and Expression Analysis of Liver-Expressed Antimicrobial Peptide 1 (LEAP-1) and LEAP-2 Genes in the Blunt Snout Bream (Megalobrama Amblycephala)," Fish & Shellfish Immunology, 2013, vol. 35 (2), pp. 553-563.
Luca et al., "Esculentin(1-21), An Amphibian Skin Membrane-Active Peptide With Potent Activity on Both Planktonic and Biofilm Cells of the Bacterial Pathogen Pseudomonas Aeruginosa," Cellular and Molecular Life Sciences, 2013, vol. 70 (15), pp. 2773-2786.
Mistry et al., "Challenges in Homology Search: HMMER3 and Convergent Evolution of Coiled-Coil Regions," Nucleic Acids Research, vol. 41 (12), pp. e121-e121.
"Modified MIC Method for Cationic Antimicrobial Peptides," Hancock Labs, 1996, 4 pages. Available at: http:/cmdr.ubc.ca/bobh/method/modified-mic-method-for-cationic-antimicrobial-peptides/. (Accessed: Sep. 22, 2017).
Munita et al., "Mechanisms of Antibiotic Resistance," Virulence Mechanisms of Bacterial Pathogens, Fifth Edition, 2016, pp. 481-511.
Nathan et al., "Antibiotic Resistance—Problems, Progress, and Prospects," The New England Journal of Medicine, 2014, vol. 371, pp. 1761-1763.
Nguyen et al., "The Expanding Scope of Antimicrobial Peptide Structures and Their Modes of Action," Trends in Biotechnology, 2011, vol. 29 (9), pp. 464-472.
Ohnuma et al., "Developmental and Thyroid Hormone-Induced Expression of Preprotemporin Genes in the Skin of Japanese Mountain Brown Frog Rana Ornativentris," Annals of the New York Academy of Sciences, Apr. 2009, vol. 1163, pp. 494-496.
Otvos ., "Immunomodulatory Effects of Anti-Microbial Peptides," Acta Microbiologica et Immunologica Hungarica, 2016, vol. 63, pp. 257-277.
Reilly et al., "Expression of Magainin Antimicrobial Peptide Genes in the Developing Granular Glands of Xenopus Skin and Induction by Thyroid Hormone," Developmental Biology, 1994, vol. 162, pp. 123-133.
Robertson et al., "De Novo Assembly and Analysis of RNA-Seq Data," Nature Methods, Nov. 2010, vol. 7 (11), pp. 909-912.
Rollins-Smith., "Amphibian Immunity-Stress, Disease, and Climate Change," Developmental and Comparative Immunology, 2017, vol. 66, pp. 111-119.
Rollins-Smith., "The Role of Amphibian Antimicrobial Peptides in Protection of Amphibians From Pathogens Linked to Global Amphibian Declines," Biochimica et Biophysica Acta, 2009, vol. 1788 (8), pp. 1593-1599.
Schadich et al., "Skin Peptides of Different Life Stages of Ewing's Tree Frog," Journal of Experimental Zoology. Part A, Ecological Genetics and Physiology, 2009, vol. 313A, pp. 532-537.
Sievers et al., "Fast, Scalable Generation of High-Quality Protein Multiple Sequence Alignments Using Clustal Omega," Molecular Systems Biology, 2014, vol. 7, pp. 539-539.
Stotz et al., "Innate Immunity in Plants: The Role of Antimicrobial Peptides," In: Antimicrobial Peptides and Innate Immunity, Springer Basel, Hiemstra & Zaat (Eds.), 2013, vol. 2, pp. 29-51. DOI 10.1007/978-3-0348-0541-4.
Unubol et al., "Peptide Antibiotics Developed by Mimicking Natural Antimicrobial Peptides," Clinical Microbiology: Open Access, 2017, vol. 6 (4), 1000291.
Valore et al., "Posttranslational Processing of Hepcidin in Human Hepatocytes is Mediated by the Prohormone Convertase Furin," Blood Cells, Molecules & Diseases, 2008, vol. 40 (1), pp. 132-138.
Waghu et al., "CAMP R3 : A Database on Sequences, Structures and Signatures of Antimicrobial Peptides," Nucleic Acids Research, Jan. 2016, vol. 44, pp. D1094-D1097.

(56) References Cited

OTHER PUBLICATIONS

Wernersson., "Virtual Ribosome—A Comprehensive DNA Translation Tool With Support for Integration of Sequence Feature Annotation," Nucleic Acids Research, Jul. 2006, vol. 34, pp. W385-W388.

Woodhams et al., "Life History Linked to Immune Investment in Developing Amphibians," Conservation Physiology, Aug. 2016, vol. 4 (1), 15 pages.

Wu et al., "GMAP: GMAP: A Genomic Mapping and Alignment Program for mRNA and Est Sequences," Bioinformatics, May 2005, vol. 21 (9), pp. 1859-1875.

Zaiou et al., "Cathelicidins, Essential Gene-Encoded Mammalian Antibiotics," Journal of Molecular Medicine, 2002, vol. 80 (9), pp. 549-561.

Zhang et al., "Evolution, Expression, and Characterisation of Liver-Expressed Antimicrobial Peptide Genes in Ancient Chondrostean Sturgeons," Fish & Shellfish Immunology, Aug. 2018, vol. 79, pp. 363-369.

Chen et al., "Two Novel Families of Antimicrobial Peptides From Skin Secretions of the Chinese Torrent Frog, Amolops Jingdongensis," Biochimie, 2012, vol. 94(2), pp. 328-334.

European Patent Application No. 198974651, Partial Supplementary European Search Report dated Aug. 29, 2022.

Helbing et al., "Antimicrobial Peptides From Rana [lithobates] Catesbeiana: Gene Structure and Bioinformatic Identification of Novel Forms From Tadpoles," Scientific Reports, 2019, vol. 9(1), pp. 1-11.

Li C, et al., "AMPlify: Attentive Deep Learning Model for Discovery of Novel Antimicrobial Peptides Effective Against Who Priority Pathogens," BMC Genomics, 2022, vol. 23, pp. 1-15.

Robertson et al., "Expression Analysis and Identification of Antimicrobial Peptide Transcripts From Six North American Frog Species," Diseases of Aquatic Organisms, 2013, vol. 104(3), pp. 225-236.

European Patent Application No. 20190897465, Extended European Search Report dated Nov. 29, 2022.

Japanese Patent Application No. JP20210533350, Office Action dated Nov. 1, 2023—English Translation Available.

Japanese Patent Application No. 2021-533350, Office Action dated Mar. 27, 2024 (English Translation Available).

* cited by examiner

```
A AFR43665-Ranatuerin-2PRc    MFTMKKSLLLLFFFLGTISLSLCEEERDADDDQGEVVKKEVKRAFFTTVKNLVTNVAGTVIDKMKCKLTGQC  71
  Ranatuerin-2PRc(HP2)         MFTMKKSLLLLFFFLGTISLSLCEQERNADDDQGEVIEQKVKRAFLSTVKNTLTNVAGTMIDTFKCKITGVC  71
                               **********:***********:**:******:::*****:;****  ;*******;:******** *

B Ranatuerin-1                 MFTLKKSLLLLFFLGTITLSLCEQERGADEEEGNG--EKEIKR--SMLSVLKN------LGKVGLGFVACKINKQC--  66
  Ranatuerin-1(HP4)             -----MSSFCEITNVALTISLSSPRRGADEEEGNG--EKEIKR--SMLSVLKN------LGKVGLGFVACKINKQC--  61
  Ranatuerin-3RC(HP8)           -----------------MFPMSSPRRDADEVKE-------VKR--GFLDIIKN--LGKTFAGHMLDKIKCTIGTCPPSP 51
  Ranatuerin-3RC                MFTMKKSLLLLFFLGTISLSLCEPQRDADEVKE-------VKR--GFLDIIKN--LGKTFAGHMLDKIKCTIGTCPPSP 68
  Ranatuerin-4                  MFTLKKSLLLLFFLGTINLSLCEEERDAEEERRDNPDERDVEVEKRFLPF------IARLAAKVFPSIICSVTKKC--  70
  Ranatuerin-2PRc(HP2)          MFTMKKSLLLLFFFLGTISLSLCEQERNADDDQG-EVIEQKVKR--AFLSTVKN--TLTNVAGTMIDTFKCKITGVC-- 71
  Ranatuerin-2RC                MFTLKKSLLLLFFLGTITLSLCEQERGADEDNGGEMTEEEVKR--GLFLDTLKGAA-KDVAGKLLEGLKCKITGCKP- 74
                                  : :.. .*.*::                  ::   :

C ACR84069-Ranacyclin-Cc       MFTMKKSLLLLFFLGIISLSLCEQERDANDEEDGGEVTKEVVKRSLRGCWTKSFPPQPCLGKRLNMN  67
  ACR84059-Ranacyclin-Ca       MFTLKKSLLLLFFFGIISLSFCEQERDANDEEDGGEVTKEVVKRSLRGCWTKSYPPQPCLGKR     63
  Ranacyclin-Ca(HP3)           ---------VLLYLIITVSFP---RRDANDEDGGEVTKEVVKRSLSGCWTKSFPPRKPCLRNR     50
                                ::::  **::**     *    :;**************** ******;*  ;*** ;*

D ACR84056-Catesbeianin-1      ---------MFTMKKSEKERRERGKRMMRVMRRKTKVIWEKKDFIGLYSID 42
  Catesbeianin-1(HP6)          MRKRMTMRRMMKKKKSEKERRERGKRMMRVMRRKTKVIWEKKDFIGLYSID 51
                               *:. ********************************************

E ACR84085-Palustrin-Ca        MFTMKKSLLLLFFLGTISLSLCEQERDADGDEGEVEEVKRGFLDIIKDTGKEFAVKILNNLKCKLAGGCPP 71
  Palustrin-Ca(HP9)            ------------------MITVSSPRRDADGDEGEVEEVKRGFLDIIKDTGKEFAVKILNNLKCKLAGGCPP 54
                               :::..  .**********************************************
```

(SEQ ID NO:15 to SEQ ID NO:30, respectively)

FIG. 1

A
```
AEI69698        MGLSATLWFLMGVAAGSMASPLLQWSEDDISVMALYSTDYYNKVSGEDVLYGLQENNTEY   60
Cathelicidin-AL MGLSATFWFLMGLAASSMASPLLQWSEDDAAVMALYSADHYNKVSGEDVLYGLLENDTEY   60
                ******:*****.**.*************:*****.*:************ **:***

AEI69698        ITDEKSRFHQLSFPIQKTVCQKSDN-ALTDDCAFKEGGVVKSCTSYFFEEDDRDIIVVTC  119
Cathelicidin-AL ITDEKSRFHQLSFPIQETVCQKSDNNAPTDDCAFKEGGVVKSCTSYFFEEDDRDIVVVNC  120
                ****************:******** * *******************************:**.*

AEI69698        QSQDGHREHSRVRRSRRGRGGGRRGGSGGRGGRGGGGRSGAGSSIAGVGSRGGG--GGRHYA  179
Cathelicidin-AL QSQDSHREHSRVRRSRSGRGGGGRGG-GGRGGSRGGSRSGSRSSIAGGGSRGGSRGGGTRYA  181
                ****.*********** *** ***.***** **.***. ***** *****. ** :**

(SEQ ID NO:31)
(SEQ ID NO:32)
```

B
```
XP_018418722    MIPQLRKWMAIFVMCIVLIHQLEGAPMNSNDGSKTALRLRRMTPFWRGLSLRPVGASCRD   60
LEAP2           MTPQLRKWTAIFVICIVLIHQLEGAPMSNTAGSKTLLRLRRMTPFWRGLSLRPVGASCRD   60
                * ****** ***:*************..  **** *** **********************

XP_018418722    DTECLTRLCRNQRCSLKTFAD   81     (SEQ ID NO:33)
LEAP2           DTECLTRLCRKERCSLKTFAD   81     (SEQ ID NO:34)
                **********:.:********
```

FIG. 4

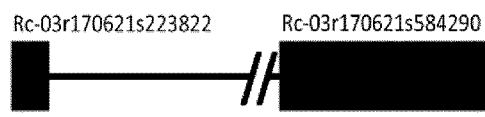
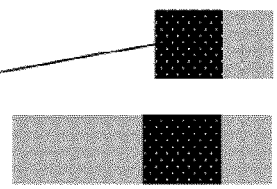
FIG. 6

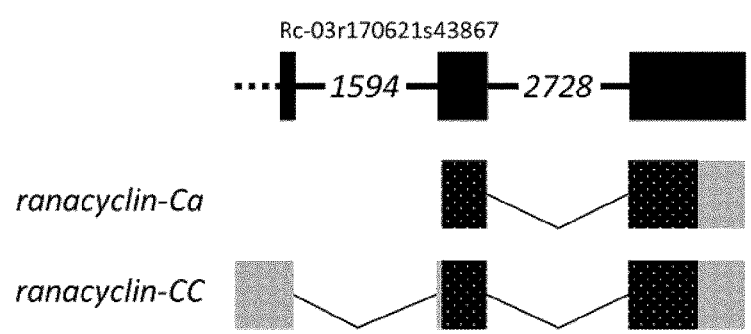
FIG. 8

ANTIMICROBIAL PEPTIDES

CROSS REFERENCE TO RELATED APPLICATIONS

This application is the U.S. National Phase of International Patent Application No. PCT/CA2019/051778 filed Dec. 10, 2019 entitled "ANTIMICROBIAL PEPTIDES", and claims the benefit of priority of U.S. Provisional Patent Application No. 62/778,450 filed Dec. 12, 2018, the subject matter of which is incorporated by reference herein in its entirety.

STATEMENT REGARDING FEDERALLY SPONSORED RESEARCH OR DEVELOPMENT

This invention was made in part with United States government support under Grant No. R01 HG007182, awarded by the National Institutes of Health. The United States government has certain rights in the invention.

FIELD

The present disclosure relates generally to antimicrobial peptides for the treatment or mitigation of disease.

BACKGROUND

There is a need for peptides and pharmaceutical compositions thereof which are useful as therapies for microbial infections or as chemopreventative agents to slow or arrest the progression of microbial infections.

Use of antibiotics in livestock may have direct and indirect impact on medical use in addressing human disease. The ubiquitous use of antibiotics in all industries has contributed to the emergence of superbugs which have become resistant to the most common antibiotics. Some strains illustrate multi-drug resistance, which is a global concern. Although the search for new antibiotic approaches continues in earnest to address challenges in both human and animal health.

Consumers have concerns about the use of prophylactic antibiotics due to the potential environmental impact, increasing drug resistance, and the possible consumption of antibiotic lace meat or dairy products. Restrictions on prophylactic antibiotic use in livestock that have been implemented to address these concerns, but have downstream consequences such as increased rates of animal infections, leading to productivity loss due to the increase disease burden. Sick animals that are then treated with antibiotics will continue to contribute to potential drug resistance. Poultry and swine raised in close quarters are particularly susceptible to the rapid spread of disease. Different approaches to reducing infections disease in livestock animals are under development, including investigation of new antibiotic approaches, and development of vaccines. While small molecule drugs have conventionally been used, antimicrobial peptide and polypeptide therapeutic approaches are also under consideration.

It is, therefore, desirable to find new antimicrobial approaches to reduce the onset and spread of disease in humans and animals.

SUMMARY

Peptides and/or amino acid sequences with antimicrobial properties are described herein. A bioinformatics approach, starting with sequences exhibiting effect, and making strategic modifications thereto, has led to the discovery of antimicrobial peptides. In a bioinformatics approach, sufficient similarity among sequences can be maintained so as to permit functional equivalency. Sequences similar to isolated sequences from which a consensus is derived are also described. Such similar sequences contain conserved amino acid substitutions and a limited number of non-conserved modifications.

It is an object of the present disclosure to provide antimicrobial peptides, which may obviate or mitigate at least one disadvantage of previous antimicrobial approaches.

There is described herein an antimicrobial peptide comprising: an amino acid sequence according to any one of SEQ ID NO:1 to SEQ ID NO:166, or a fragment or variant thereof, having at least 65% amino acid sequence identity to any one of SEQ ID NO:1 to SEQ ID NO:166.

Further, there is described herein a composition comprising the described antimicrobial peptide together with a suitable excipient.

The composition comprising the described antimicrobial peptide may be a composition for use in in treatment or prevention of a disease or condition, such as infectious disease.

A use for the antimicrobial peptide is provided, for treatment or prevention of a disease or condition in a subject in need thereof. Further, the use of the antimicrobial peptide for preparation of a medicament for treatment or prevention of a disease or condition in a subject in need thereof is also described herein. Additionally, a method of treating or preventing a disease or condition is described, comprising administering to a subject in need thereof an effective amount of the antimicrobial peptide or composition thereof. The disease may be, for example, an infectious disease. The subject may be a human or an animal, such as a livestock animal or a companion animal.

A lipid vesicle comprising the antimicrobial peptide is described. A nucleic acid molecule encoding the antimicrobial peptide is also provided, as is a vector comprising such a nucleic acid molecule.

A method of identifying a target molecule associated with an infectious agent is described, in which the target molecule binds to the antimicrobial peptide. The method comprises the step of screening a library of candidate target molecules associated with the infectious agent, for a molecule that binds to the antimicrobial peptide. A kit for conducting such a method for identifying a target molecule associated with an infectious agent is also described, in which the kit comprises the antimicrobial peptide described herein together with instructions.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

FIG. 1 shows Clustal omega alignments of putative AMP precursor sequences with their closest known AMP matches. Panel A compares *Pseudacris regilla* Ranatuerin-2PRc (SEQ ID NO:15) with the *R. catesbeiana* HP2 (SEQ ID NO:16). Panel B aligns seven Ranatuerin precursor sequences (SEQ ID NO:17 to SEQ ID NO:23). Panel C aligns three Ranacyclin precursor sequences from *R. cates-* beiana (SEQ ID NO:24 to SEQ ID NO:26). Panel D compares Catesbeianin-1 precursor sequences from *R. catesbeiana* (SEQ ID NO:27 and SEQ ID NO:28). Panel E aligns Palustrin-Ca precursor sequences from *R. catesbeiana* (SEQ ID NO:29 and SEQ ID NO:30).

Figure 2:
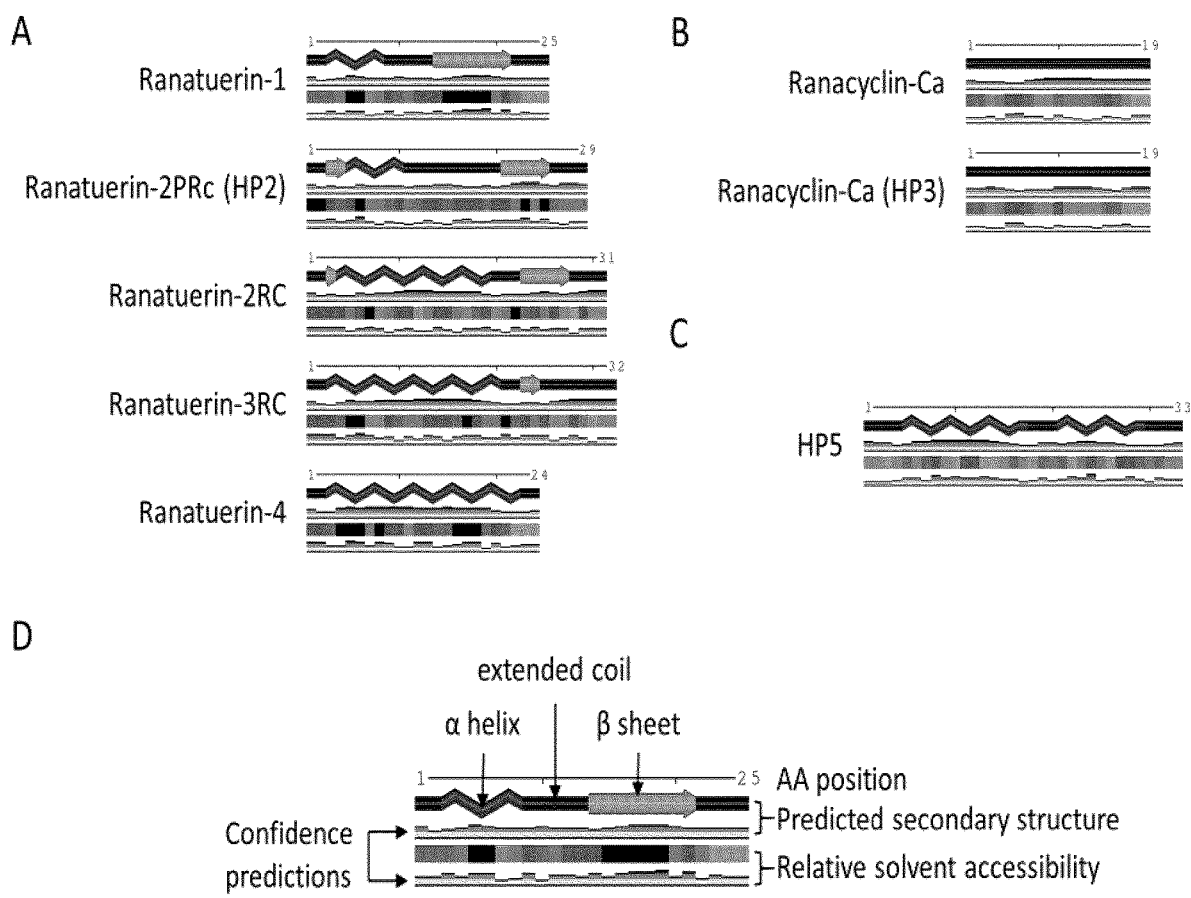

FIG. 2 illustrates a SABLE secondary structure prediction comparisons between the derived mature peptides of Panel A—HP2; Panel B—HP3; and Panel C—HP5 versus known mature AMP sequences. Panel D provides a legend for the SABLE predictions with amino acid (AA) position indicated at the top, the predicted secondary structure in the middle and the relative solvent accessibility (RSA) at the bottom.

Figure 3:
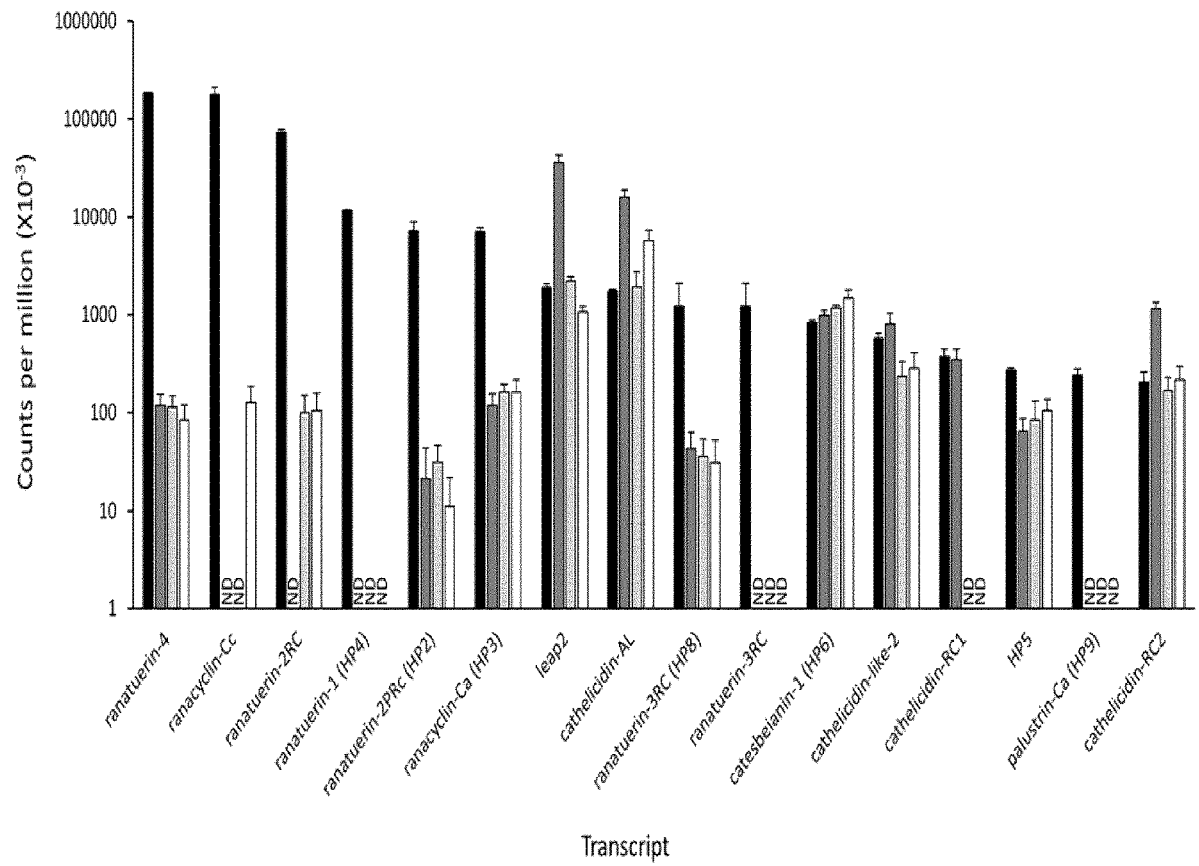

FIG. 3 illustrates that putative and known AMP-encoding transcripts show differential expression in *R. catesbeiana* premetamorphic tadpole back skin (black bars), liver (dark grey bars), olfactory epithelium (light grey bars), and tail fin (white bars).

FIG. 4 shows Clustal omega alignments of putative AMP precursor sequences with their closest known AMP matches. Panel A compares *Amolops loloensis* Cathelicidin-AL sequence (SEQ ID NO: 31) with the corresponding *R. catesbeiana* Cathelicidin-AL sequence (SEQ ID NO:32). Panel B compares *Nanorana parkeri* predicted LEAP2 sequence (SEQ ID NO:33) with the corresponding *R. catesbeiana* LEAP2 sequence (SEQ ID NO:34).

Figure 5:
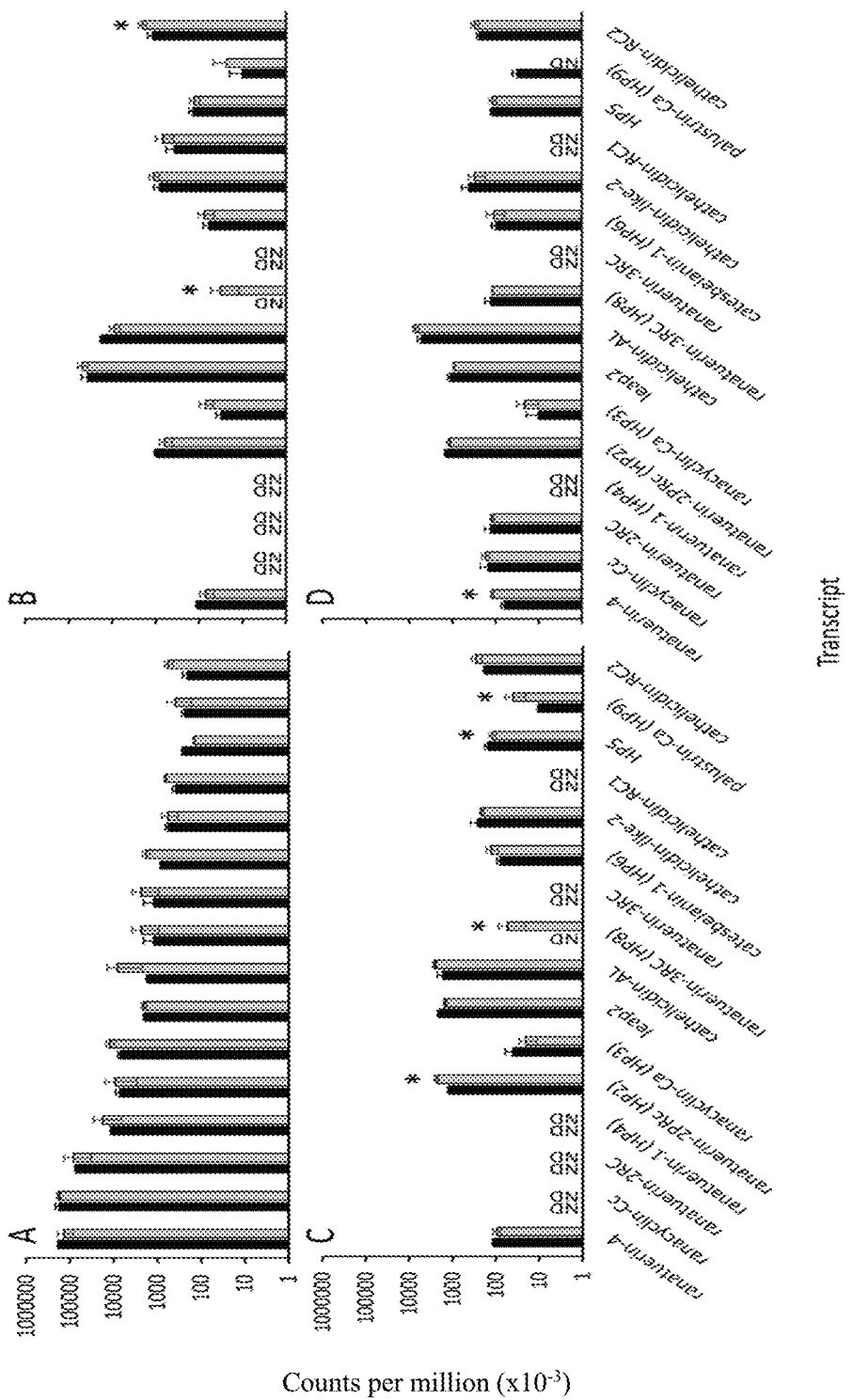

FIG. 5 shows RNA-seq data representing transcripts encoding the indicated putative and known AMPs are shown for tadpole Panel A—back skin; Panel B—liver; Panel C—olfactory epithelium; and Panel D tail fin from controls (black bars) versus tadpoles exposed to 10 nM T3 for 48 h (grey bars).

FIG. 6 shows ranatuerin-1 and ranatuerin-3RC genes containing 2 exons and which are alternatively spliced. The structure of the genes and derived transcripts encoding (Panel A) Ranatuerin-1 and Ranatuerin-1 (HP4), and (Panelo B) Ranatuerin-3RC and Ranatuerin-3RC (HP8), with top illustration representing the gene drawn to the indicated scale with the exonic portions depicted as black rectangles and intronic regions depicted by the thick black line. Intronic regions are shown as thin lines that are spliced out in the labelled transcripts below the gene. Grey rectangles in the spliced transcript indicate the untranslated regions, and hatched rectangles indicate the open reading frame.

Figure 7:
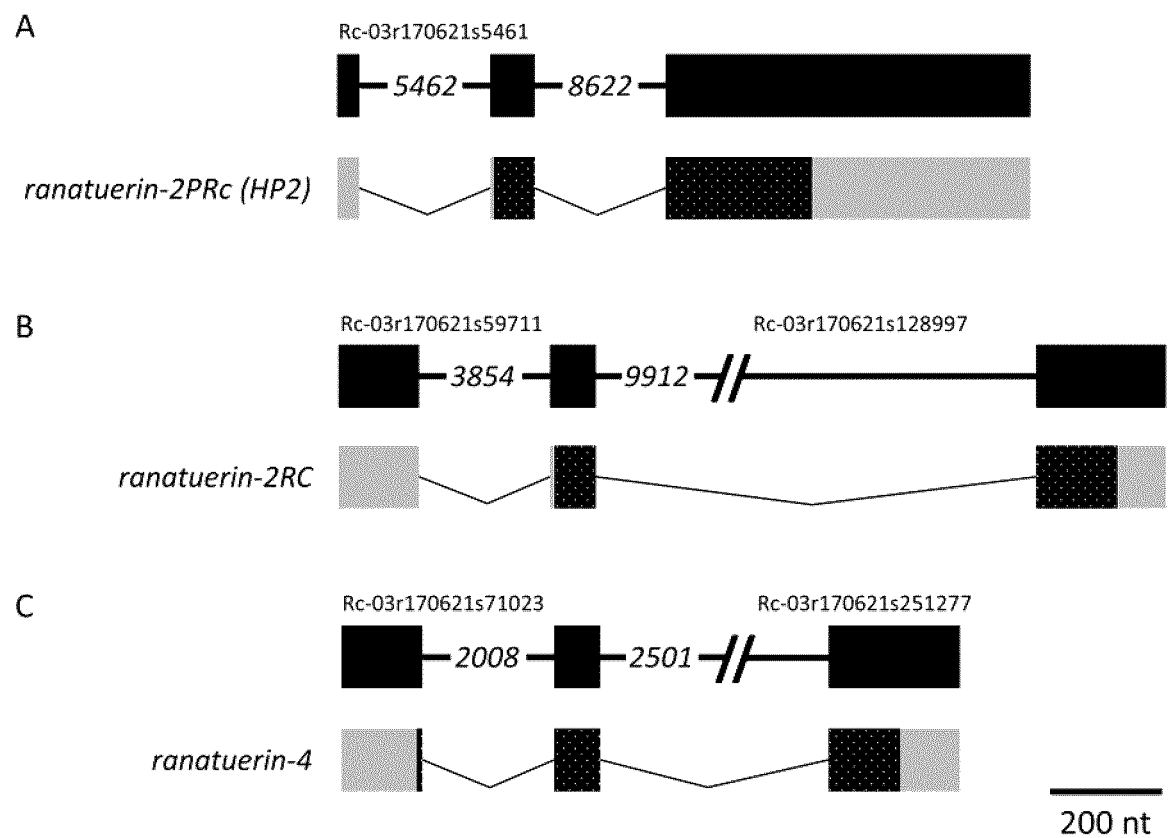

FIG. 7 shows the ranatuerin-2PRc (HP2), ranatuerin-2RC, and ranatuerin-4 genes, having 3 exons. The structure of the genes and derived transcripts encoding (Panel A) Ranatuerin-2PRc (HP2), (Panel B) Ranatuerin-2RC, and (Panel C) Ranatuerin-4 are shown.

FIG. 8 shows two genes, one with 3 exons and the other with 1 exon, encoding Ranacyclins. The structure of the genes and derived transcripts encoding (Panel A) Ranacyclin-Ca and Ranacyclin-Cc, and (Panel B) Ranacyclin-Ca (HP3) are shown.

Figure 9:
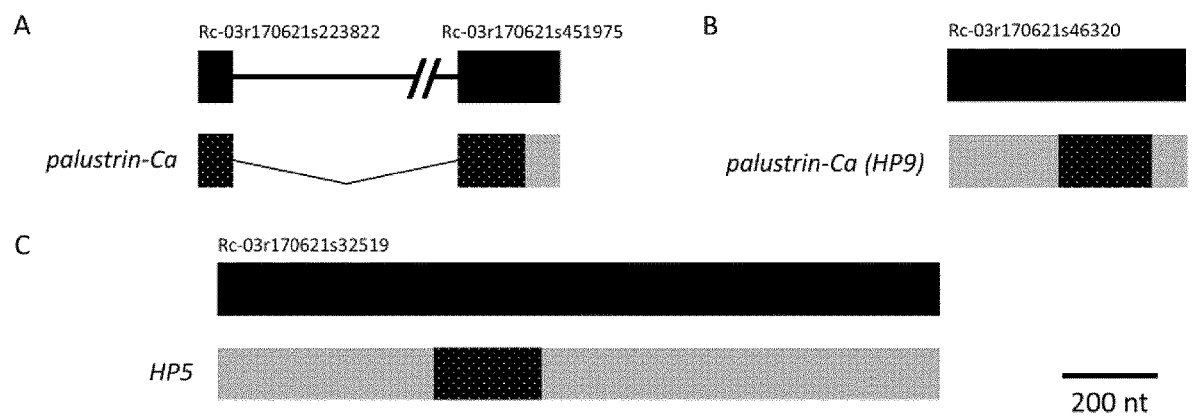

FIG. 9 shows Palustrin-Ca encoded by a 2 exon gene, and Palustrin-Ca (HP9) and HP5 are encoded by single exon genes. The structure of the genes and derived transcripts encoding (Panel A) Palustrin-Ca, (Panel B) Palustrin-Ca (HP9), and (Panel C) HP5 are shown.

Figure 10:
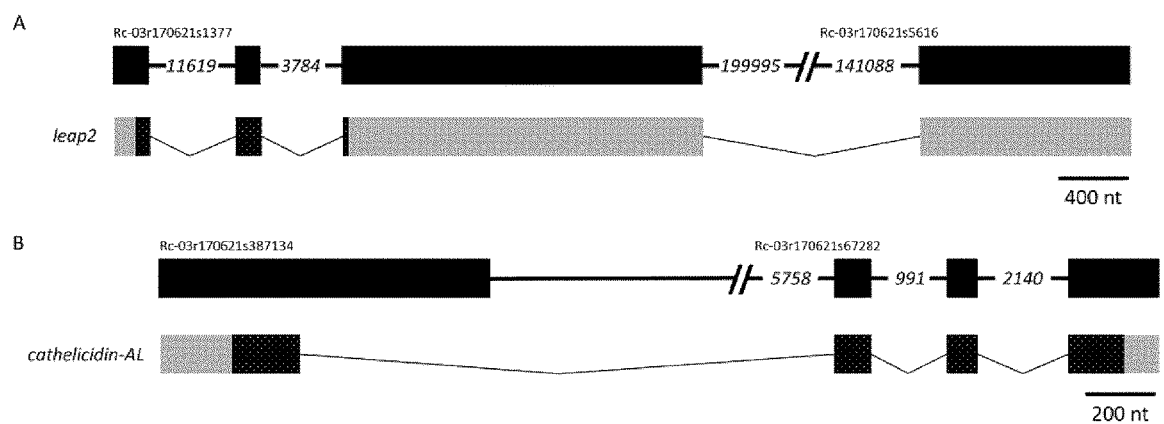

FIG. 10 illustrates both LEAP2 and Cathelicidin-AL as derived from four exons. The structure of the genes and derived transcripts encoding *R. catesbeiana* (Panel A) LEAP2 and (Panel B) Cathelicidin-AL are shown.

DETAILED DESCRIPTION

Peptides and/or amino acid sequences with antimicrobial properties are described herein. A bioinformatics approach, starting with sequences exhibiting effect, and making strategic modifications thereto, has led to the discovery of antimicrobial peptides. In a bioinformatics approach, sufficient similarity among sequences can be maintained so as to permit functional equivalency. Sequences similar to isolated sequences from which a consensus is derived are also described. Such similar sequences may contain conserved amino acid substitutions together with a limited number of non-conserved substitutions, such as modifications or deletions, but while still maintaining functionality.

These peptides and their pharmaceutical compositions and modifications thereof are also useful as therapies for microbial infections or as chemopreventative agents to slow or arrest the progression of microbial infections. Modifications of peptides described herein may include but are not limited to incorporation of the peptides or their modifications in lipid vesicles for enhanced therapeutic delivery and the modulation of other ADMET properties (absorption, distribution, metabolism, excretion, toxicity) as well.

Chemical modifications of the peptides are described, which are known to individuals skilled in the art of peptide chemistry to be useful to enhance stability and otherwise make the peptides more drug-like and useful for the desired applications. Such modifications include peptide cyclization and the use of amino acids of opposite chirality-so-called D-amino acids. Such modifications also include alternative backbone chemistries and novel side chains that retain the binding specificity.

Also described is the application of the peptides, and modifications of the peptides obvious to those skilled in the art, to other microbial targets. Antimicrobial therapies useful and effective in one type of infection may be useful and effective in other diseases.

Also described are vector constructs incorporating the disclosed peptides and/or their amino acid sequences and coding nucleic acid sequences for the purposes of the production of antimicrobial peptides.

The peptides described herein, and the modifications thereof are also useful in combination with other antimicrobial agents for the treatment or prevention of disease, such as an infectious disease or a cancer.

Uses of the AMPs either alone or as part of a kit in a procedure to isolate and identify their binding partners (target molecules) associated with the infectious agent are also described.

The peptides and/or amino acid sequences described herein have selective antimicrobial properties. Further aspects and advantages will become apparent from consideration of the ensuing description of various embodiments. A person skilled in the art will realize that other embodiments, combinations and variations are possible, and that the details described herein can be modified in a number of respects, all without departing from the overall concept. Thus, the following drawings, descriptions and examples are to be regarded as illustrative in nature and not restrictive.

Treatment or prevention of a disease or condition encompasses treatment before and after outward signs or symptoms of the disease or condition are present in the subject. For example, a subject exposed an infectious agent may or may not exhibit symptoms. Further, the prevention or prophylaxis of a disease or condition may encompass partial prevention, lessening of severity when onset occurs, decreasing likelihood of outward signs or symptoms, or preventing the spread of infection by keeping severity so low as to be undetectable or negligible. Treatment and prevention may involve modulating the immune system of the subject to the extent that the subject's own defenses ward off the disease or condition, such as infection. An inflammatory or anti-inflammatory effect of the peptides described herein may modulate the outward signs or symptoms of a disease or condition.

Anti-cancer activity, such as against solid tumours or liquid tumours, may be modulated by peptides as described herein. Indirect attack on cancer cells by the peptides described herein through effects on the immune system by the peptides may alleviate cancerous cell growth.

An antimicrobial peptide is described comprising: an amino acid sequence according to any one of SEQ ID NO:1 to SEQ ID NO:166, or a fragment or variant thereof, having at least 65% amino acid sequence identity to any one of SEQ ID NO:1 to SEQ ID NO:166. The threshold of amino acid sequence identity for the variant or fragment may optionally be at least 70%, at least 75%, at least 80%, at least 85%, at least 90%, or at least 95% amino acid sequence identity to any one of SEQ ID NO:1 to SEQ ID NO:166.

The antimicrobial peptide may be modified, or may be a variant which comprises a modification that is a conservative amino acid substitution. Such an amino acid sequences as are known in the art may include the following candidates, with the substitutable options shown in parentheses: Ala (Gly, Ser); Arg (Gly, Gln); Asn (Gln, His); Asp (Glu); Cys (Ser); Gln (Asn, Lys); Glu (Asp); Gly (Ala, Pro); His (Asn, Gln); Ile (Leu, Val); Leu (Ile, Val); Lys (Arg, Gln); Met (Leu, Ile); Phe (Met, Leu, Tyr); Ser (Thr, Gly); Thr (Ser; Val); Trp (Tyr); Tyr (Trp, Phe); and Val (Ile, Leu). Furthermore, 'functional' variants, mutations, insertions, or deletions encompass sequences in which the activity or function is substantially the same as that of the reference sequence from which the altered sequence is derived. Activity or function may be tested according to such parameters as described herein, such as MIC or MBC. Further, it may be desirable to reduce the antigenicity of a peptide, for example by PEGylated, or the peptide may comprise a D-amino acid. The peptide may be cyclized.

The antimicrobial peptide may be a peptide or a fragment that is up to 30 amino acids in length. For example, it may be a peptide or a fragment of up to 20 amino acids in length. An exemplary antimicrobial peptide may be one that comprises or consists of an amino acid sequence according to any one of SEQ ID NO:1 to SEQ ID NO:65.

A composition is described herein which comprises the antimicrobial peptide as described herein, together with a suitable excipient, such as a pharmaceutically acceptable carrier. The composition may be one that is suitable for use in treatment or prevention of a disease or condition, such as an infectious disease, or a cancer, such as may be attributable to a solid tumour or a liquid tumour.

The composition may be formulated for oral, injectable, rectal, topical, transdermal, nasal, or ocular delivery. Such compositions can thus be administered to subjects in need thereof through any acceptable route, such as topically (as by powders, ointments, or drops); oral tablets, capsules, gels or liquids; or rectal suppositories. Further modes of delivery include mucosally, sublingually, parenterally, intravaginally, intraperitoneally, bucally, ocularly, or intranasally.

When formulated for oral use or administration in a liquid formulation, the excipients or ingredients may include but are not limited to those accepted in the art of pharmaceutical formulations, for example emulsions, microemulsions, solutions, suspensions, syrups and elixirs. Liquid dosage forms may contain inert diluents such as water or other solvents, solubilizing agents, emulsifiers, ethyl alcohol, isopropyl alcohol, ethyl carbonate, ethyl acetate, benzyl alcohol, benzyl benzoate, propylene glycol, 1,3-butylene glycol, or dimethylformamide. Further, a liquid formulation may comprise oils such as cottonseed, groundnut, corn, germ, olive, castor, and sesame oils; glycerol, tetrahydrofurfuryl alcohol, polyethylene glycols and fatty acid esters of sorbitan; and mixtures thereof. Besides inert diluents, such oral compositions can also include adjuvants such as wetting agents, emulsifying and suspending agents, sweetening, flavoring, and perfuming agents.

The composition may be one that is lyophilized. The composition may comprise a suitable preservative.

The composition may be one that is distributed evenly in a diet intended for livestock, such as swine or poultry. Such a composition may be sprayed or mixed into a ground or powdered ingredient, and then mixed evenly into a coarser animal feed to ensure even distribution.

A use of the antimicrobial peptide is provided herein, for treatment or prevention of a disease or condition in a subject in need thereof, such as an infectious disease. The disease or condition may be a cancer, such as a solid tumour or a liquid tumour.

Further, a use is provided for preparation of a medicament for treatment or prevention of such a disease or condition in a subject in need thereof. A method of treating or preventing such a disease or condition is also described herein, which comprises administering to a subject in need thereof an effective amount of the peptide or the composition described herein.

The disease or condition may be one attributable to Gram-negative bacteria, or it may be a disease or condition attributable to Gram-positive bacteria. The disease or condition may be one that is attributable to acid fast bacteria, or one that is attributable to bacteria that has become resistant to other drugs. Such diseases or conditions may be ones attributable to *E. coli, S. enterica, S. aureus, P. aeruginosa, S. pyogenes, M. smegmatis*, MRSA, *S. enteritidis* or S. Heidelberg bacteria, for example.

Further, the disease or condition may be a cancer, such as a solid tumour or a liquid tumour.

A lipid vesicle may be used to deliver the antimicrobial peptide described herein. A nucleic acid molecule encoding the antimicrobial peptide described is also envisioned. A vector comprising the nucleic acid molecule is also encompassed.

A method of identifying a target molecule associated with an infectious agent is described, wherein the target molecule binds to the antimicrobial peptide described herein. Such a method involves the step of screening a library of candidate target molecules associated with the infectious agent, for a molecule that binds to the antimicrobial peptide. The infectious agent may be Gram-negative bacteria, or may be Gram-positive bacteria. Further, the infections agent may be acid fast bacteria, or bacteria that has become resistant to other drugs. Exemplary infectious agents include but are not limited to *E. coli, S. enterica, S. aureus, P. aeruginosa, S. pyogenes, M. smegmatis*, MRSA, *S. enteritidis* or S. Heidelberg bacteria. Further, a method of identifying a target molecule for modulating biological activity is described, wherein the target molecule binds to a peptide as described herein. The method comprising the step of screening a library of candidate target molecules for a molecule that binds to the peptide. Modulating of biological activity may comprise anti-tumour action, anti-inflammatory action, or inflammatory action. In such methods of target identification, the screening of a library of candidate target molecules may comprise in silico screening.

A kit is encompassed herein for identifying a target molecule associated with an infectious agent. Such a kit comprises an antimicrobial peptide as described herein together with instructions for conducting the method described herein for identifying a target molecule associated with the infectious agent. Optionally, additional reagents may be provided with the kit. A kit for identifying a target molecule for modulating biological activity, is also described. Such a kit comprises a peptide, as described herein, together with instructions for conducting a screening method for molecules that bind to the peptide.

EXAMPLES

The following Examples outline exemplary embodiments and/or studies conducted pertaining thereto. While the Examples are illustrative, they should not be viewed as limiting.

Example 1

Bioinformatics Approach: Antimicrobial Peptides from *R. catesbeiana* Transcripts Summary Antimicrobial peptides (AMPs) exhibit broad-spectrum antimicrobial activity, and have promise as new therapeutic agents. While the adult North American bullfrog (*Rana* [*Lithobates*] *catesbeiana*) is a prolific source of high-potency AMPs, the aquatic tadpole represents a relatively untapped source for new AMP discovery. The recent publication of the bullfrog genome and transcriptomic resources provides an opportune bridge between known AMPs and bioinformatics-based AMP discovery. The objective of the present study was to identify novel AMPs with therapeutic potential using a combined bioinformatics and wet lab-based approach. In the present study, seven novel AMP precursor-encoding transcripts expressed in the tadpole were identified. Comparison of their amino acid sequences with known AMPs revealed evidence of mature peptide sequence conservation with variation in the prepro sequence. Two mature peptide sequences were unique and demonstrated bacteriostatic and bactericidal activity against Mycobacteria but not Gram-negative or Gram-positive bacteria. Nine known and seven novel AMP-encoding transcripts were detected in premetamorphic tadpole back skin, olfactory epithelium, liver, and/or tail fin. Treatment of tadpoles with 10 nM 3,5,3'-triiodothyronine for 48 h did not affect transcript abundance in the back skin, and had limited impact on these transcripts in the other three tissues. Gene mapping revealed considerable diversity in size (1.6-15 kbp) and exon number (one to four) of AMP-encoding genes with clear evidence of alternative splicing leading to both prepro and mature amino acid sequence diversity. These findings verify the accuracy and utility of the bullfrog genome assembly, and set a firm foundation for bioinformatics-based AMP discovery.

Introduction

Antibiotic resistance among bacterial pathogens that cause prevalent global diseases has emerged as one of the most critical public threats facing the world today[1-3]. An analysis conducted by the Centers for Disease Control and Prevention estimates that at least 23,000 deaths in the United States each year are attributed to infections caused by antibiotic-resistant organisms[1]. In 2015, the World Health Organization endorsed a global action plan to combat antimicrobial resistance with strategic objectives that include optimizing the use of antimicrobial agents and sustainable investment in countering antimicrobial resistance[4]. Consequently, discovery and development of alternative antimicrobials is an urgent global need. As an alternative to traditional antibiotic therapy, antimicrobial peptides (AMPs) are garnering interest as potential therapeutics[5]. AMPs are a diverse class of peptides produced by all multicellular organisms as a defense against a broad spectrum of pathogens including bacteria, fungi, and viruses, and are considered central components of the innate immune system[6-8].

Although overall AMPs exhibit remarkable sequence and structural diversity, commonalities include a typical length less than 100 amino acids, a positive net charge, and membership in one of four distinct groups based on their secondary structures: β-strand, α-helix, extended coil, and loop. Of these groups, α-helix AMPs are the most studied and most common[6,9,10]. The cationic nature of AMPs, along with a distribution of hydrophobic residues, enable these peptides to interact with and neutralize pathogens, and contribute to their overall function[6,11].

AMP structure may show variability across the tree of life[12]. Amphibian AMPs are generally composed of an N-terminal signal peptide presequence, an adjacent prosequence that functions to maintain the AMP in an inactive conformation, and a C-terminal mature peptide sequence. All eukaryotic AMPs are synthesized as precursors that are proteolytically processed by propeptide convertases to yield active, mature peptides[8,13-15]. While AMP signal peptides and prosequences are typically conserved within families, the mature peptide sequences vary considerably, and constitute the functional portion of the antimicrobial peptide[8]. These characteristics can be exploited to identify and characterize novel AMPs from a large dataset[10]. Furthermore, because of the multifaceted mechanisms of antimicrobial action employed by AMPs, such as destruction of microbial membranes[16], inhibition of macromolecule synthesis[17], and peptide-induced modulation of the immune system[18], microbes are less likely to develop resistance against these peptides than against conventional antibiotics. Several AMPs are currently used in a clinical setting, and many more AMPs are undergoing clinical trials to ascertain their therapeutic potential[11].

The predominant approaches for isolating new AMPs involves chromatography- and/or mass spectrometry-based analyses of protein samples from body fluids or tissues in combination with antimicrobial assays, peptide sequencing, and de novo peptide synthesis. However, context-specific protein expression, the cost of implementation, and low throughput experimentation associated with traditional AMP identification methods that employ analytical chemistry have hindered AMP discovery progress. This emphasizes the need to develop an alternative approach for the identification of novel AMPs with therapeutic potential.

Adult frog skin is an abundant source of AMPs due to specialized granular glands in the dermis that synthesize and store these peptides, which are secreted onto the skin surface at the first sign of injury or microbial challenge[6,9,19]. From an evolutionary survival perspective, this rich repertoire of AMPs within frog skin is a beneficial adaptation to their wet and muddy environments where pathogens are plentiful. As of this writing, the curated Antimicrobial Peptide Database (APD)[19] contains sequences for 978 active peptides originating from frog skin (out of 1043 amphibian peptides). This represents 34% of the AMP database compendium, which includes peptide sequences derived from six kingdoms including bacteria, archaea, protists, fungi, plants, and animals as well as some synthetic peptides (http://aps.unmc.edu/AP/main.php). Furthermore, the utility and efficacy of some frog AMPs as potential therapeutics has been demonstrated previously[20-22].

AMP secretion is not just limited to amphibians, nor limited to the skin or a specific developmental stage. For example, liver-expressed antimicrobial peptides (LEAPs) are highly abundant in the liver and midgut and, in humans and fish, are secreted into the blood[23-25]. As amphibians, most frogs experience life in two distinct postembryonic forms: as a free-living aquatic larval tadpole and as an air-breathing terrestrial frog. The demands on the innate immune system differ as the types of pathogens living in each environment can differ substantially. Therefore, there is an opportunity to identify novel AMPs expressed in the larval stage. Tadpole-specific studies conducted to date have focused on testing natural skin secretions collected from a mixture of different aged tadpoles after immersion in or injection of norephinephrine. This established that these skin secretions could defend against parasitic worm infection and survival[26]. Using mass spectrometry, Woodhams and coworkers[27] compared the norephinephrine-induced skin secretions of 17 frog species and found that Ranatuerin-2, -4, -6, -7, -8, and -9, Palustrin-2CBa, Bradykinin, Temporin-1P, and Ranalexin were the most abundant peptides. Generally, tadpoles had a lower proportion of AMPs relative to adults, but their profiles are distinct from each other[27]. Of these, Ranatuerin-2, -7, -8, -9, and Ranalexin were found even in the absence of norephinephrine induction[27]. An interesting finding was that tadpoles with longer larval periods, such as that of *R. catesbeiana*, produced a greater AMP defense response than tadpoles with short larval periods showing differential investment in the innate immune response at this aquatic developmental phase[27].

Herein, the development of a bioinformatics approach for the identification and characterization of putative AMPs based on peptide homology is demonstrated. A manually curated AMP sequence database was used to search the rich genomic resources compiled for the North American bullfrog, *Rana* (*Lithobates*) *catesbeiana*[28]. Two novel bullfrog AMPs were identified that demonstrate antimicrobial activity via an established microtiter broth dilution method[29]. Through computational methods applied to transcriptomics and genome data, the expression profile and gene structures of twenty AMP-encoding transcripts were examined, sixteen of which are found in tadpole tissues.

Results

Identification of putative AMP-encoding transcripts. A systematic stepwise in silico query of the Bullfrog Annotated Reference Transcriptome (BART[28]) database is outlined in the Methods section and resulted in the identification of seven *R. catesbeiana* transcripts encoding novel precursor AMPs (shown in Table 1) and eleven known precursor AMTPs (shown in Table 2).

Table 1 shows the characteristics of putative AMP sequences identified through bioinformatic analysis of bullfrog tadpole RNA-seq data. Each peptide sequence is separated into the prepro sequence and the presumed mature peptide sequence. Computational predictions of net charge, molecular weight (MW), and isoelectric point (pI) of the mature peptide are shown, as well as a Peptide ID for easy reference.

TABLE 1

Prepro Sequences and Putative Mature Peptide Sequences

| Prepro sequence | Putative Mature Peptide Sequence | Net Charge | MW | pI | Peptide ID |
|---|---|---|---|---|---|
| MFTMKKSLLLLFFLGTI SLSLCEQERNADDDQGE VIEQKVKR (SEQ ID NO: 1) | AFLSTVKNTLINVAGTMID TFKCKITGVC (SEQ ID NO: 2) | +2 | 3077.7 | 8.6 | HP2 |
| VLLYLIITVSFPRRDAN DEDGGEVTKEVVKR (SEQ ID NO: 3) | SLSGCWTKSFPRKPCLRNR (SEQ ID NO: 4) | +5 | 2236.6 | 10.9 | HP3 |
| MSSFCEITNVALTISLS SPRRGADEEEGNGEKEI KR (SEQ ID NO: 5) | SMLSVLKNLGKVGLGFVAC KINKQC (SEQ ID NO: 6) | +4 | 2651.3 | 9.6 | HP4 |
| MTQSTQKWFKTKYWRVR NRPAMSPDLNPIEHLWR DLKKVVGKR (SEQ ID NO: 7) | NPSNLRALEELVKEECSEI PVERCKKLIYGYRK (SEQ ID NO: 8) | +1 | 3908.5 | 8.0 | HP5 |
| MRKRMTMRRMMKKKSE KERRERGKR (SEQ ID NO: 9) | MMRVMRRKTKVIWEKKDFI GLYSID (SEQ ID NO: 10) | +4 | 3144.8 | 102 | HP6 |
| MFFMSSPRRDADEVKEV KR (SEQ ID NO: 11) | GFLDIIKNLGKTFAGHMLD KIKCTIGTCPPSP (SEQ ID NO: 12) | +2 | 3417.1 | 8.6 | HP8 |
| MITVSSPRRDADGDEGE VEEVKR (SEQ ID NO: 13) | GFLDIIKDIGKEFAVKILN NLKCKLAGGCPP (SEQ ID NO: 14) | +2 | 3304.0 | 8.6 | HP9 |

The translated "novel" precursor AMPs include a trypsin cleavage site (a common convertase cleavage site in AMPs) and, apart from one sequence that begins with a valine (HP3), all have a methionine at the N-terminus (Table 1). Further, the putative mature peptides all possess a predicted net positive charge at neutral pH, are between 19 and 33 AA in length, and have isoelectric points (pI) between 8.0 and 10.9 (Table 1). All of these physicochemical properties are consistent with those of known AMPs[19].

Table 2 shows transcript, protein, and gene characteristics of 20 known and putative AMPs evaluated within the present study.

TABLE 2

Transcript, protein, and gene characteristics of 20 known and putative AMPs evaluated within the present study.

| AMP name | Closest NCBI nucleotide sequence Accession #/ Length (nt) | Closest NCBI precursor protein sequence Accession #/ Length (AA)/ Species | New Rana catesbeiana transcripts from BART Accession #/ Length (nt)/ Length (AA) | Rana catesbeiana gene information Genome scaffold/Strand/Scaffold length (bp)/[Range of overlap with query sequence by scaffold nt position]/Exon # |
|---|---|---|---|---|
| catesbeianin-1 | FJ830640/ 324 | ACR84056/42/ Rana/ catesbeiana | N/A[a] | None |
| catesbeianin-1 (HP6) | FJ830640/ 324 | ACR84056/42/ Rana/ catesbeiana | GFBS01479282/ 626/51 | None |
| cathelicidin-like-2 | KF766531/ 700 | AHW58221/ 156/Rana/ catesbeiana | MH800186/ 753/155 | None |
| cathelicidin-AL | JF923766/ 648 | AEI69698/179/ Amolops/ loloensis | MH800187/ 1019/181 | Rc-03r170621s387134/Rc-03r170621s67282/+/−/1650/ 14834/[1-400/9076-8969, 7977-7888, 5747-5490]/4 |
| cathelicidin-RC1 | KF766530/ 677 | AHW58220/ 151/Rana catesbeiana | MH800188/ 926/151 | None |
| cathelicidin-RC2 | KF766531/ 700 | AHW58221/ 156/Rana catesbeiana | MH800189/ 753/155 | None |
| HP5 | None | None | GFBS01753449/ 1523/76 | Rc-03r170621s32519/+/36533/ [3251-4772]/1 |
| leap2 | XM_ 018563220/ 469 | XP_01841872281/ Nanorana parkeri | MH800190/ 3507/81 | Rc-03r170621s1377; Rc-03r170621s5616/ +/+/[279751/290780]/[62065-62169, 73789-73937, 77722-79756/ 141039-142257]/4 |
| palustrin-Ca | FJ830669/ 322 | ACR84085/ 71/Rana catesbeiana | N/A | Rc-03r170621s223822/Rc-03r170621s451975/+/+/[2611/ 1423]/[2144-2217/128-343]/2 |
| palustrin-Ca (HP9) | FJ830669/ 322 | ACR84085/ 71/Rana catesbeiana | GFBS01150567/ 527/54 | Rc-03r170621s46320[b]/+/24012/ [18718-19222]/1 |
| ranacyclin-Ca | FJ830643/ 311 | ACR84059/ 63/Rana catesbeiana | N/A | Rc-03r170621s43867/+/25684/ [10079-10152, 12881-13068]/2 |
| ranacyclin-Ca (HP3) | FJ830643/ 311 | ACR84059/63/ Rana catesbeiana | GFBS01071740/ 1143/ 50[c] | Rc-03r170621s29221/−/41060/ [20482-19341]/1 |
| ranacyclin-Cc | FJ830653/ 296 | ACR84069/67/ Rana catesbeiana | GFBS01607132/ 524/62 | Rc-03r170621s43867/−/25684/ [8419-8475, 10070-10152, 12881-13075]/3 |
| ranatuerin-1 | FJ842524/ 314 | ACR46972/66/ Rana catesbeiana | N/A | Rc-03r170621s168979/−/3446/ [2612-2539, 1247-1038]/2 |
| ranatuerin-1 (HP4) | KZ060483/ 3446 | PIO12229/61/ Rana catesbeiana | N/A | Rc-03r170621s168979/−/3446/ [1475-1107]/1 |
| ranatuerin-2PRc (HP2) | JQ511836/ 253 | AFR43665/71/ Pseudacris regilla | GFBS01116610/ 772/71 | Rc-03r170621s5461/−/149396/ [114249-114211/108748-108668/ 100045-99394]/3 |
| ranatuerin-2RC | FJ830657/ 335 | ACR84073/74/ Rana catesbeiana | GFBS01229406/ 500/74 | Rc-03r170621s59711/Rc-03r170621s128997/+/−/[17230/ 5085]/[7179-7319, 11174-11256/ 4558-4326]/3 |
| ranatuerin-3RC | FJ830656/ 309 | ACR84072/68 Rana catesbeiana | N/A | Rc-03r170621s223822/Rc-03r170621s584290/+/−/[2611/ 1023]/[2144-2217/734-530]/2 |
| ranatuerin-3RC (HP8) | FJ830656/ 309 | PIO09118/51/ Rana catesbeiana | GFBS01228991/ 519/51 | Rc-03r170621s584290/−/1023/ [1007-532]/1 |

TABLE 2-continued

Transcript, protein, and gene characteristics of 20 known and putative AMPs evaluated within the present study.

| AMP name | Closest NCBI nucleotide sequence Accession #/ Length (nt) | Closest NCBI precursor protein sequence Accession #/ Length (AA)/ Species | New Rana catesbeiana transcripts from BART Accession #/ Length (nt)/ Length (AA) | Rana catesbeiana gene information Genome scaffold/Strand/Scaffold length (bp)/[Range of overlap with query sequence by scaffold nt position]/Exon # |
|---|---|---|---|---|
| ranatuerin-4 | BT081520/ 332 | ACO51651/70/ Rana catesbeiana | GFBS01229403/ 504/70 | Rc-03r170621s71023/Rc-03r170621s251277/+/−/[13560/ 2355]/[8821-8968, 10977-11059/ 2198-1964]/3 |

[a] N/A indicates that the sequence found in the BART database was the same length as the Rana catesbeiana sequence already present in the NCBI database or that this sequence was not found in the BART database.
[b] This scaffold contained sequence that was 93% identical to the HP9 sequence but had 17 AA changes and an in-frame deletion of V36
[c] Translation begins with a V instead of M Examination of putative AMP protein sequences. Blastx analyses of the seven transcripts identified protein sequence matches in the NCBI nr database ranging from 49-77% sequence identity (Table 3) and one sequence (HP5) had no notable match with any known AMP.

FIG. 1 shows Clustal omega alignments of putative AMP precursor sequences with their closest known AMP matches. Panel A shows a comparison of the *Pseudacris regilla* Ranatuerin-2PRc sequence (top) (SEQ ID NO:15) with the *R. catesbeiana* HP2 sequence (bottom) (SEQ ID NO:16). Panel B shows alignments of seven Ranatuerin precursor sequences (SEQ ID NO:17 to SEQ ID NO:23) from *R. catesbeiana*. Panel C shows alignments of Ranacyclin precursor sequences from *R. catesbeiana* (SEQ ID NO:24 to SEQ ID NO:26). Panel D shows alignments of Catesbeianin-1 precursor sequences (SEQ ID NO:27 and SEQ ID NO:28) from *R. catesbeiana*. Panel E shows alignments of Palustrin-Ca precursor sequences (SEQ ID NO:29 and SEQ ID NO:30) from *R. catesbeiana*. The conserved proteolytic cleavage site is shown in bold and underlined. This cleavage site indicates the border for the N-terminal prepro sequence and the C-terminal mature sequence. The precursor peptide lengths are indicated to the right of each sequence. The dots represent conserved amino acid substitutions and asterisks indicate exact matches. Dashes were introduced to maximize sequence alignments. Further details regarding NCBI accession numbers are in Table 2.

Table 3 shows a comparison of sequence identities (%) of the AMP candidates with their best-known AMP blastp matches over the entire sequence (precursor), or by prepro sequence or mature sequences. There was no AMP match with HP5.

TABLE 3

Peptide Sequence Identities

| Peptide ID | Highest scoring blastp match | Sequence Identity (%) | | |
|---|---|---|---|---|
| | | Precursor | Prepro | Mature |
| HP2 | Ranatuerin-2PRc | 77 | 83 | 69 |
| HP3 | Ranacyclin-Ca | 49 | 41 | 68 |
| HP4 | Ranatuerin-1 | 68 | 49 | 100 |
| HP5 | None | None | None | None |
| HP6 | Catesbeianin-1 | 76 | 54 | 100 |
| HP8 | Ranatuerin-3RC | 65 | 33 | 100 |
| HP9 | Palustrin-Ca | 65 | 38 | 100 |

Closer examination of the peptide sequences revealed that four of the predicted mature peptides (HP4, HP6, HP8, HP9) are identical to known AMPs (Table 3 and FIG. 1), while the corresponding prepro regions exhibit identities ranging from 65-76% (Table 3 and FIG. 1). The remaining two candidate AMP peptides (HP2 and HP3) exhibited 69% (HP2) and 68% (HP3) identity to their best-known AMP mature peptide sequence matches (Table 3). The HP2 and HP3 prepro sequences also show considerable divergence from their best-known AMP match (amino acid identities of 77% and 49%, respectively; Table 3).

The HP2 sequence is the *R. catesbeiana* counterpart of the *Pseudacris regilla* Ranatuerin-2PRc sequence (FIG. 1, Panel A). When compared to the other known or putative AMP precursors, the Ranatuerin-2PRc (HP2) sequence exhibits a reasonable degree of sequence conservation with other Ranatuerins in the prepro sequence, but considerable divergence in the mature peptide (FIG. 1, Panel B). The putative mature peptide sequences of HP4 and HP8 are identical to the mature peptides of Ranatuerin-1 and Ranatuerin-3RC, respectively, but each has a distinct prepro sequence (FIG. 1, Panel B). The mature peptide region of HP3 is 68% identical to Ranacyclin-Ca, with substantial sequence divergence in the prepro sequence (41% identity; FIG. 1, Panel C). The mature peptide regions of HP6 and HP9 are identical to Catesbeianin-1 and Palustrin-Ca, respectively, but have divergent N terminal ends in the prepro sequences (FIG. 1, Panel D and Panel E).

FIG. 2 shows SABLE secondary structure prediction comparisons between the derived mature peptides of Panel A—HP2; Panel B—HP3; and Panel C—HP5 versus known mature AMP sequences. Panel D shows the legend for the SABLE predictions with amino acid (AA) position indicated at the top, the predicted secondary structure in the middle and the relative solvent accessibility (RSA) at the bottom. Confidence predictions are below the predicted secondary structure and RSA. For the predicted secondary structure, red lines, α helices; green arrows, β sheets; blue lines, extended coils. RSA is indicated by grey scale from black (0-9% RSA) to white (90-100% RSA) where each box represents an amino acid.

The secondary structure of the putative mature HP2 peptide contains an α-helix, extended coil, β-strand arrangement that resembles a mixture of Ranatuerin-1 and Ranatuerin-2RC secondary structure FIG. 2, Panel A. The putative mature HP3 peptide is solely extended coil similar to Ranacyclin-Ca (FIG. 2, Panel B) while the putative mature HP5 peptide is comprised of two α-helices separated by a small extended coil (FIG. 2, Panel C).

Microtiter broth dilution assays. HP2, HP3, and HP5 peptides are comprised of novel sequences that have not yet been described in the AMP literature. A common method for establishing antimicrobial activity of peptides is to perform microtiter broth assays. Microtiter broth dilution methods were implemented for determination of the minimum inhibitory concentration (MIC) and minimum bactericidal concentration (MBC). HP3 and HP5 were tested in addition to Ranatuerin-1/HP4 peptide as a positive control. HP2 could not be tested because multiple peptide synthesis attempts failed. The human cathelicidin, LL-37[30] was used as an additional positive control, and an unrelated similarly sized cationic peptide from the *T. pallidum* protein Tp0751 was used as a negative control. The potential AMPs were tested against bacteria representative of all three types of known cell envelope (Gram-positive, negative, and the complex and unique mycobacterial cell wall/envelope), given that a major mechanism used by AMPs is cell wall/membrane targeting.

Five bacterial species were tested, spanning Gram-negatives (*Escherichia coli* and *Pseudomonas aeruginosa*), Gram-positives (*Staphylococcus aureus* and *Streptococcus pyogenes*), and *Mycobacterium smegmatis* (neither a true Gram-positive nor Gram-negative). The Ranatuerin-1 peptide had some activity against *E. coli* and *S. aureus* (MIC: 48 and 97 µM, respectively) which is higher than previously reported[31] and some bacteriocidal activity was observed (MBC: 12-48 and 97 µM, respectively). This peptide had no effect on *S. pyogenes* or *P. aeruginosa*. HP3 and HP5 had no effect on inhibitory or bacteriostatic activity against *E. coli*, *S. aureus*, *S. pyogenes*, or *P. aeruginosa*.

Table 4 shows minimum inhibitory concentrations (MIC) and minimum bactericidal concentrations (MBC) in µM against *M. smegmatis* for tested known and putative AMPs from a minimum of five (MIC) and three (MBC) independent experiments. LL-37 is a human cathelicidin positive control and Tp0751 is a negative control peptide from *T. pallidum*. "-", no effect observed.

TABLE 4

Minimum Inhibitory Concentrations and
Minimum Bactericidal Concentrations

| | µM | |
|---|---|---|
| Peptide Name | MIC | MBC |
| HP3 | 4-14 | 7-14 |
| HP4/Ranatuerin-1 | 2-12 | 3-48 |
| HP5 | 66 | ≥66 |
| LL-37 | 0.4-2 | 1-28 |
| Tp0751 | — | — |

Except for the negative control peptide, all peptides had bacteriostatic activity against *M. smegmatis* (Table 4). Compared to Ranatuerin-1, HP3 had comparable bacteriostatic activity (MIC: 4-14 versus 2-12 µM; Table 4), and better bactericidal activity (MBC: 7-14 versus 3-48 µM; Table 4). HP5 exhibited weak bacteriostatic and bacteriocidal activity against *M. smegmatis* (Table 4).

Expression of AMP-encoding transcripts in *R. catesbeiana* tadpole tissues. The abundance levels of twenty AMP-encoding transcripts (thirteen known and seven novel identified above; listed in Table 2) were assessed in premetamorphic *R. catesbeiana* tadpole back skin, liver, olfactory epithelium, and tail fin using normalized RNA-seq data from previous studies[28, 33].

FIG. 3 shows putative and known AMP-encoding transcripts show differential expression in *R. catesbeiana* premetamorphic tadpole back skin, liver, olfactory epithelium, and tail fin. RNA-seq data representing transcripts encoding the indicated putative and known AMPs are shown for tadpole back skin (black bars, n=3), liver (dark grey bars, n=15), olfactory epithelium (light grey bars, n=15), and tail fin (white bars, n=15). Bars represent normalized median read counts per million and whiskers represent median absolute deviation. ND, not detected.

FIG. 4 shows Clustal omega alignments of putative AMP precursor sequences with their closest known AMP matches. Panel A shows a comparison of the *Amolops loloensis* Cathelicidin-AL sequence (NCBI Accession #AEI69698; top) with the corresponding *R. catesbeiana* Cathelicidin-AL sequence (bottom). Panel B shows a comparison of the *Nanorana parkeri* predicted LEAP2 sequence (NCBI Accession #XP_018418722; top) with the corresponding *R. catesbeiana* LEAP2 sequence (bottom). The conserved proteolytic cleavage site is bold and underlined. This cleavage site indicates the border for the N-terminal prepro sequence and the C-terminal mature sequence. The precursor peptide lengths are indicated to the right of each sequence. The dots represent conserved amino acid substitutions and asterisks indicate exact matches. Dashes were introduced to maximize sequence alignments. Further details regarding NCBI accession numbers are in Table 2.

Sixteen of these transcripts are in one or more of these tissues (FIG. 3). All of the indicated transcripts in FIG. 3 were sequence-verified from *R. catesbeiana* contigs including transcripts encoding Cathelicidin-AL (87% identity with *Amolops loloensis* precursor protein; FIG. 4) and LEAP2 (88% identity with *Nanorana parkeri* predicted precursor protein; FIG. 4). In several cases, the RNA-seq-derived sequences provided substantial improvements in length over transcript sequences already curated in GenBank (Table 2).

All sixteen transcripts are present in the tadpole back skin, while 11 are in the liver and olfactory epithelium, and 12 in the tail fin (FIG. 3). The most abundant transcripts are ranatuerin-4, ranacyclin-Cc, ranatuerin-2RC, and ranatuerin-1 (HP4) in the back skin; leap2, cathelicidin-AL, cathelicidin-RC2, and catesbeianin-1 (HP6) in the liver; leap2, cathelicidin-AL, catesbeianin-1 (HP6), and cathelicidin-like-2 in the olfactory epithelium; and cathelicidin-AL, catesbeianin-1 (HP6), leap2, and cathelicidin-like-2 in the tail fin (FIG. 3). Of note are the transcripts that are not in these premetamorphic tadpole tissues such as catesbeianin-1, ranacyclin-Ca, ranatuerin-1, and palustrin-Ca. These transcripts, which are detected in adult frog skin[31], are replaced by catesbeianin-1 (HP6), ranacyclin-Ca (HP3), ranatuerin-1 (HP4), ranatuerin-3RC (HP8), and palustrin-Ca (HP9) (FIG. 3).

Previous work indicated that mRNAs encoding some AMPs increase from very low or undetectable levels in tadpoles to high levels in the frog as a consequence of thyroid hormone-dependent metamorphosis[34-37]. These determinations were done with either whole tadpole homogenates[34,36] or skin[35,37].

FIG. 5 shows Putative and known AMP-encoding transcripts generally are not responsive to 10 nM $T_3$ treatment of tadpoles. RNA-seq data representing transcripts encoding the indicated putative and known AMPs are shown for tadpole (Panel A) back skin (n=3), (Panel B) liver (n=5), (Panel C) olfactory epithelium (n=5), and (Panel D) tail fin (n=5) from vehicle controls (black bars) or tadpoles exposed to 10 nM $T_3$ for 48 h (grey bars). Bars represent median read counts and whiskers represent median absolute deviation.

The asterisk indicates statistical significance between treatments at p<0.05. ND, not detected.

Premetamorphic tadpoles were immersed in 10 nM triiodothyronine ($T_3$) for 48 h which precociously induces metamorphosis by altering tissue-specific gene expression programs[28, 33], and determined the abundance of the AMP-encoding transcripts (FIG. 5). None of these transcripts was responsive to $T_3$ in the back skin (FIG. 5, Panel A). While the vast majority of transcripts also were not responsive to $T_3$ treatment in the liver, olfactory epithelium, and tail fin (FIG. 5, Panel B to Panel D), ranatuerin-3RC (HP8) transcripts appeared in the liver and olfactory epithelium (FIG. 5, Panel B and Panel C). Significant increases in mRNA abundance were observed for cathelicidin-RC2 (2-fold) in the liver; ranatuerin-2PRc (HP2) (2-fold) and palustrin-Ca (HP9) (4-fold) in the olfactory epithelium; and ranatuerin-4 (2-fold) in the tail fin (FIG. 5, Panel B to Panel D). A slight but significant decrease (1.3-fold) in HP5 transcripts was observed in the olfactory epithelium (FIG. 5, Panel C). Palustrin-Ca (HP9) mRNA disappeared in the tail fin upon $T_3$ treatment, but this was not significant (FIG. 5, Panel D).

AMP-encoding gene structures in the bullfrog genome. It is possible that the new versions of the above transcripts were products of alternative gene splicing. Using the recently published draft bullfrog genome[28], gmap and blastn were used to create gene models from the transcript sequences.

FIG. 6 shows the ranatuerin-1 and ranatuerin-3RC genes contain 2 exons and are alternatively spliced. The structure of the genes and derived transcripts encoding Panel A—Ranatuerin-1 and Ranatuerin-1 (HP4), and Panel B—Ranatuerin-3RC and Ranatuerin-3RC (HP8) are shown. The top illustration represents the corresponding gene drawn to the indicated scale with the exonic portions depicted as black rectangles and intronic regions depicted by the thick black line. The additional non-genic sequences flanking the indicated genes were present in all cases except where indicated. The NCBI v3.0 scaffold identifier from the bullfrog genome is indicated on the top left of each scaffold. Multiple scaffolds are indicated by a line break. Intronic regions are shown as thin lines that are spliced out in the labelled transcripts below the gene. The grey rectangles in the spliced transcript indicate the untranslated regions and the hatched rectangles indicate the open reading frame.

A 1.6 kbp two-exon gene gives rise to ranatuerin-1 and ranatuerin-1 (HP4) through alternative splicing (FIG. 6, Panel A) and a similar two-exon gene structure gives rise to ranatuerin-3RC and ranatuerin-3RC (HP8) through alternative splicing (FIG. 6, Panel B). In contrast, the three ranatuerins, ranatuerin-2PRc (HP2), ranatuerin-2RC, and ranatuerin-4, are each derived from distinct three-exon genes that are much larger (e.g. 15 kbp for ranatuerin-2PRc (HP2); see FIG. 7).

FIG. 7 shows the ranatuerin-2PRc (HP2), ranatuerin-2RC, and ranatuerin-4 genes are comprised of 3 exons. The structure of the genes and derived transcripts encoding Panel A—Ranatuerin-2PRc (HP2), Panel B—Ranatuerin-2RC, and Panel C—Ranatuerin-4 are shown. The illustrations are drawn to the indicated scale. The numbers in italics indicate the number of intervening base pairs where the intronic region was large. See FIG. 6 for more information.

FIG. 8 shows two genes, one with 3 exons and the other with 1 exon, encode Ranacyclins. The structure of the genes and derived transcripts encoding Panel A—Ranacyclin-Ca and Ranacyclin-Cc, and Panel B—Ranacyclin-Ca (HP3) are shown. The illustrations are drawn to the indicated scale. The numbers in italics indicate the number of intervening base pairs where the intronic region was large. Refer to FIG. 6 for more information. The dotted line in "A" indicates that the 5' end of the scaffold terminated prior to the available transcript information.

The transcripts encoding Ranacyclin-Ca and Ranacyclin-CC come from the same 3-exon gene whereas the gene encoding ranacyclin-Ca (HP3) is comprised of a single exon on a different scaffold (FIG. 8). A similar relationship occurs for Palustrin-Ca. Here, the palustrin-Ca transcript is derived from two exons (FIG. 8, Panel A) and palustrin-Ca (HP9) from a different single exon (FIG. 8, Panel B) from the same gene.

FIG. 9 shows Palustrin-Ca, encoded by a 2 exon gene, Palustrin-Ca (HP9) and HP5 are encoded by single exon genes. The structure of the genes and derived transcripts encoding Panel A—Palustrin-Ca; Panel B—Palustrin-Ca (HP9); and Panel C—HP5 are shown. The cartoons are illustrations to the indicated scale. The numbers in italics indicate the number of intervening base pairs where the intronic region was large. Refer to FIG. 6 for more information.

The gene encoding HP5 is comprised of a single exon (FIG. 9, Panel C). Finally, the leap2 and cathelicidin-AL transcripts are examples derived from the splicing of four exons (FIG. 10). The fact that all assembled transcript sequences above align with the independently-derived bullfrog genome with canonical splice sites further supports the legitimacy of the identified AMP transcript sequences.

FIG. 10 shows that both LEAP2 and Cathelicidin-AL are derived from four exons. The structure of the genes and derived transcripts encoding *R. catesbeiana* Panel A—LEAP2 and Panel B—Cathelicidin-AL, are shown. The illustrations are drawn to the indicated scale. The numbers in italics indicate the number of intervening base pairs where the intronic region was large. FIG. 6 provides additional information.

Discussion

By utilizing known sequence homology and structural characteristics of AMPs from empirically validated peptides, a bioinformatics approach was applied to an assembled bullfrog tadpole reference transcriptome, and identified transcripts encoding putative novel AMPs and augmented the sequence information available for known AMPs. Historically, frogs are a rich source of AMPs. However, studies on larval tadpole stages have been limited, particularly those pertaining to gene expression studies.

The present study focused on the premetamorphic tadpole as an organism that is primarily dependent upon the innate immune system for microbial protection. Similar to what was observed in the frog, tadpole tissues express several AMPs with the greatest concentration in the back skin. Previous work in *Xenopus laevis* indicated that transcripts encoding magainin and "peptide with amino terminal glycine and carboxy terminal leucinamide" (PGLa) are not detected until metamorphic climax and into the frog stage[34]. The abundance of these mRNAs increase in whole premetamorphic tadpoles by prolonged immersion in 5 nM $T_3$ for 7 d, inducing precocious metamorphosis[34]. Other studies established that mRNAs encoding Ranalexin in *R. catesbeiana*[35], Brevinin-1SY in *R. sylvatica*[36] and Preprotemporin in *R. ornativentris*[37] generally transition from undetectable or very low levels in the tadpole through thyroid hormone-dependent metamorphosis to high levels in the frog. An induction of Preprotemporin-encoding mRNA upon injection of adult *R. ornativentris* with $2\times10^{-9}$ M $T_3$ was observed[37]. The abundance levels of twenty known and putative AMP-encoding transcripts were examined, of which sixteen were expressed in at least one of the four premetamorphic tadpole tissues in the present study. The vast majority of AMP-encoding transcripts were not affected by $T_3$ treatment after 48 h and none was hormone-responsive in the back skin. It is difficult to compare the previous studies with the current results for multiple reasons: the use of whole tadpole homogenates rather than specific tissues and/or the use of adults instead of tadpoles for $T_3$ injection studies. It is possible that longer $T_3$ exposure times may result in modulation of more AMP-encoding transcripts, but this remains to be determined. The data suggest that the metamorphosis-dependent change in AMP expression may be a later indirect thyroid hormone-dependent response leading to a resetting of the innate immune system coinciding with life transition.

The antimicrobial properties of Catesbeianin-1, Ranacyclin-Ca, Ranatuerin-1, Ranatuerin-3RC, and Palustrin-Ca have been known for some time[6-8]. This example represents the discovery that there can be diversity in their prepro sequences while retaining the mature peptide sequence of the respective AMP as a consequence of alternative splicing. An intriguing possibility is that the gene splice variants may be developmentally regulated as part of resetting the immune system during postembryonic development. The consequence of this shift embodies a change in prepro sequence rather than the mature peptide of the respective AMP. This may have regulatory consequences for peptide localization, processing and/or activation that have yet to be determined, and may possibly reflect a developmental shift in expressed activating proteases as well[38]. Further examination into the expression profiles of the splice variants during development and in different tissues is warranted.

While considerable efforts have been placed on phylogenetic comparisons of AMPs at the protein level (for e.g.[39, 40]), much less is understood regarding the structure of the genes giving rise to AMP-encoding transcripts. The current study presents the first gene structure information of AMPs with known antimicrobial functionality in frogs, and it was found that a range of AMP gene structures were represented. The four-exon gene structure observed in R. catesbeiana cathelicidin is conserved with the human LL37 cathelicidin gene on chromosome 3 (NCBI Accession NM_004345.4) while the R. catesbeiana leap2 gene has four exons compared to three in fish and humans[41]. This apparent discrepancy may be due to the fourth exon comprised entirely of untranslated region (FIG. 10). As the R. catesbeiana leap2 gene structure is currently composed of two scaffolds, the possibility cannot be definitively discounted that the leap2 transcript may be an assembly artifact, but routine improvements to the bullfrog genome assembly will resolve this remote possibility.

The Ranatuerin-encoding genes are subject to alternative splicing and possess two or three exons in R. catesbeiana, and the close relationship between Ranatuerins and Ranacyclins are reflected in the retention of the three-exon gene structure. Further, the diversity of AMP mature peptide sequences have been suggested to be a consequence of gene duplications from an ancestral gene[41]. The present study provides support for this in addition to alternative splicing as another mechanism for AMP diversity.

Two new mature AMP sequence candidates, in addition to Ranatuerin-1, demonstrated antimicrobial activity against M. smegmatis. Of particular note, HP3 and the established AMP, Ranatuerin-1, exhibited similar antimicrobial activity against the mycobacterium, M. smegmatis. This species was used to establish that the novel AMPs described herein are active against Mycobacteria. Since all Mycobacterium species have a similar cellular structure, demonstrating activity against a classic non-pathogenic species has provided us the evidence that it is worthwhile to next assess the activity of the novel AMPs against pathogenic species in future experiments.

While there is some variability within the activity results presented herein, this Example clearly illustrate the process of designing optimized AMPs that exhibit improved consistency, reproducibility, stability, and enhanced activity[43]. Sequence analysis of the new AMP candidates revealed diversity within the prepro and the mature peptide sequences adding to the growing assortment of AMPs. The linkage of known AMP sequences to new prepro sequences opens up new possibilities for further AMP candidate discovery. Successful functional testing of AMPs identified via the bioinformatics methods used in the present study affirms the value of using a bioinformatics approach to mine the bullfrog genome, as described herein.

Because AMPs play a critical role in innate immunity[6,44], further examination of the circumstances of their expression and factors that may disrupt their normal function could inform conservation efforts. Amphibians are experiencing drastically decreased population numbers worldwide due to infectious pathogens[4,44]. The interplay between AMPs and pathogens is an important determinant of host survival upon infection, and some amphibian AMPs are known, for example, to kill the chytrid fungus, Batrachochytrium dendrobatidis[46,47]. Resistance can be conferred by fungal secretion of a protease that cleaves and disrupts amphibian AMP function[33] revealing the need for further investigations into the mechanisms of AMP regulation and their relationship to disease protection and pathogen evasion. In addition, continued investigations into the wealth of natural antibiotic compounds produced by amphibians will also undoubtedly result in further discovery of novel AMPs that may lead to the development of effective therapeutics for combatting the major and increasing global health threat of antibiotic resistance.

Sequence Availability

All biological sequences referenced herein by accession numbers, such as are available through NCBI, are hereby incorporated by reference as though the sequence was recited in its entirety within the subject text, figure, or tables.

Methods

Further details of the methods used herein are provided below. Citations are provided to indicate further details, and all references pertaining to methodologies used herein are hereby incorporated by reference.

In silico prediction and characterization of putative antimicrobial peptides. Seven novel AMP candidates were initially identified from the bullfrog annotated reference transcriptome (BART version 3, NCBI TSA accession GFBS01000000)[28,33] using the following three steps.

First, the BART transcript sequences, all of which were de novo assembled with Trans-ABySS[48] from strand-specific RNA-Seq libraries[28], were in silico translated using Transdecoder (-m 20-S; version 2.0.1) (github.com) and complete predicted open reading frames up to 100 amino acids long were retained.

Second, Hidden Markov models (HMMs) representing the salient features of AMPs from 35 protein families were downloaded from the Collection of Antimicrobial Peptides database (bicnirrh.res.in), and hmm[49] was used to identify BART peptide sequences with similarity to one or more HMM (default settings, significance considered at E<0.001).

These hits were then further refined using InterProScan[50] default settings with the Pfam database[51] of protein domain HMMs (version 29.0).

Third, candidate AMPs had to satisfy the following criteria: 1) the putative open reading frame began with a methionine or valine residue confirmed by Virtual Ribosome 2.052 analysis, and 2) the protein sequence contained a canonical propeptide convertase Lys-Arg (KR) cleavage site as determined by ExPASy Peptide Cutter (expasy.org). With the exception of one AMP candidate, all peptide sequences also had strong alignment to a known precursor AMP defined as an E-value score of $<10^{-4}$ using blastx or blastp against the NCBI nr database. If the candidate AMP sequence had a full precursor alignment to a sequence in the NCBI nr database with identity and positivity scores of greater than 90%, then the sequence was considered "known". A final set of seven "novel" and eleven "known" AMP-encoding R. catesbeiana transcripts were found from tadpole tissues (Table 2). An additional two AMP sequences that were already present in the NCBI nr database from previous studies on adult frogs were also examined in the present study (Table 2). Final protein alignments were generated using Clustal Omega version 1.4.2 (ebi.ac.uk)[53].

Secondary structures of the mature AMP peptides were assessed using SABLE Protein prediction (cchmc.org). The net charge, molecular weight, and isoelectric points (pI) of the mature peptides were determined using ExPASy ProtParam (expasy.org).

Gene expression analysis. The levels of twenty AMP-encoding R. catesbeiana transcripts (Table 2) were determined in premetamorphic R. catesbeiana tadpole back skin, tail fin, olfactory epithelium, and liver tissues through RNA-seq data derived from previous studies of tadpole tissues[28,33]. Strand-specific mRNA libraries were constructed and sequenced via Illumina HiSeq and aligned to the BART reference transcriptome[28] to generate counts. All RNA-seq experiments had comparable sequencing depth and were normalized to the total number of reads per sample. To normalize the counts, the number of reads were divided by the total number of reads in the corresponding sample and multiplied by 100 million.

Gene structure determination. The longest cDNA sequence from each of twenty R. catesbeiana transcripts encoding AMPs (Table 2) was used to query the high quality draft bullfrog genome (NCBI Accession number LIAG00000000, BioProject PRJNA285814)[28] using gmap version 2017 Apr. 13[54]. The relevant scaffolds are indicated in Table 2.

Microtiter broth dilution assays. To test for antimicrobial activity, HP3, HP4/Ranatuerin-1, and HP5, peptides were synthesized by GenScript (Piscataway, New Jersey, USA). HP2 was not tested because the service provider was unable to synthesize this peptide despite multiple attempts. An unrelated, similarly-sized peptide from the *Treponema pallidum* protein Tp0751[55] was used as a negative control and the human cathelicidin, LL-37[30], was included as a positive control. Peptides were dissolved in filter-sterilized ultrapure water and tested for sterility by plating on non-selective agar plates followed by a 48 h incubation at 37° C. Two-fold serial dilutions of each peptide were prepared to obtain a series corresponding to ten times the required testing concentrations (2560, 1280, 640, 320, 160, 80, 40, 20, 10, and 5 µg/mL)[29].

Microtiter broth dilution methods were implemented for determination of the minimum inhibitory concentration (MIC) and minimum bactericidal concentration (MBC) of the four putative AMPs and the negative control peptide using procedures adapted from the R.E.W. Hancock Laboratory for cationic AMPs[29] and the CLSI methods for dilution antimicrobial susceptibility tests[56].

To assess antimicrobial activity across a diverse range of bacterial species, colonies were cultured overnight on Mueller Hinton agar plates (MHA; +5% sheep blood for *S. pyogenes*)[56] from frozen glycerol stock. Bacteria tested include Gram-negative rods (*Escherichia coli*: ATCC 9723H; *Pseudomonas aeruginosa*: ATCC 10148), Gram-positive cocci (*Staphylococcus aureus*: ATCC 6538P; *Streptococcus pyogenes*: unknown strain, hospital isolate), and *Mycobacterium smegmatis* ($MC^2155$; classified as neither Gram-positive nor Gram-negative). Bacterial suspensions were prepared by placing 3-5 morphologically similar colonies from the grown plate into sterile glass culture tubes containing 2 mL of Mueller Hinton Broth (MHB; +5% lysed horse blood for *S. pyogenes*) 56. Microbial inoculums from bacterial suspensions were prepared through a spectrophotometric adjustment of turbidity to 0.08-0.1 at 600 nm to achieve a turbidity equivalent to that of a 0.5 McFarland standard ($1-2 \times 10^8$ CFU/mL)[29]. The standardized bacterial inoculums were then diluted in MHB to obtain final cell densities of approximately $5.0 \times 10^6$ CFU/mL.

Ninety-six-well microtiter plates (Fisher Cat. No. CS003790; Nepean, Ontario, Canada) were prepared with 100 µL of *E. coli, P. aeruginosa, S. aureus, S. pyogenes*, or *M. smegmatis* bacterial suspension ($5 \times 10^5$ CFU/mL) dispensed into each well of columns 1 through 11. Eleven microliters of the 10×AMP dilution series for all four peptides were added to each well from column 1 (2560 µg/mL) to column 10 (5 µg/mL) in all plates. Column 11 functioned as a positive control for bacterial growth in the absence of AMPs. Column 12 in each plate contained 100 µL of MHB as a sterility control (+5% lysed horse blood for *S. pyogenes*)[56]. Plates were incubated at 37° C. for 16-24 within 15 min of adding the inoculum.

MIC values were visually determined by comparing the amount of bacterial growth (turbidity) in wells containing AMPs with growth in the control wells that did not contain any amount of peptide. MBC values were determined by plating the entire contents of the wells containing the peptide/bacteria mixture representing the MIC and the entire contents of the two preceding wells containing 2-fold and 4-fold more concentrated AMP dilutions/bacteria mixtures onto non-selective MHA plates, followed by incubation for 24 h at 37° C.

Example 2

Antimicrobial Peptides

The following peptide sequences, located as described herein, may be used for antimicrobial applications as described. The peptides were prepared and tested as outlined below.

```
Group P1
                                              (SEQ ID NO: 66)
XXXPXXXXGGK (SEQ ID NO: 67)
FYFPXXXXGGK (SEQ ID NO: 68)
XYFXXSRKXXXX (SEQ ID NO: 69)
FXFXVSRKXXXX
```

-continued

```
                                     (SEQ ID NO: 70)
XYFXXXXKFXXK (SEQ ID NO: 71)
XXXXXXXXFGGK (SEQ ID NO: 72)
FYXPVXRXFXXX

Example sequence P1_CCH, 'natural'
                                     (SEQ ID NO: 35)
FYFPVSRKFGGK Example sequence P1_CCH_F9R_Y2P, 'synthetic'
                                     (SEQ ID NO: 36)
FPFPVSRKRGGK Group P2
                                     (SEQ ID NO: 73)
FFPRXXXXXXXFLPTXXXXXXXSVGN (SEQ ID NO: 74)
XXXXVLPLANKXXXXIYCXXXXXXXX (SEQ ID NO: 75)
FFPXXLPLANXXLPXXXXXLPXXVGN (SEQ ID NO: 76)
XXPRVLXXXXXXXXXXXXXXPKSXXX (SEQ ID NO: 77)
FXXXXXXXLANKXXXTIYCXXXXSVXX (SEQ ID NO: 78)
FFXXVLPXXXXXLXTXYCALPKXVXN (SEQ ID NO: 79)
XXXXXXXXLANXFXPXIXXALPKXXGX Example sequence P2_CCH, 'natural'
                                     (SEQ ID NO: 37)
FFPRVLPLANKFLPTIYCALPKSVGN Example sequence P2_CCH_T15K_P7R, 'synthetic'
                                     (SEQ ID NO: 38)
FFPRVLRLANKFLPKIYCALPKSVGN Group P3
                                     (SEQ ID NO: 80)
GLLXXXXXXXXXXXXXXXXXXXXXXXCPPSS (SEQ ID NO: 81)
XXXXXXXXXXXXKXXGXLMXXXXXXXMXGXXPPXS (SEQ ID NO: 82)
GLLXIIXXXGXTTGILMXXLXXXMXGXXPPXX (SEQ ID NO: 83)
XLXXXXXXXXXKXXXXXXXTLKCQMTXXCXXSS (SEQ ID NO: 84)
GLLXIIKXTGKTTGILMXXLKXXXXGXXXXXX (SEQ ID NO: 85)
GXLXIIKXTGXXTXIXMXTLKCQXTGRXPPSS (SEQ ID NO: 86)
GLLXXXXKXTGKXTXIXXXTLKXQXTGRXXXXX (SEQ ID NO: 87)
XXXXIIXXTXXTXGXLXXTXXCQXTXRXXXXX Example sequence P3_CCH, 'natural'
                                     (SEQ ID NO: 39)
GLLDIIKDTGKTTGILMDTLKCQMTGRCPPSS Example sequence P3_CCH_D8K_Q230, 'synthetic'
                                     (SEQ ID NO: 40)
GLLDIIKKTGKTTGILMDTLKCCMTGRCPPSS
```

```
Group P4
                                     (SEQ ID NO: 88)
GLLXIIXXXGXXXXXXILXXLXXXLAGGXXX (SEQ ID NO: 89)
GLLXXXKTTGKXFAVKILXNLXXXXXXXXPP (SEQ ID NO: 90)
XXXXIIKTXXXXFAVXXXXXXKCKLAGGXXX (SEQ ID NO: 91)
XXXXIIXXXXKXXXXKXXXNLKCKXXXXCPP (SEQ ID NO: 92)
GLLXXXKTTGXXXXXXXLXNLKCXXAXXCXX (SEQ ID NO: 93)
GLLXXXKXXXXFAVXXLXXLXXXXXXXXPP Example sequence P4_CCH, 'natural'
                                     (SEQ ID NO: 41)
GLLDIIKTTGKDFAVKILDNLKCKLAGGCPP Example sequence P4_CCH_P31K, 'synthetic'
                                     (SEQ ID NO: 42)
GLLDIIKTTGKDFAVKILDNLKCKLAGGCPK Group P5
                                     (SEQ ID NO: 94)
XXXXXXXLAAKXXXSLVXXXXKKC (SEQ ID NO: 95)
XFPIIAXLAAXVIPXLVXAVTXXX (SEQ ID NO: 96)
FFPXXAXXXXKXXPXXXXXXXXXX (SEQ ID NO: 97)
XXXXXXXLAAXVIPXLXXXXTXXX (SEQ ID NO: 98)
FFPIIAXXXXXXXXXXVCAVTKKC (SEQ ID NO: 99)
XXXIIXRXXXKVIXSXVCXVTKKC (SEQ ID NO: 100)
FFPIIARLAAXVIXSLXCAVXXXX Example sequence P5_CCH, 'natural'
                                     (SEQ ID NO: 43)
FFPIIARLAAKVIPSLVCAVTKKC Example sequence P5_CCH_A19K, 'synthetic'
                                     (SEQ ID NO: 44)
FFPIIARLAAKVIPSLVCKVTKKC Group P6
                                     (SEQ ID NO: 101)
GLWETIKXXXKXXXXXXXXXKXXXXXXXGGCPP (SEQ ID NO: 102)
XXXXXXXTTGXXXXXXXXXXXKCKXXXXCXX (SEQ ID NO: 103)
XXXXTIXXXGXXIALXLLXXIXXXIAXXXPP (SEQ ID NO: 104)
GLWETXKTTXXSXXLNLLDKIXXKIAXXXPP (SEQ ID NO: 105)
XXXXXIKXXGKSIALXXXXKXKXKXXGGXXX (SEQ ID NO: 106)
XXXXXXXXXXKSIAXNLLXXIXCXIAGGXXX Example sequence P6_CCH, 'natural'
                                     (SEQ ID NO: 45)
GLWETIKTTGKSIALNLLDKIKCKIAGGCPP
```

-continued

Example sequence P6_CCH_S12K, 'synthetic'
(SEQ ID NO: 46)
GLWETIKTTGKKIALNLLDKIKCKIAGGCPP Group P7
(SEQ ID NO: 107)
ATAWXIXXXGMXXIIXIXIXXLXGXX (SEQ ID NO: 108)
XXXWXIXXXGMQXXXXXXXXXXCGKQ (SEQ ID NO: 109)
XXXXXXPPPXXQPXXPXXXXPXXXXX (SEQ ID NO: 110)
ATAXXXPPPXXXPXXPXXXXPXCXKQ (SEQ ID NO: 111)
XXXWXIXXXGMXXXXXIXIXXLXGXX (SEQ ID NO: 112)
XXXXXXXXXXXXPXXPXXIXXLXGXX (SEQ ID NO: 113)
ATAXRXXXXXXQXIIXIRIRXLCXKQ Example sequence P7_CCH, 'natural'
(SEQ ID NO: 47)
ATAWRIPPPGMQPIIPIRIRPLCGKQ Example sequence P7_CCH_P9R_R5M, 'synthetic'
(SEQ ID NO: 48)
ATAWMIPPRGMQPIIPIRIRPLCGKQ Group P8
(SEQ ID NO: 114)
FPAIIXXXXXXX (SEQ ID NO: 115)
FXXXXCXXXKXC (SEQ ID NO: 116)
XXAIIXXVSKXX (SEQ ID NO: 117)
XPAXXCKXXXXX (SEQ ID NO: 118)
FPXXXXXVSKNC (SEQ ID NO: 119)
XXXIICKVSXNX Example sequence P8_CCH, 'natural'
(SEQ ID NO: 49)
FPAIICKVSKNC Example sequence P8_CCH_N11K, 'synthetic'
(SEQ ID NO: 50)
FPAIICKVSKKC Group P9
(SEQ ID NO: 120)
FLTFXGXXFGXXXGX (SEQ ID NO: 121)
XXXXPGMXFXXLLXX (SEQ ID NO: 122)
XXXXPGMXXXKXXXK (SEQ ID NO: 123)
FLTFXXXXXXXLLGX (SEQ ID NO: 124)
FXXFXXXTFGKXXXK (SEQ ID NO: 125)
XLTXXXXTFGKLLGK Example sequence P9_CCH, 'natural'
N/A Example sequence P9_CCH_2, 'synthetic'
(SEQ ID NO: 51)
FLTKPGMTFGKLLGK Group P10
(SEQ ID NO: 126)
XXXXFFXVNIFXLXX (SEQ ID NO: 127)
SNXXXXXVXXXRXXX (SEQ ID NO: 128)
XXXXFFXXXIFXLCG (SEQ ID NO: 129)
SNXXXXKXXXXXLCG (SEQ ID NO: 130)
XXRXXXKVNIFXXCX (SEQ ID NO: 131)
SXXXFFXVXIXXXXG (SEQ ID NO: 132)
SXRDFFKXNXXRXCX Example sequence P10_CCH, 'natural'
(SEQ ID NO: 52)
SNRDFFKVNIFRLCG Example sequence P10_CCH_2, 'synthetic'
(SEQ ID NO: 53)
SNRKFFKVRIFRLCG Group P11
(SEQ ID NO: 133)
XXXXXIQKXXXXXNTLKXXXKXXLXXX (SEQ ID NO: 134)
ALVAKXXXFPVFXXXXLCXLXXXXXX (SEQ ID NO: 135)
ALVAKIQKXXXXXXXXXXXKLXXXII (SEQ ID NO: 136)
XXXXXXXXKPXXNTLKXCKXEXEXX (SEQ ID NO: 137)
XXXXXXXQXFXVFXTLKLXKLXLXXX (SEQ ID NO: 138)
XLVAKIXXXPVXNXXXLXXXXLXII (SEQ ID NO: 139)
AXXXAXIXXFXXFXXXXXCXXEXEII Example sequence P11_CCH, 'natural'
(SEQ ID NO: 54)
ALVAKIQKFPVFNTLKLCKLELEII Example sequence P11_CCH_E21K_E23R, 'synthetic'
(SEQ ID NO: 55)
ALVAKIQKFPVFNTLKLCKLKLRII Group P12
(SEQ ID NO: 140)
XXGQVXXXXKXXX (SEQ ID NO: 141)
IAXXXAAAXXXXX (SEQ ID

```
                                                (SEQ ID NO: 143)
IXXQVXXXKQKHI (SEQ ID NO: 144)
XXXQVXXXXQXHI

Example sequence P12_CCH, 'natural'
                                                (SEQ ID NO: 56)
IAGQVAAAKQKHI Example sequence P12_CCH2, 'synthetic'
                                                (SEQ ID NO: 57)
IAGQKARAKQKHI Group P13
                                                (SEQ ID NO: 145)
XXRXPXXXXXKLWKXXLXXX (SEQ ID NO: 146)
IQXXXVXXXLXXXXLXXXII (SEQ ID NO: 147)
XXXLXXXNMXXXWKXXXXXX (SEQ ID NO: 148)
XXXLPXINMXKLXXXXLXXX Example sequence P13_CCH, 'natural'
                                                (SEQ ID NO: 58)
IQRLPVINMLKLWKLELEII Example sequence P13_CCH_N8K_E18K, 'synthetic'
                                                (SEQ ID NO: 59)
IQRLPVIKMLKLWKLELKII Group P14
                                                (SEQ ID NO: 149)
IQRLXXXXXXXXSLYXXXCRTC (SEQ ID NO: 150)
XXXLPVXVXLPSLYXXXXXXX (SEQ ID NO: 151)
IQRXXXIVIXXXXXXCVIXXXX (SEQ ID NO: 152)
XXXXPVXXXXPSLYXXXCRTC (SEQ ID NO: 153)
IQRLXVIXILXXXXCXXCXXC (SEQ ID NO: 154)
XXXLPXXXXXPXXXXVIXXTX (SEQ ID NO: 155)
XXXLXVIVILXSLYCVICRTC Example sequence P14_CCH, 'natural'
                                                (SEQ ID NO: 60)
IQRLPVIVILPSLYCVICRTC Example sequence P14_CCH_2, 'synthetic'
                                                (SEQ ID NO: 61)
IQRLPVIVILPSLYCVICRKK Group
                                                (SEQ ID NO: 156)
LXXPXPXYXFXXGIGXXXXWXXXWLNAQQMXXXXX (SEQ ID NO: 157)
XXCPTPXXXFXXXXXNHLXXXIIWLXXXXMXXXXX (SEQ ID NO: 158)
LRCXXXXXXXXENGXXXXXMWNXXXXXXXXXSYKNK (SEQ ID NO: 159)
XXXXTXHYNXENGIGNHLMXNXXXXXNXQXXXXKXX (SEQ ID NO: 160)
LXCXXXHXNXXXXXGNHXXWXXXWLXXXXMSXXNX (SEQ ID NO: 161)
XRXPXPHXXFXXXXXXXXXXIIXXXAXQXSYXXX Example sequence P15_CCH, 'natural'
                                                (SEQ ID NO: 62)
LRCPTPHYNFENGIGNHLMWNIIWLNAQQMSYKNK Example sequence P15_CCH_2, 'synthetic'
                                                (SEQ ID NO: 63)
LRCPTPHYRFENGIGNHLMWNIIWLNAQQMSYCNK Group P16
                                                (SEQ ID NO: 162)
SNRXXXMXXXXGLXGPXXIMXXXXX (SEQ ID NO: 163)
XXXXFFMXXXXXXCXXFGXXXXKXX (SEQ ID NO: 164)
SNRDXXXXXIFGLXGPXXIMXRKRR (SEQ ID NO: 165)
SXXXXXXXVNXXXXCXXFGXXEXXXX (SEQ ID NO: 166)
XXXXXXXXVNIFXXXXPXXXXXRXRR Example sequence P16_CCH, 'natural'
                                                (SEQ ID NO: 64)
SNRDFFMVNIFGLCGPFGIMERKRR Example sequence P16_CCH_2, 'synthetic'
                                                (SEQ ID NO: 65)
SNRKFFMVNIFGLCGPFGIMKRKRR
```

Methods

Peptides were tested for activity using as minimum inhibitory concentration (MIC), and minimum bactericidal concentration (MBC) determinations. For certain peptides, a hemolysis test was also conducted to determine $HC_{50}$ (µg/mL) as an indicator of hemolytic activity based on the concentration of an antimicrobial compound that kills 50% red blood cells.

Peptides were tested for activity against *E. coli*, *S. aureus*, *P. aeruginosa*, *S. pyogenes*, and *M. smegmatis*.

Independent experiments were conducted with four strains of *E. coli*, including ATCC *E. coli* (*Escherichia coli*—ATCC 25922 "wild type"); ESBL *E. coli* (*Escherichia coli*—Extended spectrum beta-lactamase); CPO *E. coli* (KPC) (*Escherichia coli*—Carbapenemase-producing organism; *Klebsiella pneumoniae* carbapenemase); and CPO *E. coli* (NDM) (*Escherichia coli*—Carbapenemase-producing organism; New-Dehli Metallobetalactamase).

Independent experiments were conducted with different strains of *Staphylococcus aureus*—ATCC 29213 "wild type"; and *Staphylococcus aureus*—Methicillin resistant *Staphylococcus aureus*.

The ATCC (American Type Culture Collection) strains received from Cedarlane. Multi drug resistant (MDR) strains, as clinical isolates, were received from the laboratory of Dr. Linda Hoang.

Putative antimicrobial peptides were synthesized by GeneScript. A-list antimicrobial peptides re-synthesized by GeneScript. P2_CCH, P5_CCH, and P5_CCH_A19K were each synthesized under two conditions: standard synthesis using TFA, and the other with TFA-removal using acetate as a counter-ion. A MIC method, adapted for use with cationic antimicrobial peptides, was used to evaluate MIC antimicrobial activity (Hancock 1999).

Results

MIC and MBC results are provided in the tables below. The units of concentration are µg/mL for MIC and MBC, unless otherwise noted.

TABLE 5

P1_CCH - MiC & MBC Results

| Peptide | P1_CCH | |
|---|---|---|
| | MIC (µg/mL) | MBC (µM/mL) |
| E. coli | >256 | >256 |
| S. aureus | >256 | >256 |
| P. aeruginosa | >256 | >256 |
| S. pyogenes | >256 | >256 |
| M. smegmatis | 256->256 | >256 |

TABLE 6

P2_CCH - MIC & MBC Results

| Peptide | P2_CCH | |
|---|---|---|
| | MIC | MBC |
| E. coli | 256->256 | 256->256 |
| S. aureus | >256 | >256 |
| P. aeruginosa | >256 | >256 |
| S. pyogenes | >256 | >256 |
| M. smegmatis | 16 | 64->256 |

TABLE 7

P3_CCH - MIC & MBC Results

| Peptide | P3_CCH | |
|---|---|---|
| | MIC | MBC |
| E. coli | >256 | >256 |
| S. aureus | >256 | >256 |
| P. aeruginosa | >256 | >256 |
| S. pyogenes | >256 | >256 |
| M. smegmatis | >256 | >256 |

TABLE 8

P4_CCH - MIC & MBC Results

| Peptide | P4_CCH | |
|---|---|---|
| | MIC | MBC |
| E. coli | 128 | 128 |
| S. aureus | >256 | >256 |
| P. aeruginosa | >256 | >256 |
| S. pyogenes | 256 | 256 |
| M. smegmatis | 8 | >256 |

TABLE 9

P5_CCH - MIC & MBC Results

| Peptide | P5_CCH | |
|---|---|---|
| | MIC | MBC |
| E. coli | 16 | 32 |
| S. aureus | 4 | 16 |
| P. aeruginosa | 256->256 | 256->256 |
| S. pyogenes | 128 | 128 |
| M. smegmatis | 2 | >256 |

TABLE 10

P6_CCH - MIC & MBC Results

| Peptide | P6_CCH | |
|---|---|---|
| | MIC | MBC |
| E. coli | 16-64 | 16-64 |
| S. aureus | 128-256 | 256 |
| P. aeruginosa | 256->256 | 256->256 |
| S. pyogenes | 128 | 128 |
| M. smegmatis | 2 | 2->256 |

TABLE 11

P7_CCH - MIC & MBC Results

| Peptide | P7_CCH | |
|---|---|---|
| | MIC | MBC |
| E. coli | >256 | >256 |
| S. aureus | >256 | >256 |
| P. aeruginosa | >256 | >256 |
| S. pyogenes | >256 | >256 |
| M. smegmatis | 32 | >256 |

TABLE 12

P8_CCH - MIC & MBC Results

| Peptide | P8_CCH | |
|---|---|---|
| | MIC | MBC |
| E. coli | >256 | >256 |
| S. aureus | >256 | >256 |
| P. aeruginosa | >256 | >256 |
| S. pyogenes | >256 | >256 |
| M. smegmatis | 128 | 128->256 |

TABLE 13

P9_CCH, P10_CCH, P11_CCH - MIC & MBC Results

| Peptide | P9_CCH | | P10_CCH | | P11_CCH | |
|---|---|---|---|---|---|---|
| | MIC | MBC | MIC | MBC | MIC | MBC |
| E. coli | >256 | >256 | >256 | >256 | >256 | >256 |
| S. aureus | >256 | >256 | >256 | >256 | >256 | >256 |
| P. aeruginosa | >256 | >256 | >256 | >256 | >256 | >256 |
| S. pyogenes | >256 | >256 | >256 | >256 | >256 | >256 |
| M. smegmatis | >256 | >256 | >256 | >256 | >256 | >256 |

TABLE 14

P12_CCH, P13_CCH, P14_CCH - MIC & MBC Results

| Peptide | P12_CCH MIC | P12_CCH MBC | P13_CCH MIC | P13_CCH MBC | P14_CCH MIC | P14_CCH MBC |
|---|---|---|---|---|---|---|
| *E. coli* | >256 | >256 | >256 | >256 | >256 | >256 |
| *S. aureus* | >256 | >256 | >256 | >256 | >256 | >256 |
| *P. aeruginosa* | >256 | >256 | >256 | >256 | >256 | >256 |
| *S. pyogenes* | >256 | >256 | >256 | >256 | >256 | >256 |
| *M. smegmatis* | >256 | >256 | >256 | >256 | >256 | >256 |

TABLE 15

P15_CCH and P16_CCH - MIC & MBC Results

| Peptide | P15_CCH MIC | P15_CCH MBC | P16_CCH MIC | P16_CCH MIC |
|---|---|---|---|---|
| *E. coli* | >256 | >256 | >256 | >256 |
| *S. aureus* | >256 | >256 | >256 | >256 |
| *P. aeruginosa* | >256 | >256 | >256 | >256 |
| *S. pyogenes* | >256 | >256 | >256 | >256 |
| *M. smegmatis* | >256 | >256 | >256 | >256 |

TABLE 16

H3, H4, H5 - MIC & MBC Results

| Peptide | H3 MIC | H3 MBC | H4 MIC | H4 MBC | H5 MIC | H5 MBC |
|---|---|---|---|---|---|---|
| *E. coli* | >256 | >256 | 128 | 128 | >256 | >256 |
| *S. aureus* | >256 | >256 | 256 | >256 | >256 | >256 |
| *P. aeruginosa* | >256 | >256 | >256 | >256 | >256 | >256 |
| *S. pyogenes* | >256 | >256 | >256 | >256 | >256 | >256 |
| *M. smegmatis* | 8 | >256 | 8 | >256 | 256 | >256 |

TABLE 17

R4 and R4_AcOH - MIC & MBC Results

| Peptide | R4 MIC | R4 MBC | R4_AcOH MIC | R4_AcOH MBC |
|---|---|---|---|---|
| *E. coli* | 16 | 16 | — | — |
| *S. aureus* | 4 | 4 | — | — |
| *P. aeruginosa* | >256 | >256 | >256 | >256 |
| *S. pyogenes* | — | — | — | — |
| *M. smegmatis* | 4 | 4 | — | — |

TABLE 18

LL37/Tp - MIC & MBC Results

| Peptide | LL37 +ve MIC | LL37 +ve MBC | LL37 +ve_AcOH MIC | LL37 +ve_AcOH MBC | Tp-ve MIC | Tp-ve MBC |
|---|---|---|---|---|---|---|
| *E. coli* | 64 | 64 | 64 | 64 | >256 | >256 |
| *S. aureus* | 256 | >256 | 256 | >256 | >256 | >256 |
| *P. aeruginosa* | 256->256 | 256->256 | >256 | >256 | >256 | >256 |
| *S. pyogenes* | >256 | >256 | — | — | >256 | >256 |
| *M. smegmatis* | 4 | 4->256 | 4 | 4 | >256 | >256 |

The following data are presented to show the activity (MIC/MBC in µg/mL) of certain antimicrobial peptides described herein relative to a modified/synthetic version having a specified substitution. While data presented in tables above may be presented again, or may be represented in data provided in the tables below, such duplication is believed to assist the reader in readily noting comparisons. Different Run Numbers noted in the following tables denotes experiments conducted on different days, with each run reflecting multiple n values.

TABLE 19

ATCC *E. coli* - MIC/MBC Analysis

| Peptide | # | Run No. 1 | 2 | 3 | 4 | 5 |
|---|---|---|---|---|---|---|
| P1_CCH | 1 | NI | | | | |
| P1_CCH_F9R_Y2P | 2 | NI | | | | |
| P2_CCH | 3 | 16/16 | NI | NI | 128/128 | 128/128 |
| P2_CCH_T15K_P7R | 4 | 4/4 | 4/4 | 4/4 | 8/8 | 8/8 |
| P3_CCH | 5 | NI | NI | NI | NI | NI |
| P3_CCH_D8K_Q23C | 6 | 64/64 | 64/64 | 64/64 | 64/64 | 64/64 |
| P4_CCH | 7 | 64/128 | 32/64 | 32/64 | 32/32 | 32/32 |
| P4_CCH_P31K | 8 | 32/32 | 32/32 | 16/32 | 16/32 | 16/32 |
| P5_CCH | 9 | 8/8 | 8/8 | 8/16 | 16/16 | 16/16 |
| P5_CCH_A19K | 10 | 16/16 | 4/4 | 4/4 | 4/4 | 4/4 |
| P6_CCH | 11 | 16/16 | 8/8 | 8/8 | 8/16 | 16/16 |
| P6_CCH_S12K | 12 | 4/4 | 4/4 | 4/4 | 4/4 | 4/4 |
| P7_CCH | 13 | NI | | | | |
| P7_CCH_P9R_R5M | 14 | 256 | | | | |
| P8_CCH | 15 | NI | | | | |
| P8_CCH_N11K | 16 | NI | | | | |
| P11_CCH | 17 | NI | NI | NI | NI | NI |
| P11_CCH_E21K_E23R | 18 | 32/32 | 64 | 64 | 64 | 64 |
| P13_CCH | 19 | NI | NI | NI | NI | NI |
| P13_CCH_N8K_E18K | 20 | 32 | NI | NI | NI | NI |
| HP1 | 21 | 2/2 | 4/4 | 4/4 | 4/4 | 4/4 |
| HP1delta7 | 22 | 8 | 16/16 | 16/16 | 16/16 | 16/16 |
| HP3 | 23 | NI | | | | |
| HP3_S3R | 24 | 128 | | | | |
| HP5 | 25 | NI | | | | |
| HP5_E10K_E14R | 26 | NI | | | | |
| LL37 positive | 27 | 8/8 | 8/8 | | 16/16 | 16/16 |
| P5_Tp Negative | 28 | NI | NI | | NI | NI |

TABLE 20

ESBL *E. coli* - MIC/MBC Analysis

| Peptide | Run No. 1 | 2 | 3 | 4 | 5 |
|---|---|---|---|---|---|
| P1_CCH | NI | | | | |
| P1_CCH_F9R_Y2P | NI | | | | |
| P2_CCH | 16/16 | 16/16 | 16/16 | 64/128 | 128/128 |
| P2_CCH_T15K_P7R | 2/2 | 4/4 | 4/4 | 8/8 | 8/8 |
| P3_CCH | NI | NI | NI | NI | NI |
| P3_CCH_D8K_Q23C | 64/64 | 64/64 | 64/64 | 64/128 | 64/128 |
| P4_CCH | 64/128 | 64/128 | 64/128 | 64/64 | 64/64 |
| P4_CCH_P31K | 32/32 | 32/32 | 32/32 | 32/32 | 32/32 |
| P5_CCH | 8/32 | 8/8 | 8/8 | 16/64 | 32/64 |
| P5_CCH_A19K | 16/16 | 16/16 | 16/16 | 8/8 | 4/4 |
| P6_CCH | 16/64 | 8/32 | 16/32 | 16/16 | 16/16 |
| P6_CCH_S12K | 4/4 | 4/4 | 4/4 | 4/4 | 4/4 |
| P7_CCH | NI | | | | |
| P7_CCH_P9R_R5M | 128/128 | | | | |
| P8_CCH | NI | | | | |
| P8_CCH_N11K | 128/128 | | | | |
| P11_CCH | NI | NI | NI | NI | NI |
| P11_CCH_E21K_E23R | 32/64 | 16 | 16 | 32/128 | 32/128 |
| P13_CCH | NI | NI | NI | NI | NI |
| P13_CCH_N8K_E18K | NI | NI | NI | NI | NI |
| HP1 | 8/8 | 4/4 | 4/4 | 4/4 | 4/4 |
| HP1delta7 | 32/32 | 32/32 | 32/32 | 64/128 | 64/128 |
| HP3 | NI | | | | |
| HP3_S3R | NI | | | | |
| HP5 | NI | | | | |

TABLE 20-continued

ESBL E. coli - MIC/MBC Analysis

| Peptide | Run No. 1 | 2 | 3 | 4 | 5 |
|---|---|---|---|---|---|
| HP5_E10K_E14R | NI | | | | |
| LL37 positive | 8/8 | 4/4 | | 8/8 | |
| P5_Tp Negative | NI | NI | | NI | |

TABLE 21

CPO E. coli (KPC) - MIC/MBC Analysis

| Peptide | Run No. 1 | 2 | 3 | 4 | 5 |
|---|---|---|---|---|---|
| P1_CCH | NI | | | | |
| P1_CCH_F9R_Y2P | NI | | | | |
| P2_CCH | 32/32 | 16/16 | 16/16 | 64/64 | 64/64 |
| P2_CCH_T15K_P7R | 8/8 | 8/8 | 8/8 | 8/8 | 8/8 |
| P3_CCH | NI | NI | NI | NI | NI |
| P3_CCH_D8K_Q23C | 64/128 | 128/128 | 128/128 | 64/64 | 64/64 |
| P4_CCH | 32/64 | 32/64 | 32/64 | NI | NI |
| P4_CCH_P31K | 32/32 | 16/32 | 16/32 | 16/32 | 16/32 |
| P5_CCH | 4/4 | 4/4 | 4/4 | 16/16 | 16/16 |
| P5_CCH_A19K | 16/16 | 16/16 | 16/16 | 4/4 | 4/4 |
| P6_CCH | 8/16 | 8/32 | 8/16 | 8/8 | 8/8 |
| P6_CCH_S12K | 4/8 | 4/4 | 4/4 | 4/4 | 4/4 |
| P7_CCH | NI | | | | |
| P7_CCH_P9R_R5M | 256/256 | | | | |
| P8_CCH | NI | | | | |
| P8_CCH_N11K | NI | | | | |
| P11_CCH | NI | NI | NI | NI | NI |
| P11_CCH_E21K_E23R | 64 | 32 | 32 | 32 | 32 |
| P13_CCH | NI | NI | NI | NI | NI |
| P13_CCH_N8K_E18K | 64 | 64 | 64 | NI | NI |
| HP1 | 8/8 | 4/4 | 4/16 | 4/4 | 4/4 |
| HP1delta7 | 16 | 16/32 | 16/64 | 32/32 | 32/32 |
| HP3 | NI | | | | |
| HP3_S3R | 256/256 | | | | |
| HP5 | NI | | | | |
| HP5_E10K_E14R | NI | | | | |
| LL37 positive | 16/16 | 16/16 | | 8/8 | |
| P5_Tp Negative | NI | NI | | NI | |

TABLE 22

CPO E. coli (NDM) - MIC/MBC Analysis

| Peptide | Run No. 1 | 22 | 3 | 4 | 5 |
|---|---|---|---|---|---|
| P1_CCH | NI | | | | |
| P1_CCH_F9R_Y2P | NI | | | | |
| P2_CCH | 16/16 | 16/16 | 16/16 | 128/128 | 128/128 |
| P2_CCH_T15K_P7R | 4/4 | 4/4 | 4/4 | 8/8 | 8/8 |
| P3_CCH | NI | NI | NI | NI | NI |
| P3_CCH_D8K_Q23C | 128/128 | 128/128 | 128/128 | 128/128 | NI |
| P4_CCH | 128/256 | 128/128 | 64/128 | 64/64 | 64/64 |
| P4_CCH_P31K | 32 | 32/32 | 32/32 | 64/64 | 32/64 |
| P5_CCH | 8/8 | 4/8 | 8/16 | 32/32 | 32/32 |
| P5_CCH_A19K | 16/16 | 16/16 | 16/16 | 8/8 | 4/4 |
| P6_CCH | 16/16 | 16/16 | 16/16 | 32/64 | 32/64 |
| P6_CCH_S12K | 4/4 | 4/8 | 4/8 | 8/8 | 8/8 |
| P7_CCH | 256 | | | | |
| P7_CCH_P9R_R5M | 256 | | | | |
| P8_CCH | NI | | | | |
| P8_CCH_N11K | 128/128 | | | | |
| P11_CCH | NI | NI | NI | NI | NI |
| P11_CCH_E21K_E23R | 32/128 | 32/128 | 32/128 | 64 | 64 |
| P13_CCH | 256 | NI | NI | NI | NI |
| P13_CCH_N8K_E18K | 128 | 64 | 64 | 64? | 64? |

TABLE 22-continued

CPO E. coli (NDM) - MIC/MBC Analysis

| Peptide | Run No. 1 | 22 | 3 | 4 | 5 |
|---|---|---|---|---|---|
| HP1 | 8/8 | 8/8 | 8/8 | 8/8 | 4/4 |
| HP1delta7 | 64/128 | 16/32 | 16/32 | 64/64 | 64/64 |
| HP3 | NI | | | | |
| HP3_S3R | 128 | | | | |
| HP5 | NI | | | | |
| HP5_E10K_E14R | NI | | | | |
| LL37 positive | 8/8 | 16/16 | | 8/8 | |
| P5_Tp Negative | 256/256 | NI | | NI | |

TABLE 23

ATCC S. aureus - MIC/MBC Analysis

| Peptide | Run No. 1 | 2 | 3 | 4 | 5 |
|---|---|---|---|---|---|
| P1_CCH | NI | | | | |
| P1_CCH_F9R_Y2P | NI | | | | |
| P2_CCH | NI | NI | NI | NI | NI |
| P2_CCH_T15K_P7R | 64/64 | 128/128 | 128/128 | 64/128 | 64/128 |
| P3_CCH | NI | NI | NI | NI | NI |
| P3_CCH_D8K_Q23C | NI | NI | NI | NI | NI |
| P4_CCH | NI | NI | NI | NI | NI |
| P4_CCH_P31K | NI | NI | NI | NI | NI |
| P5_CCH | 4/4 | 8/8 | 8/8 | 8/8 | 8/8 |
| P5_CCH_A19K | 8/8 | 2/2 | 2/2 | 2/2 | 2/2 |
| P6_CCH | 256 | 128 | 128 | NI | NI |
| P6_CCH_S12K | 64/64 | 64/64 | 64/64 | 128/128 | 128/128 |
| P7_CCH | NI | | | | |
| P7_CCH_P9R_R5M | 128 | | | | |
| P8_CCH | NI | | | | |
| P8_CCH_N11K | NI | | | | |
| P11_CCH | 64 | NI | NI | NI | NI |
| P11_CCH_E21K_E23R | 128 | NI | NI | NI | NI |
| P13_CCH | 128 | NI | NI | NI | NI |
| P13_CCH_N8K_E18K | 256 | NI | NI | NI | NI |
| HP1 | 4/8 | 4/4 | 4/4 | 4/4 | 4/4 |
| HP1delta7 | 8/16 | 32/32 | 32/32 | 32/32 | 32/32 |
| HP3 | NI | | | | |
| HP3_S3R | NI | | | | |
| HP5 | NI | | | | |
| HP5_E10K_E14R | NI | | | | |
| LL37 positive | 128 | 128 | | NI | NI |
| P5_Tp Negative | NI | NI | | NI | NI |

TABLE 24

MRSA - MIC/MBC Analysis

| Peptide | Run No. 1 | 2 | 3 | 4 | 5 |
|---|---|---|---|---|---|
| P1_CCH | NI | | | | |
| P1_CCH_F9R_Y2P | NI | | | | |
| P2_CCH | NI | NI | NI | NI | NI |
| P2_CCH_T15K_P7R | 64/64 | 32/32 | 64/64 | 32/32 | 32/32 |
| P3_CCH | NI | NI | NI | | |
| P3_CCH_D8K_Q23C | NI | NI | NI | | |
| P4_CCH | NI | NI | NI | | |
| P4_CCH_P31K | NI | NI | NI | | |
| P5_CCH | 2/2 | 2/2 | 4/4 | 8/8 | 4/4 |
| P5_CCH_A19K | 8/8 | 8/8 | 8/8 | 2/2 | 2/2 |
| P6_CCH | 256/256 | 256/256 | 256/256 | 128 | 128 |
| P6_CCH_S12K | 128/128 | 64/64 | 64/128 | 64/64 | 64/64 |
| P7_CCH | NI | | | | |
| P7_CCH_P9R_R5M | NI | | | | |
| P8_CCH | NI | | | | |

TABLE 24-continued

MRSA - MIC/MBC Analysis

| Peptide | Run No. 1 | 2 | 3 | 4 | 5 |
|---|---|---|---|---|---|
| P8_CCH_N11K | NI | | | | |
| P11_CCH | NI | NI | NI | NI | NI |
| P11_CCH_E21K_E23R | NI | NI | NI | NI | NI |
| P13_CCH | NI | NI | NI | NI | NI |
| P13_CCH_N8K_E18K | NI | NI | NI | NI | NI |
| HP1 | 4/4 | 2/2 | 4/4 | 4/8 | 4/8 |
| HP1delta7 | 8 | 8/8 | 8/8 | 16/64 | 16/16 |
| HP3 | NI | | | | |
| HP3_S3R | NI | | | | |
| HP5 | NI | | | | |
| HP5_E10K_E14R | NI | | | | |
| LL37 positive | 256 | NI | | NI | NI |
| P5_Tp Negative | NI | NI | | NI | NI |

TABLE 25

Salmonella Enteritidis - MIC/MBC Analysis

| Peptide | Run No. 1 | 2 | 3 | 4 | 5 |
|---|---|---|---|---|---|
| P1_CCH | NI | | | | |
| P1_CCH_F9R_Y2P | NI | | | | |
| P2_CCH | 64/64 | NI | NI | NI | NI |
| P2_CCH_T15K_P7R | 32/32 | 64/64 | 64/64 | 32/128 | 32/128 |
| P3_CCH | NI | NI | NI | NI | NI |
| P3_CCH_D8K_Q23C | NI | NI | NI | NI | NI |
| P4_CCH | NI | NI | NI | NI | NI |
| P4_CCH_P31K | 256/256 | NI | NI | NI | NI |
| P5_CCH | 64/64 | 128/128 | 128/128 | 128/128 | 128/128 |
| P5_CCH_A19K | 64/64 | 16/16 | 32/32 | 16/16 | 16/16 |
| P6_CCH | 128/128 | 64/64 | 64/64 | 64/128 | 128/128 |
| P6_CCH_S12K | 16/16 | 32/32 | 32/32 | 32/32 | 16/32 |
| P7_CCH | NI | | | | |
| P7_CCH_P9R_R5M | NI | | | | |
| P8_CCH | NI | | | | |
| P8_CCH_N11K | NI | | | | |
| P11_CCH | 32 | 32 | 32 | NI | NI |
| P11_CCH_E21K_E23R | 64 | NI | NI | NI | NI |
| P13_CCH | 16 | 16 | 16 | NI | NI |
| P13_CCH_N8K_E18K | 16 | 16 | 16 | NI | NI |
| HP1 | 32 | 32/32 | 16/16 | 16/16 | 16/16 |
| HP1delta7 | 256 | NI | NI | NI | NI |
| HP3 | NI | | | | |
| HP3_S3R | NI | | | | |
| HP5 | NI | | | | |
| HP5_E10K_E14R | NI | | | | |
| LL37 positive | NI | 128 | | 64/64 | 64/64 |
| P5_Tp Negative | NI | NI | | NI | NI |

TABLE 26

Salmonella Heidelberg (MDR) - MIC/MBC Analysis

| Peptide | Run No. 1 | 2 | 3 | 4 | 5 |
|---|---|---|---|---|---|
| P1_CCH | NI | | | | |
| P1_CCH_F9R_Y2P | NI | | | | |
| P2_CCH | 128/128 | NI | NI | NI | NI |
| P2_CCH_T15K_P7R | 16/16 | 64/64 | 32/64 | 64/64 | 32/64 |
| P3_CCH | NI | NI | NI | NI | NI |
| P3_CCH_D8K_Q23C | 256 | NI | NI | NI | NI |
| P4_CCH | 256 | NI | NI | NI | NI |
| P4_CCH_P31K | 128 | 128 | 128 | NI | NI |
| P5_CCH | 32/64 | 128/128 | 128/128 | 128/128 | 128/128 |
| P5_CCH_A19K | 64/64 | 16/16 | 16/16 | 16/16 | 16/16 |
| P6_CCH | 64/256 | 64/64 | 64/64 | 64/64 | 64/64 |
| P6_CCH_S12K | 32/64 | 32/32 | 16/64 | 16/32 | 16/32 |
| P7_CCH | NI | | | | |
| P7_CCH_P9R_R5M | NI | | | | |
| P8_CCH | NI | | | | |
| P8_CCH_N11K | NI | | | | |
| P11_CCH | 128 | NI | NI | NI | NI |
| P11_CCH_E21K_E23R | 128 | NI | NI | NI | NI |
| P13_CCH | 32 | 32? | 32? | NI | NI |
| P13_CCH_N8K_E18K | 32 | 16? | 16? | NI | NI |
| HP1 | 32/32 | 16/16 | 32/32 | 16/16 | 16/16 |
| HP1delta7 | 128 | 128 | 128 | 128 | 128 |
| HP3 | NI | | | | |
| HP3_S3R | NI | | | | |
| HP5 | NI | | | | |
| HP5_E10K_E14R | NI | | | | |
| LL37 positive | NI | NI | | 128 | NI |
| P5_Tp Negative | NI | NI | | | |

Table 27 shows the activity testing of select peptides described herein, for the metrics of Minimum Inhibitory Concentration (MIC) as well as by hemolysis testing to determine $HC_{50}$ (μg/mL) as an indicator of hemolytic activity based on the concentration of an antimicrobial compound that kills 50% red blood cells using standard methodology. In Table 27, the designations P2, P2M, P3, P3M, P4, P4M, P5, P5M, P6, and P6M refer to peptides P2_CCH, P2_CCH_T15K_P7R, P3_CCH, P3_CCH_D8K_Q23C, P4_CCH, P4_CCH_P31K, P5_CCH, P5_CCH_A19K, P6_CCH, and P6_CCH_S12K, respectively, as defined above.

TABLE 27

Select Activity Parameters for AMPs

Activity Test: Minimum Inhibitory Concentration (MIC) (ug/mL)

| Bacterial Isolate | P2 | P2M | P3 | P3M | P4 | P4M | P5 | P5M | P6 | P6M | Ran-4 | Ran-4M | LL37 (+ve) | Tp_P5 (−ve) |
|---|---|---|---|---|---|---|---|---|---|---|---|---|---|---|
| Gram negative | | | | | | | | | | | | | | |
| E. coli ATCC 25922 | 16 | 4-8 | — | 64 | 32-64 | 16-32 | 4-16 | 4-16 | 8-16 | 4 | 2-4 | 8-16 | 8-16 | — |
| ESBL E. coli | 16 | 2-8 | — | 64 | 64 | 32 | 8-32 | 4-16 | 8-16 | 4 | 4-8 | 32-64 | 4-8 | — |
| CPO E. coli NDM | 16 | 4-8 | — | 128+ | 64-128 | 32-64 | 4-32 | 4-16 | 16-32 | 4-8 | 4-8 | 16-64 | 8-16 | — |
| CPO E. coli KPC | 16-32 | 8 | — | 64-128 | 32 | 16-32 | 4-16 | 4-16 | 8 | 4 | 4-8 | 16-32 | 8-16 | — |

TABLE 27-continued

Select Activity Parameters for AMPs

| Activity Test | | | | | | | | Minimum Inhibitory Concentration (MIC) (ug/mL) | | | | | | |
|---|---|---|---|---|---|---|---|---|---|---|---|---|---|---|
| S. enterica spp. Enteritidis | 64 | 32-64 | — | — | — | — | 64-128 | 16-64 | 64-128 | 16-32 | 16-32 | — | 64+ | — |
| S. enterica spp. Heidelberg | 128 | 16-64 | — | — | — | 128+ | 32-128 | 16-64 | 64 | 16-32 | 16-32 | 128 | — | — |
| Gram positive | | | | | | | | | | | | | | |
| S. aureus ATCC 29213 | — | 64-128 | — | — | — | — | 4-8 | 2-8 | 128+ | 64-128 | 64-128 | 8-23 | 128+ | — |
| MRSA | — | 32-64 | — | — | — | — | 2-8 | 2-8 | 128+ | 64-128 | 64-128 | 8-16 | — | — |

| Hemolysis Test | P2 | P2M | P3 | P3M | P4 | P4M | P5 | P5M | P6 | P6M | Ran-4 | Ran-4M | LL37 (+ve) | Tp_P5 (−ve) |
|---|---|---|---|---|---|---|---|---|---|---|---|---|---|---|
| HC$_{50}$ (ug/mL)—1X PBS | — | — | — | — | — | — | 128 | — | — | — | 128 | — | — | — |
| HC$_{50}$ (ug/mL)—RPMI | — | 64 | — | — | — | — | 8-64 | 64-128 | — | — | 16-64 | — | — | — |

Table 28 provides an overview of the sequences described herein, and the counterpart SEQ ID NOs. Where 'X' is shown in the sequence listing, it is the equal of the three-letter code "Xaa", meaning that any sequence may be present. Where tables or figures illustrating alignments may show a dash "-", this indicates an absent residue, in place to maintain the best alignment possible with the comparable sequences shown. Unless otherwise specified, sequences are synthetic and/or derived from Bullfrog Annotated Reference Transcriptome (BART) of the North American bullfrog, *Rana* (*Lithobates*) *catesbeiana*. Synthetic peptides, and/or are isolated sequences.

TABLE 28

Sequences described herein and corresponding SEQ ID NOs

| Table/FIG. | SEQ ID NO |
|---|---|
| Table 1 | SEQ ID NO: 1-14 are provided below.<br>SEQ ID NO: 1 is:<br>MFTMKKSLLLLFFLGTISLSLCEQERNADDDQGEVIEQKVKR<br>SEQ ID NO: 2 is:<br>AFLSTVKNTLINVAGTMIDIFKCKITGVC<br>SEQ ID NO: 3 is:<br>VLLYLIITVSFPRRDANDEDGGEVIKEVVKR<br>SEQ ID NO: 4 is:<br>SLSGCWTKSFPRKPCLRNR<br>SEQ ID NO: 5 is:<br>MSSFCEITNVALTISLSSPRRGADEEEGNGEKEIKR<br>SEQ ID NO: 6 is:<br>SMLSVLKNLGKVGLGFVACKINKQC<br>SEQ ID NO: 7 is:<br>MIQSTQKWFKIKYWRVRNRPAMSPDLNPIEHLWRDLKKVVGKR<br>SEQ ID NO: 8 is:<br>NPSNLRALEELVKEECSEIPVERCKKLIYGYRK<br>SEQ ID NO: 9 is:<br>MRKRMTMRRMMKKKKSEKERRERGKR<br>SEQ ID NO: 10 is:<br>MMRVMRRKTKVIWEKKDFIGLYSID<br>SEQ ID NO: 11 is:<br>MFFMSSPRRDADEVKEVKR<br>SEQ ID NO: 12 is:<br>GFLDIIKNLGKTFAGHMLDKIKCTIGTCPPSP<br>SEQ ID NO: 13 is:<br>MITVSSPRRDADGDEGEVEEVKR<br>SEQ ID NO: 14 is:<br>GFLDIIKDIGKEFAVKILNNLKCKLAGGCPP |
| FIG. 1 | SEQ ID NO: 15-30 are provided below.<br>SEQ ID NO: 15 is:<br>MFTMKKSLLLFFFLGTISLSLCEEERDADDDQGEVVKKEVKR<br>AFFTIVKNLVINVAGTVIDKMKCCKLIGQC<br>SEQ ID NO: 16 is:<br>MFTMKKSLLLLFFLGTISLSLCEQERNADDDQGEVIEQKVKR<br>AFLSTVKNTLINVAGTMIDIFKCKITGVC<br>SEQ ID NO: 17 is:<br>MFTLKKSLLLLFFLGTITLSLCEQERGADEEEGNGEKEIKR<br>SMLSVLKNLGKVGLGFVACKINKQC<br>SEQ ID NO: 18 is:<br>MSSFCEITNVALTISLSSPRRGADEEEGNGEKEIKR<br>SMLSVLKNLGKVGLGFVACKINKQC<br>SEQ ID NO: 19 is:<br>MFFMSSPRRDADEVKEVKR<br>GFLDIIKNLGKTFAGHMLDKIKCTIGTCPPSP |

TABLE 28 -continued

Sequences described herein and corresponding SEQ ID NOs

| Table/FIG. | SEQ ID NO |
|---|---|
| | SEQ ID NO: 20 is:<br>MFTMKKSLLLLFFLGTISLSLCEPQRDADEVKEVKR<br>GFLDIIKNLGKTFAGHMLDKIKCTIGTCPPSP<br>SEQ ID NO: 21 is:<br>MFTLKKSLLLLFFLGTINLSLCEEERDAEEERRDNPDERDVEVEKR<br>FLPFIARLAAKVFPSIICSVIKKC<br>SEQ ID NO: 22 is:<br>MFTMKKSLLLLFFLGTISLSLCEQERNADDDQGEVIEQKVKR<br>AFLSTVKNTLINVAGTMIDIFKCKITGVC<br>SEQ ID NO: 23 is:<br>MFTLKKSLLLLFFLGTITLSLCEQERGADEDNGGEMTEEEVKR<br>GLFLDTLKGAAKDVAGKLLEGLKCKITGCKP<br>SEQ ID NO: 24 is:<br>MFTMKKSLLLLFFLGIISLSLCEQERDANDEEDGGEVTKEVVKR<br>SLRGCWIKSFPPQPCLGKRLNMN<br>SEQ ID NO: 25 is:<br>MFILKKSLLLLFFFGIISLSFCEQERDANDEEDGGEVIKEVVKR<br>SLRGCWTKSYPPQPCLGKR<br>SEQ ID NO: 26 is:<br>VLLYLIITVSFPRRDANDEDGGEVIKEVVKR<br>SLSGCWTKSFPRKPCLRNR<br>SEQ ID NO: 27 is:<br>MFTMKKSEKERRERGKR<br>MMRVMRRKTKVIWEKKDFIGLYSID<br>SEQ ID NO: 28 is:<br>MRKRMTMRRMMKKKKSEKERRERGKR<br>MMRVMRRKTKVIWEKKDFIGLYSID<br>SEQ ID NO: 29 is:<br>MFTMKKSLLLLFFLGTISLSLCEQERDADGDEGEVEEVKR<br>GFLDIIKDIGKEFAVKILNNLKCKLAGGCPP<br>SEQ ID NO: 30 is:<br>MITVSSPRRDADGDEGEVEEVKR<br>GFLDIIKDIGKEFAVKILNNLKCKLAGGCPP |
| FIG. 4 | SEQ ID NO: 31-34 are provided below.<br>SEQ ID NO: 31 is:<br>MGLSATLWFLMGVAAGSMASPLLQWSEDDISVMALYSTDYYNKVS<br>GEDVLYGLQENNTEYITDEKSRFHQLSFPIQKTVCQKSDNALTDD<br>CAFKEGGVVKSCTSYFFEEDDRDIIVVICQSQDGHREHSRVRRSR<br>RGRGGGRRGGSGGRGGRGGGGRSGAGSSIAGVGSRGGGGRH̲Y̲A̲<br>SEQ ID NO: 32 is:<br>MGLSATFWFLMGLAASSMASPLLQWSEDDAAVMALYSADHYNKV<br>SGEDVLYGLLENDTEYITDEKSRFHQLSFPIQETVCQKSDNNAP<br>TDDCAFKEGGVVKSCTSYFFEEDDRDIVVVNCQSQDSHREHSRV<br>RRSRSGRGGGGRGGGGRGGSRGGSRSGSRSSIAGGGSRGGSRGG<br>G̲T̲RYA<br>SEQ ID NO: 33 is:<br>MIPQLRKWMAIFVMCIVLIHQLEGAPMNSNDGSKTALRLRR<br>M̲T̲P̲F̲W̲R̲G̲L̲S̲L̲R̲P̲V̲G̲A̲S̲C̲R̲D̲D̲T̲E̲C̲L̲I̲R̲L̲C̲R̲N̲Q̲R̲C̲S̲L̲K̲T̲F̲A̲D̲<br>SEQ ID NO: 34 is:<br>MTPQLRKWTAIFVICIVLIHQLEGAPMSNTAGSKTLLRLRRR<br>M̲T̲P̲F̲W̲R̲G̲L̲S̲L̲R̲P̲V̲G̲A̲S̲C̲R̲D̲D̲T̲E̲C̲L̲I̲R̲L̲C̲R̲K̲E̲R̲C̲S̲L̲K̲T̲F̲A̲D̲ |
| P1 to P16 "natural" and "synthetic" example sequences | SEQ ID NO: 35-65 are provided below.<br>SEQ ID NO: 35 is: FYFPVSRKFGGK<br>SEQ ID NO: 36 is: FPFPVSRKRGGK<br>SEQ ID NO: 37 is:<br>FFPRVLPLANKFLPTIYCALPKSVGN<br>SEQ ID NO: 38 is:<br>FFPRVLRLANKFLPKIYCALPKSVGN<br>SEQ ID NO: 39 is:<br>GLLDIIKDIGKITGILMDTLKCQMTGRCPPSS<br>SEQ ID NO: 40 is:<br>GLLDIIKKIGKITGILMDTLKCCMTGRCPPSS<br>SEQ ID NO: 41 is:<br>GLLDIIKTTGKDFAVKILDNLKCKLAGGCPP<br>SEQ ID NO: 42 is:<br>GLLDIIKTTGKDFAVKILDNLKCKLAGGCPK<br>SEQ ID NO: 43 is:<br>FFPIIARLAAKVIPSLVCAVTKKC<br>SEQ ID NO: 44 is:<br>FFPIIARLAAKVIPSLVCKVTKKC<br>SEQ ID NO: 45 is:<br>GLWETIKTTGKSIALNLLDKIKCKIAGGCPP<br>SEQ ID NO: 46 is:<br>GLWETIKTTGKKIALNLLDKIKCKIAGGCPP |

TABLE 28 -continued

Sequences described herein and corresponding SEQ ID NOs

| Table/FIG. | SEQ ID NO |
|---|---|
| | SEQ ID NO: 47 is: ATAWRIPPPGMQPIIPIRIRPLCGKQ |
| | SEQ ID NO: 48 is: ATAWMIPPRGMQPIIPIRIRPLCGKQ |
| | SEQ ID NO: 49 is: FPAIICKVSKNC |
| | SEQ ID NO: 50 is: FPAIICKVSKKC |
| | SEQ ID NO: 51 is: FLTKPGMTFGKLLGK |
| | SEQ ID NO: 52 is: SNRDFFKVNIFRLCG |
| | SEQ ID NO: 53 is: SNRKFFKVRIFRLCG |
| | SEQ ID NO: 54 is: ALVAKIQKFPVFNTLKLCKLELEII |
| | SEQ ID NO: 55 is: ALVAKIQKFPVFNTLKLCKLKLRII |
| | SEQ ID NO: 56 is: IAGQVAAAKQKHI |
| | SEQ ID NO: 57 is: IAGQKARAKQKHI |
| | SEQ ID NO: 58 is: IQRLPVINMLKLWKLELEII |
| | SEQ ID NO: 59 is: IQRLPVIKMLKLWKLELKII |
| | SEQ ID NO: 60 is: IQRLPVIVILPSLYCVICRTC |
| | SEQ ID NO: 61 is: IQRLPVIVILPSLYCVICRKK |
| | SEQ ID NO: 62 is: LRCPTPHYNFENGIGNHLMWNIIWLNAQQMSYKNK |
| | SEQ ID NO: 63 is: LRCPTPHYRFENGIGNHLMWNIIWLNAQQMSYCNK |
| | SEQ ID NO: 64 is: SNRDFFMVNIFGLCGPFGIMERKRR |
| | SEQ ID NO: 65 is: SNRKFFMVNIFGLCGPFGIMKRKRR |
| Group P1-Group P16 variant sequences | SEQ ID NO: 66-166 are provided below<br>XXXPXXXXXGGK (SEQ ID NO: 66)<br>FYFPXXXXXGGK (SEQ ID NO: 67)<br>XYFXXSRKXXXX (SEQ ID NO: 68)<br>FXFXVSRKXXXX (SEQ ID NO: 69)<br>XYFXXXXKFXXK (SEQ ID NO: 70)<br>XXXXXXXXFGGK (SEQ ID NO: 71)<br>FYXPVXRXFXXX (SEQ ID NO: 72)<br>FFPRXXXXXXXXFLPTXXXXXXXSVGN (SEQ ID NO: 73)<br>XXXXVLPLANKXXXXIYCXXXXXXXX (SEQ ID NO: 74)<br>FFPXXLPLANXXLPXXXXXLPXXVGN (SEQ ID NO: 75)<br>XXPRVLXXXXXXXXXXXXXXPKSXXX (SEQ ID NO: 76)<br>FXXXXXXXLANKXXXTIYCXXXXSVXX (SEQ ID NO: 77)<br>FFXXVLPXXXXXLXTXYCALPKXVXN (SEQ ID NO: 78)<br>XXXXXXXXLANXFXPXIXXALPKXXGX (SEQ ID NO: 79)<br>GLLXXXXXXXXXXXXXXXXXXXXXXXCPPSS (SEQ ID NO: 80)<br>XXXXXXXKXXXKXXGXLMXXXXXXMXGXXPPXS (SEQ ID NO: 81)<br>GLLXIIXXXGXTTGILMXXLXXXMXGXXPPXX (SEQ ID NO: 82)<br>XLXXXXXXXXXKXXXXXXXTLKCQMTXXCXXSS (SEQ ID NO: 83)<br>GLLXIIKXIGKITGILMXXLKXXXXGXXXXXX (SEQ ID NO: 84)<br>GXLXIIKXTGXXIXIXMXTLKCQXTGRXPPSS (SEQ ID NO: 85)<br>GLLXXXKXIGKXIXIXXXILKXQXTGRXXXXX (SEQ ID NO: 86)<br>XXXXIIXXTXXIXGXLXXTXXCQXTXRXXXXX (SEQ ID NO: 87)<br>GLLXIIXXXGXXXXXXILXXLXXXLAGGXXX (SEQ ID NO: 88)<br>GLLXXXXKTIGKXFAVKILXNLXXXXXXXXPP (SEQ ID NO: 89)<br>XXXXIIKTXXXXFAVXXXXXXKCKLAGGXXX (SEQ ID NO: 90)<br>XXXXIIXXXXKXXXXKXXXNLKCKXXXXCPP (SEQ ID NO: 91)<br>GLLXXXKTTGXXXXXXXLXNLKCXXAXXCXX (SEQ ID NO: 92)<br>GLLXXXKXXXXXFAVXXLXXLXXXXXXXXPP (SEQ ID NO: 93)<br>XXXXXXXLAAKXXXSLVXXXXKKC (SEQ ID NO: 94)<br>XFPIIAXLAAXVIPXLVXAVTXXX (SEQ ID NO: 95)<br>FFPXXAXXXXKXXPXXXXXXXXXX (SEQ ID NO: 96)<br>XXXXXXXLAAXVIPXLXXXXTXXX (SEQ ID NO: 97)<br>FFPIIAXXXXXXXXXXVCAVTKKC (SEQ ID NO: 98)<br>XXXIIXRXXXKVIXSXVCXVTKKC (SEQ ID NO: 99)<br>FFPIIARLAAXVIXSLXCAVXXXX (SEQ ID NO: 100)<br>GLWETIKXXXKXXXXXXXXXXXXXXXGGCPP (SEQ ID NO: 101)<br>XXXXXXXTTGXXXXXXXXXXXKCKXXXXCXX (SEQ ID NO: 102)<br>XXXXTIXXXGXXIALXLLXXIXXXIAXXXPP (SEQ ID NO: 103)<br>GLWETXKITXXSXXLNLLDKIXXKIAXXXPP (SEQ ID NO: 104)<br>XXXXXIKXXGKSIALXXXXXKXKXXGGXXX (SEQ ID NO: 105)<br>XXXXXXXXXXKSIAXNLLXXIXCXIAGGXXX (SEQ ID NO: 106)<br>ATAWXIXXXGMXXIIXIXIXXLXGXX (SEQ ID NO: 107)<br>XXXWXIXXXGMQXXXXXXXXXXCGKQ (SEQ ID NO: 108)<br>XXXXXPPPXXQPXXPXXXXPXXXXX (SEQ ID NO: 109)<br>ATAXXPPPXXXPXXPXXXXPXCXKQ (SEQ ID NO: 110)<br>XXXWXIXXXGMXXXXIXIXXLXGXX (SEQ ID NO: 111)<br>XXXXXXXXXXXPXXPXXIXXLXGXX (SEQ ID NO: 112)<br>ATAXRXXXXXXQXIIXIRIRXLCXKQ (SEQ ID NO: 113)<br>FPAIIXXXXXXX (SEQ ID NO: 114)<br>FXXXXCXXXKXC (SEQ ID NO: 115)<br>XXAIIXXVSKXX (SEQ ID NO: 116) |

TABLE 28-continued

Sequences described herein and corresponding SEQ ID NOs

| Table/FIG. | SEQ ID NO |
|---|---|
| | XPAXXCKXXXXX (SEQ ID NO: 117) |
| | FPXXXXXVSKNC (SEQ ID NO: 118) |
| | XXXIICKVSXNX (SEQ ID NO: 119) |
| | FLTFXGXXFGXXXGX (SEQ ID NO: 120) |
| | XXXXPGMXFXXLLXX (SEQ ID NO: 121) |
| | XXXXPGMXXXKXXXK (SEQ ID NO: 122) |
| | FLTFXXXXXXXLLGX (SEQ ID NO: 123) |
| | FXXFXXXTFGKXXXK (SEQ ID NO: 124) |
| | XLTXXXXTFGKLLGK (SEQ ID NO: 125) |
| | XXXXFFXVNIFXLXX (SEQ ID NO: 126) |
| | SNXXXXXVXXXRXXX (SEQ ID NO: 127) |
| | XXXXFFXXXIFXLCG (SEQ ID NO: 128) |
| | SNXXXXXXXXXLCG (SEQ ID NO: 129) |
| | XXRXXXXKVNIFXXCX (SEQ ID NO: 130) |
| | SXXXFFXVXIXXXXG (SEQ ID NO: 131) |
| | SXRDFFKXNXXRXCX (SEQ ID NO: 132) |
| | XXXXXIQKXXXXNTLKXXKXXLXXX (SEQ ID NO: 133) |
| | ALVAKXXXFPVFXXXXLCXLXXXXX (SEQ ID NO: 134) |
| | ALVAKIQKXXXXXXXXXXKLXXXII (SEQ ID NO: 135) |
| | XXXXXXXXKXPXXNTLKXCKXEXEXX (SEQ ID NO: 136) |
| | XXXXXXQXFXVPXTLKLXKLXLXXX (SEQ ID NO: 137) |
| | XLVAKIXXXPVXNXXXLXXXXLXII (SEQ ID NO: 138) |
| | AXXAXIXXFXXFXXXXXCXXEXEII (SEQ ID NO: 139) |
| | XXGQVXXXKXKXX (SEQ ID NO: 140) |
| | IAXXXAAAXXXXX (SEQ ID NO: 141) |
| | XXGXXXXXKXKHI (SEQ ID NO: 142) |
| | IXXQVXXXKQKHI (SEQ ID NO: 143) |
| | XXXQVXXXXQXHI (SEQ ID NO: 144) |
| | XXRXPXXXXXKLWKXXLXXX (SEQ ID NO: 145) |
| | IQXXXVXXXLXXXXLXXXII (SEQ ID NO: 146) |
| | XXXLXXXNMXXWKXXXXXX (SEQ ID NO: 147) |
| | XXXLPXINMXKLXXXXLXXX (SEQ ID NO: 148) |
| | IQRLXXXXXXXXSLYXXXCRTC (SEQ ID NO: 149) |
| | XXXLPVXVXLPSLYXXXXXXX (SEQ ID NO: 150) |
| | IQRXXXIVIXXXXXCVIXXXX (SEQ ID NO: 151) |
| | XXXXPVXXXXPSLYXXXCRIC (SEQ ID NO: 152) |
| | IQRLXVIXILXXXXCXXCXXC (SEQ ID NO: 153) |
| | XXXLPXXXXXPXXXXVIXXTX (SEQ ID NO: 154) |
| | XXXLXVIVILXSLYCVICRTC (SEQ ID NO: 155) |
| | LXXPXPXYXFXXGIGXXXXWXXXWLNAQQMXXXXX (SEQ ID NO: 156) |
| | XXCPTPXXXFXXXXXNHLXXXIIWLXXXXXMXXXXX (SEQ ID NO: 157) |
| | LRCXXXXXXXXENGXXXXXMWNXXXXXXXXXXSYKNK (SEQ ID NO: 158) |
| | XXXXTXHYNXENGIGNHLMXNXXXXXNXQXXXXXKXK (SEQ ID NO: 159) |
| | LXCXXXHXNXXXXXGNHXXWXXXWLXXXXXMSXXNX (SEQ ID NO: 160) |
| | XRXPXPHXXFXXXXXXXXXXXXIIXXXAXQXSYXXX (SEQ ID NO: 161) |
| | SNRXXXMXXXXGLXGPXXIMXXXXX (SEQ ID NO: 162) |
| | XXXXFFMXXXXXXCXXFGXXXXKXX (SEQ ID NO: 163) |
| | SNRDXXXXXIFGLXGPXXIMXRKRR (SEQ ID NO: 164) |
| | SXXXXXXXVNXXXXCXXFGXXEXXXX (SEQ ID NO: 165) |
| | XXXXXXXXVNIFXXXXPXXXXXRXRR (SEQ ID NO: 166) |
| Other Putative AMPs | KSKLSLKKQGTIHLDAQSSCDVMHFPKCDLAPNVQRQAWLFKVA SKEAKELRYYLLNPYLDVSARNVGSKV (SEQ ID NO: 167) |
| | KAGEGERGEREVLNHQKTILEPSSCPLISPHSTGLGHRPSLFRL TLA (SEQ ID NO: 168) |
| | LKGIKNAAQLLRFPPNCKLCSCIVFVHKDHCVVQEASGVERF (SEQ ID NO: 169) |
| | NAARDHSATRCKQRSARLQIAAQDYRSQRSARLQIATQRKITD RNTA (SEQ ID NO: 170) |
| | LKPSNIQVKLQYIYW (SEQ ID NO: 171) |
| Further Putative AMP Precursors | MNCGSFPCDACDVCEYVDAKTKLKLPNGRWHSIQFRVICQTPG VIYLAQCLCGGFYIGKTKRQFFKRIRDHIKPIRKNKMDTAISR HVGIHHNFNPQFIKFSALEHIPQTLAVAALIASCYN (SEQ ID NO: 172) |
| | MEEIVFPLQHPFHLDCLFFLLRHLSWEKT (SEQ ID NO: 173) |
| | MSIKKKEEMIQVKGMLKWKNDFYQLLERFSVLCLEKNPEMLKL (SEQ ID NO: 174) |
| | MIQVKGMLKWKNDFYQLLERFSVLCLEKNPEMLKL |

TABLE 28 -continued

Sequences described herein and corresponding SEQ ID NOs

| Table/FIG. | SEQ ID NO |
|---|---|
| | (SEQ ID NO: 175)<br>MPKKKEETIQMKGMLKWKNDFFQLLHA (SEQ ID NO: 176)<br>MSGSRIGLPLALFPVTFVKISLFILLSSSSSAFLLGEHSYC<br>(SEQ ID NO: 177)<br>MSSPRRDANEEERRDDPDERDVEVEKRLLPVITSENVLV<br>HRGGQKAGMDHREVTQGWREDLGHQEELSLNLQENNGGH<br>PQFMPFQ (SEQ ID NO: 178) |

In the preceding description, for purposes of explanation, numerous details are set forth in order to provide a thorough understanding of the embodiments. However, it will be apparent to one skilled in the art that these specific details are not required.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

REFERENCES

The following publications are incorporated by reference herein.

1. Munita, J. M. & Arias, C. A. Mechanisms of Antibiotic Resistance. in *Virulence Mechanisms of Bacterial Pathogens*, Fifth Edition (eds. Kudva, I. T. et al.) 481-511 (American Society of Microbiology, 2016). doi:10.1128/microbiolspec.VMBF-0016-2015
2. Nathan, C. & Cars, O. Antibiotic Resistance—Problems, Progress, and Prospects. *N. Engl. J. Med.* 371, 1761-1763 (2014).
3. Antimicrobial resistance: global report on surveillance. (World Health Organization, 2014).
4. World Health Organization. Global action plan on antimicrobial resistance. (2015).
5. Jantaruk, P., Roytrakul, S., Sitthisak, S. & Kunthalert, D. Potential role of an antimicrobial peptide, KLK in inhibiting lipopolysaccharide-induced macrophage inflammation. *PLOS ONE* 12, e0183852 (2017).
6. Bahar, A. & Ren, D. Antimicrobial Peptides. *Pharmaceuticals* 6, 1543-1575 (2013).
7. Brandenburg, K., Heinbockel, L., Correa, W. & Lohner, K. Peptides with dual mode of action: Killing bacteria and preventing endotoxin-induced sepsis. *Biochim. Biophys. Acta BBA—Biomembr.* 1858, 971-979 (2016).
8. Lehrer (2013). "Innate Immunity in Plants: The Role of Antimicrobial Peptides" In: *Antimicrobial peptides and innate immunity*. Springer (Basel, Switzerland); Hiemstra & Zaat (Editors.) Ch. 2, p. 29-51.
9. Conlon, J. M. & Mechkarska, M. Host-defense peptides with therapeutic potential from skin secretions of frogs from the family Pipidae. *Pharmaceuticals* 7, 58-77 (2014).
10. Waghu, F. H., Barai, R. S., Gurung, P. & Idicula-Thomas, S. CAMP$_{R3}$: a database on sequences, structures and signatures of antimicrobial peptides: Table 1. *Nucleic Acids Res.* 44, D1094-D1097 (2016).
11. Andersson, D. I., Hughes, D. & Kubicek-Sutherland, J. Z. Mechanisms and consequences of bacterial resistance to antimicrobial peptides. *Drug Resist. Updat.* 26, 43-57 (2016).
12. Beckloff, N. & Diamond, G. Computational analysis suggests beta-defensins are processed to mature peptides by signal peptidase. *Protein Pept. Lett.* 15, 536-540 (2008).
13. Aittomski, S. et al. Proprotein convertase Furin1 expression in the *Drosophila* fat body is essential for a normal antimicrobial peptide response and bacterial host defense. *FASEB J.* fj.201700296R (2017).
14. Joo, H.-S., Fu, C.-I. & Otto, M. Bacterial strategies of resistance to antimicrobial peptides. *Philos. Trans. R. Soc. B Biol. Sci.* 371, 20150292 (2016).
15. Valore, E. V. & Ganz, T. Posttranslational processing of hepcidin in human hepatocytes is mediated by the prohormone convertase furin. *Blood Cells. Mol. Dis.* 40, 132-138 (2008).
16. Nguyen, L. T., Haney, E. F. & Vogel, H. J. The expanding scope of antimicrobial peptide structures and their modes of action. *Trends Biotechnol.* 29, 464-472 (2011).
17. Haney, E. F. et al. Mechanism of action of puroindoline derived tryptophan-rich antimicrobial peptides. *Biochim. Biophys. Acta BBA—Biomembr.* 1828, 1802-1813 (2013).
18. Otvos Jr., L. Immunomodulatory effects of anti-microbial peptides. Acta *Microbiol. Immunol. Hung.* 63, 257-277 (2016).
19. Schadich, E., Cole, A. L. J., Squire, M. & Mason, D. Skin peptides of different life stages of Ewing's tree frog. *J. Exp. Zool. Part Ecol. Genet. Physiol.* 313A, 532-537 (2009).
20. Batista, C. V. et al. A novel heterodimeric antimicrobial peptide from the tree-frog *Phyllomedusa distincta*. *FEBS Lett.* 494, 85-89 (2001).
21. Ge, L. et al. Balteatide: A novel antimicrobial decapeptide from the skin secretion of the purple-sided leaf frog, *Phyllomedusa baltea*. *Sci. World J.* 2014, 1-8 (2014).
22. Luca, V., Stringaro, A., Colone, M., Pini, A. & Mangoni, M. L. Esculentin(1-21), an amphibian skin membrane-active peptide with potent activity on both planktonic and biofilm cells of the bacterial pathogen *Pseudomonas aeruginosa*. *Cell. Mol. Life Sci.* 70, 2773-2786 (2013).
23. Liang, T. et al. Molecular cloning and expression analysis of liver-expressed antimicrobial peptide 1 (LEAP-1) and LEAP-2 genes in the blunt snout bream (Megalobrama amblycephala). *Fish Shellfish Immunol.* 35, 553-563 (2013).
24. Krause, A. Isolation and biochemical characterization of LEAP-2, a novel blood peptide expressed in the liver. *Protein Sci.* 12, 143-152 (2003).
25. Zhang, S. et al. Evolution, expression, and characterisation of liver-expressed antimicrobial peptide genes in ancient chondrostean sturgeons. *Fish Shellfish Immunol.* (2018).
26. Calhoun, D. M. et al. Role of antimicrobial peptides in amphibian defense against trematode infection. *EcoHealth* 13, 383-391 (2016).

27. Woodhams, D. C. et al. Life history linked to immune investment in developing amphibians. *Conserv. Physiol.* 4, cow025 (2016).
28. Hammond, S. A. et al. The North American bullfrog draft genome provides insight into hormonal regulation of long noncoding RNA. *Nat. Commun.* 8, (2017).
29. Hancock, R. E. W. Modified MIC method for cationic antimicrobial peptides. (1999). Available at: http://cmdr.ubc.ca/bobh/method/modified-mic-method-for-cationic-antimicrobial-peptides/. (Accessed: 22 Sep. 2017)
30. Dürr, U. H. N., Sudheendra, U. S. & Ramamoorthy, A. LL-37, the only human member of the cathelicidin family of antimicrobial peptides. *Biochim. Biophys. Acta BBA—Biomembr.* 1758, 1408-1425 (2006).
31. Goraya, J., Knoop, F. C. & Conlon, J. M. Ranatuerins: antimicrobial peptides isolated from the skin of the American bullfrog, *Rana catesbeiana*. *Biochem Biophys Res Commun* 250, 589-592 (1998).
33. Jackman, K. W. et al. Transcriptomics investigation of thyroid hormone disruption in the olfactory system of the *Rana* [*Lithobates*] *catesbeiana* tadpole. *Aquat. Toxicol.* 202, 46-56 (2018).
34. Reilly, D. S., Tomassini, N. & Zasloff, M. Expression of magainin antimicrobial peptide genes in the developing granular glands of *Xenopus* skin and induction by thyroid hormone. *Dev. Biol.* 162, 123-133 (1994).
35. Clark, D. P., Durell, S., Maloy, W. L. & Zasloff, M. Ranalexin. A novel antimicrobial peptide from bullfrog (*Rana catesbeiana*) skin, structurally related to the bacterial antibiotic, polymyxin. *J. Biol. Chem.* 269, 10849-10855 (1994).
36. Katzenback, B. A. et al. Regulation of the *Rana sylvatica* brevinin-1SY antimicrobial peptide during development and in dorsal and ventral skin in response to freezing, anoxia and dehydration. *J. Exp. Biol.* 217, 1392-1401 (2014).
37. Ohnuma, A., Conlon, J. M. & Iwamuro, S. Developmental and thyroid hormone-induced expression of preprotemporin genes in the skin of Japanese mountain brown frog *Rana ornativentris*. *Ann. N. Y. Acad. Sci.* 1163, 494-496 (2009).
38. Zaiou, M. & Gallo, R. L. Cathelicidins, essential gene-encoded mammalian antibiotics. *J. Mol. Med.* 80, 549-561 (2002).
39. Conlon, J. M. et al. Host defense peptides from *Lithobates forreri, Hylarana luctuosa*, and *Hylarana signata* (Ranidae): Phylogenetic relationships inferred from primary structures of ranatuerin-2 and brevinin-2 peptides. *Comp. Biochem. Physiol. Part D Genomics Proteomics* 9, 49-57 (2014).
40. Kościuczuk, E. M. et al. Cathelicidins: family of antimicrobial peptides. A review. *Mol. Biol. Rep.* 39, 10957-10970 (2012).
41. Zhang, S. et al. Evolution, expression, and characterisation of liver-expressed antimicrobial peptide genes in ancient chondrostean sturgeons. *Fish Shellfish Immunol.* 79, 363-369 (2018).
42. Conlon, J. M., Kolodziejek, J. & Nowotny, N. Antimicrobial peptides from the skins of North American frogs. *Biochim. Biophys. Acta BBA—Biomembr.* 1788, 1556-1563 (2009).
43. Unubol, N. et al. Peptide Antibiotics developed by mimicking natural antimicrobial peptides. *Clin. Microbiol. Open Access* 06, (2017).
44. Rollins-Smith, L. A. The role of amphibian antimicrobial peptides in protection of amphibians from pathogens linked to global amphibian declines. *Biochim. Biophys. Acta BBA—Biomembr.* 1788, 1593-1599 (2009).
45. Rollins-Smith, L. A. Amphibian immunity-stress, disease, and climate change. *Dev. Comp. Immunol.* 66, 111-119 (2017).
46. Holden, W. M., Reinert, L. K., Hanlon, S. M., Parris, M. J. & Rollins-Smith, L. A. Development of antimicrobial peptide defenses of southern leopard frogs, *Rana sphenocephala*, against the pathogenic chytrid fungus, *Batrachochytrium dendrobatidis*. *Dev. Comp. Immunol.* 48, 65-75 (2015).
47. Conlon, J. M. et al. Evaluation of the skin peptide defenses of the Oregon spotted frog *Rana pretiosa* against infection by the chytrid fungus *Batrachochytrium dendrobatidis*. *J Chem Ecol* 39, 797-805 (2013).
48. Robertson, G. et al. De novo assembly and analysis of RNA-seq data. *Nat. Methods* 7, 909-912 (2010).
49. Mistry, J., Finn, R. D., Eddy, S. R., Bateman, A. & Punta, M. Challenges in homology search: HMMER3 and convergent evolution of coiled-coil regions. *Nucleic Acids Res.* 41, e121-e121 (2013).
50. Jones, P. et al. InterProScan 5: genome-scale protein function classification. *Bioinformatics* 30, 1236-1240 (2014).
51. Finn, R. D. et al. The Pfam protein families database: towards a more sustainable future. *Nucleic Acids Res.* 44, D279-D285 (2016).
52. Wernersson, R. Virtual Ribosome—a comprehensive translation tool with support for sequence feature integration. *Nucl. Acids Res.* 34, W385-W388 (2006).
53. Sievers, F. et al. Fast, scalable generation of high-quality protein multiple sequence alignments using Clustal Omega. *Mol. Syst. Biol.* 7, 539-539 (2014).
54. Wu, T. D. & Watanabe, C. K. GMAP: a genomic mapping and alignment program for mRNA and EST sequences. *Bioinformatics* 21, 1859-1875 (2005).
55. Cameron, C. E., Brouwer, N. L., Tisch, L. M. & Kuroiwa, J. M. Y. Defining the Interaction of the *Treponema pallidum* Adhesin Tp0751 with Laminin. *Infect. Immun.* 73, 7485-7494 (2005).
56. Cockerill, F. & Clinical and Laboratory Standards Institute. *Methods for dilution antimicrobial susceptibility tests for bacteria that grow aerobically: approved standard*. (Clinical and Laboratory Standards Institute, 2015).

The invention claimed is:

1. An antimicrobial peptide consisting of the amino acid sequence according to SEQ ID NO:46.

2. A composition comprising the antimicrobial peptide according to claim 1, and a pharmaceutically acceptable excipient.

3. The composition of claim 2, wherein the composition is formulated for oral, injectable, rectal, topical, transdermal, nasal, or ocular delivery.

4. The composition of claim 2, wherein the composition is lyophilized.

5. A lipid vesicle comprising the antimicrobial peptide of claim 1.

6. A nucleic acid molecule encoding the antimicrobial peptide of claim 1.

7. A vector comprising the nucleic acid molecule of claim 6.

8. A kit for identifying a target molecule associated with an infectious agent, said kit comprising the antimicrobial peptide of claim 1 together with instructions for conducting a method of identifying a target molecule associated with an infectious agent, wherein said target molecule binds to the antimicrobial peptide, said method comprising the step of screening a library of candidate target molecules associated with the infectious agent, for a molecule that binds to the antimicrobial peptide;

wherein said infectious agent is Gram-negative bacteria, Gram-positive bacteria, acid fast bacteria, or a drug resistant bacteria.

9. A kit for identifying a target molecule for modulating biological activity, said kit comprising the antimicrobial peptide of claim 1 together with instructions for conducting a method of identifying a target molecule for modulating biological activity, wherein said target molecule binds to the antimicrobial peptide, said method comprising the step of screening a library of candidate target molecules for a molecule that binds to the antimicrobial peptide.

10. A method of treating bacterial infection in a subject in need thereof, wherein the method comprises administering to the subject a therapeutically effective amount of the antimicrobial peptide according to claim 1.

11. The method of claim 10, wherein the bacteria is Gram-negative bacteria.

12. The method of claim 10, wherein the bacteria is Gram-positive bacteria.

13. The method of claim 10, wherein the bacteria is *Escherichia coli, Salmonella enterica, Staphylococcus aureus, Pseudomonas aeruginosa, Streptococcus pyogenes, Mycobacterium smegmatis*, Methicillin-resistant *Staphylococcus aureus* (MRSA), *Salmonella enteritidis*, or *Salmonella* Heidelberg.

* * * * *

UNITED STATES PATENT AND TRADEMARK OFFICE
CERTIFICATE OF CORRECTION

| | | |
|---|---|---|
| PATENT NO. | : 12,280,090 B2 | Page 1 of 1 |
| APPLICATION NO. | : 17/312806 | |
| DATED | : April 22, 2025 | |
| INVENTOR(S) | : Birol et al. | |

It is certified that error appears in the above-identified patent and that said Letters Patent is hereby corrected as shown below:

In the Specification

In Column 1, Lines 17 - 20, delete "This invention was made in part with United States government support under Grant No. R01 HG007182, awarded by the National Institutes of Health. The United States government has certain rights in the invention."

Insert --This invention was made with government support under HG007182 awarded by the National Institutes of Health. The government has certain rights in the invention.--

Signed and Sealed this
Second Day of December, 2025

John A. Squires
*Director of the United States Patent and Trademark Office*

SEQUENCE LISTING

<160> NUMBER OF SEQ ID NOS: 178

<210> SEQ ID NO 1
<211> LENGTH: 42
<212> TYPE: PRT
<213> ORGANISM: Artificial Sequence
<220> FEATURE:
<223> OTHER INFORMATION: Antimicrobial peptide with reference to North American bullfrog, Rana (Lithobates) catesbeiana

<400> SEQUENCE: 1

Met Phe Thr Met Lys Lys Ser Leu Leu Leu Phe Phe Leu Gly Thr
1               5                   10                  15

Ile Ser Leu Ser Leu Cys Glu Gln Gly Arg Asn Ala Asp Asp Gln
            20                  25                  30

Gly Glu Val Ile Glu Gln Lys Val Lys Arg
        35                  40

<210> SEQ ID NO 2
<211> LENGTH: 29
<212> TYPE: PRT
<213> ORGANISM: Artificial Sequence
<220> FEATURE:
<223> OTHER INFORMATION: Antimicrobial peptide based on North American
      bullfrog, Rana (Lithobates) catesbeiana

<400> SEQUENCE: 2

Ala Phe Leu Ser Thr Val Lys Asn Thr Leu Thr Asn Val Ala Gly Thr
1               5                   10                  15

Met Ile Asp Thr Phe Lys Cys Lys Ile Thr Gly Val Cys
            20                  25

<210> SEQ ID NO 3
<211> LENGTH: 31
<212> TYPE: PRT
<213> ORGANISM: Artificial Sequence
<220> FEATURE:
<223> OTHER INFORMATION: Antimicrobial peptide based on North American
      bullfrog, Rana (Lithobates) catesbeiana

<400> SEQUENCE: 3

Val Leu Leu Tyr Leu Ile Ile Thr Val Ser Phe Pro Arg Arg Asp Ala
1               5                   10                  15

Asn Asp Glu Asp Gly Gly Glu Val Thr Lys Glu Val Val Lys Arg
            20                  25                  30

<210> SEQ ID NO 4
<211> LENGTH: 19
<212> TYPE: PRT
<213> ORGANISM: Artificial Sequence
<220> FEATURE:
<223> OTHER INFORMATION: Antimicrobial peptide based on North American
      bullfrog, Rana (Lithobates) catesbeiana

<400> SEQUENCE: 4

Ser Leu Ser Gly Cys Trp Thr Lys Ser Phe Pro Arg Lys Pro Cys Leu
1               5                   10                  15

Arg Asn Arg

<210> SEQ ID NO 5
<211> LENGTH: 36
<212> TYPE: PRT
<213> ORGANISM: Artificial Sequence
<220> FEATURE:
<223> OTHER INFORMATION: Antimicrobial peptide based on North American
      bullfrog, Rana (Lithobates) catesbeiana

<400> SEQUENCE: 5

Met Ser Ser Phe Cys Glu Ile Thr Asn Val Ala Leu Thr Ile Ser Leu
1               5                   10                  15

Ser Ser Pro Arg Arg Gly Ala Asp Glu Glu Gly Asn Gly Glu Lys
            20                  25                  30

-continued

```
Glu Ile Lys Arg
        35

<210> SEQ ID NO 6
<211> LENGTH: 25
<212> TYPE: PRT
<213> ORGANISM: Artificial Sequence
<220> FEATURE:
<223> OTHER INFORMATION: Antimicrobial peptide based on North American
      bullfrog, Rana (Lithobates) catesbeiana

<400> SEQUENCE: 6

Ser Met Leu Ser Val Leu Lys Asn Leu Gly Lys Val Gly Leu Gly Phe
1               5                   10                  15

Val Ala Cys Lys Ile Asn Lys Gln Cys
            20                  25

<210> SEQ ID NO 7
<211> LENGTH: 43
<212> TYPE: PRT
<213> ORGANISM: Artificial Sequence
<220> FEATURE:
<223> OTHER INFORMATION: Antimicrobial peptide based on North American
      bullfrog, Rana (Lithobates) catesbeiana

<400> SEQUENCE: 7

Met Thr Gln Ser Thr Gln Lys Trp Phe Lys Thr Lys Tyr Trp Arg Val
1               5                   10                  15

Arg Asn Arg Pro Ala Met Ser Pro Asp Leu Asn Pro Ile Glu His Leu
            20                  25                  30

Trp Arg Asp Leu Lys Lys Val Val Gly Lys Arg
        35                  40

<210> SEQ ID NO 8
<211> LENGTH: 33
<212> TYPE: PRT
<213> ORGANISM: Artificial Sequence
<220> FEATURE:
<223> OTHER INFORMATION: Antimicrobial peptide based on North American
      bullfrog, Rana (Lithobates) catesbeiana

<400> SEQUENCE: 8

Asn Pro Ser Asn Leu Arg Ala Leu Glu Glu Leu Val Lys Glu Cys
1               5                   10                  15

Ser Glu Ile Pro Val Glu Arg Cys Lys Lys Leu Ile Tyr Gly Tyr Arg
            20                  25                  30

Lys

<210> SEQ ID NO 9
<211> LENGTH: 26
<212> TYPE: PRT
<213> ORGANISM: Artificial Sequence
<220> FEATURE:
<223> OTHER INFORMATION: Antimicrobial peptide based on North American
      bullfrog, Rana (Lithobates) catesbeiana

<400> SEQUENCE: 9

Met Arg Lys Arg Met Thr Met Arg Met Lys Lys Lys Ser
1               5                   10                  15

Glu Lys Glu Arg Arg Glu Arg Gly Lys Arg
            20                  25

<210> SEQ ID NO 10
```

```
<211> LENGTH: 25
<212> TYPE: PRT
<213> ORGANISM: Artificial Sequence
<220> FEATURE:
<223> OTHER INFORMATION: Antimicrobial peptide based on North American
      bullfrog, Rana (Lithobates) catesbeiana

<400> SEQUENCE: 10

Met Met Arg Val Met Arg Arg Lys Thr Lys Val Ile Trp Glu Lys Lys
1               5                   10                  15

Asp Phe Ile Gly Leu Tyr Ser Ile Asp
            20                  25

<210> SEQ ID NO 11
<211> LENGTH: 19
<212> TYPE: PRT
<213> ORGANISM: Artificial Sequence
<220> FEATURE:
<223> OTHER INFORMATION: Antimicrobial peptide based on North American
      bullfrog, Rana (Lithobates) catesbeiana

<400> SEQUENCE: 11

Met Phe Phe Met Ser Ser Pro Arg Arg Asp Ala Asp Glu Val Lys Glu
1               5                   10                  15

Val Lys Arg

<210> SEQ ID NO 12
<211> LENGTH: 32
<212> TYPE: PRT
<213> ORGANISM: Artificial Sequence
<220> FEATURE:
<223> OTHER INFORMATION: Antimicrobial peptide based on North American
      bullfrog, Rana (Lithobates) catesbeiana

<400> SEQUENCE: 12

Gly Phe Leu Asp Ile Ile Lys Asn Leu Gly Lys Thr Phe Ala Gly His
1               5                   10                  15

Met Leu Asp Lys Ile Lys Cys Thr Ile Gly Thr Cys Pro Pro Ser Pro
            20                  25                  30

<210> SEQ ID NO 13
<211> LENGTH: 23
<212> TYPE: PRT
<213> ORGANISM: Artificial Sequence
<220> FEATURE:
<223> OTHER INFORMATION: Antimicrobial peptide based on North American
      bullfrog, Rana (Lithobates) catesbeiana

<400> SEQUENCE: 13

Met Ile Thr Val Ser Ser Pro Arg Arg Asp Ala Asp Gly Asp Glu Gly
1               5                   10                  15

Glu Val Glu Glu Val Lys Arg
            20

<210> SEQ ID NO 14
<211> LENGTH: 31
<212> TYPE: PRT
<213> ORGANISM: Artificial Sequence
<220> FEATURE:
<223> OTHER INFORMATION: Antimicrobial peptide based on North American
      bullfrog, Rana (Lithobates) catesbeiana

<400> SEQUENCE: 14

Gly Phe Leu Asp Ile Ile Lys Asp Thr Gly Lys Glu Phe Ala Val Lys
1               5                   10                  15
```

Ile Leu Asn Asn Leu Lys Cys Lys Leu Ala Gly Gly Cys Pro Pro
            20                  25                  30

<210> SEQ ID NO 15
<211> LENGTH: 71
<212> TYPE: PRT
<213> ORGANISM: Artificial Sequence
<220> FEATURE:
<223> OTHER INFORMATION: Putative AMP precursor based on Pseudacris
      regilla Ranatuerin-2PRc

<400> SEQUENCE: 15

Met Phe Thr Met Lys Lys Ser Leu Leu Leu Phe Phe Leu Gly Thr
1               5                   10                  15

Ile Ser Leu Ser Leu Cys Glu Glu Glu Arg Asp Ala Asp Asp Gln
            20                  25                  30

Gly Glu Val Val Lys Lys Glu Val Lys Arg Ala Phe Phe Thr Thr Val
            35                  40                  45

Lys Asn Leu Val Thr Asn Val Ala Gly Thr Val Ile Asp Lys Met Lys
            50                  55                  60

Cys Lys Leu Thr Gly Gln Cys
65                  70

<210> SEQ ID NO 16
<211> LENGTH: 71
<212> TYPE: PRT
<213> ORGANISM: Artificial Sequence
<220> FEATURE:
<223> OTHER INFORMATION: Putative AMP precursor based on R. catesbeiana
      HP2

<400> SEQUENCE: 16

Met Phe Thr Met Lys Lys Ser Leu Leu Leu Phe Phe Leu Gly Thr
1               5                   10                  15

Ile Ser Leu Ser Leu Cys Glu Gln Glu Arg Asn Ala Asp Asp Gln
            20                  25                  30

Gly Glu Val Ile Glu Gln Lys Val Lys Arg Ala Phe Leu Ser Thr Val
            35                  40                  45

Lys Asn Thr Leu Thr Asn Val Ala Gly Thr Met Ile Asp Thr Phe Lys
            50                  55                  60

Cys Lys Ile Thr Gly Val Cys
65                  70

<210> SEQ ID NO 17
<211> LENGTH: 66
<212> TYPE: PRT
<213> ORGANISM: Artificial Sequence
<220> FEATURE:
<223> OTHER INFORMATION: Ranatuerin precursor sequences

<400> SEQUENCE: 17

Met Phe Thr Leu Lys Lys Ser Leu Leu Leu Phe Phe Leu Gly Thr
1               5                   10                  15

Ile Thr Leu Ser Leu Cys Glu Gln Glu Arg Gly Ala Asp Glu Glu Glu
            20                  25                  30

Gly Asn Gly Glu Lys Glu Ile Lys Arg Ser Met Leu Ser Val Leu Lys
            35                  40                  45

Asn Leu Gly Lys Val Gly Leu Gly Phe Val Ala Cys Lys Ile Asn Lys
            50                  55                  60

Gln Cys
65

```
<210> SEQ ID NO 18
<211> LENGTH: 61
<212> TYPE: PRT
<213> ORGANISM: Artificial Sequence
<220> FEATURE:
<223> OTHER INFORMATION: Ranatuerin precursor sequence

<400> SEQUENCE: 18
```

Met Ser Ser Phe Cys Glu Ile Thr Asn Val Ala Leu Thr Ile Ser Leu
1               5                   10                  15

Ser Ser Pro Arg Arg Gly Ala Asp Glu Glu Gly Asn Gly Glu Lys
            20                  25                  30

Glu Ile Lys Arg Ser Met Leu Ser Val Leu Lys Asn Leu Gly Lys Val
        35                  40                  45

Gly Leu Gly Phe Val Ala Cys Lys Ile Asn Lys Gln Cys
    50                  55                  60

```
<210> SEQ ID NO 19
<211> LENGTH: 51
<212> TYPE: PRT
<213> ORGANISM: Artificial Sequence
<220> FEATURE:
<223> OTHER INFORMATION: Ranatuerin precursor sequence

<400> SEQUENCE: 19
```

Met Phe Phe Met Ser Ser Pro Arg Arg Asp Ala Asp Glu Val Lys Glu
1               5                   10                  15

Val Lys Arg Gly Phe Leu Asp Ile Ile Lys Asn Leu Gly Lys Thr Phe
            20                  25                  30

Ala Gly His Met Leu Asp Lys Ile Lys Cys Thr Ile Gly Thr Cys Pro
        35                  40                  45

Pro Ser Pro
    50

```
<210> SEQ ID NO 20
<211> LENGTH: 68
<212> TYPE: PRT
<213> ORGANISM: Artificial Sequence
<220> FEATURE:
<223> OTHER INFORMATION: Ranatuerin precursor sequence

<400> SEQUENCE: 20
```

Met Phe Thr Met Lys Lys Ser Leu Leu Leu Leu Phe Phe Leu Gly Thr
1               5                   10                  15

Ile Ser Leu Ser Leu Cys Glu Pro Gln Arg Asp Ala Asp Glu Val Lys
            20                  25                  30

Glu Val Lys Arg Gly Phe Leu Asp Ile Ile Lys Asn Leu Gly Lys Thr
        35                  40                  45

Phe Ala Gly His Met Leu Asp Lys Ile Lys Cys Thr Ile Gly Thr Cys
    50                  55                  60

Pro Pro Ser Pro
65

```
<210> SEQ ID NO 21
<211> LENGTH: 70
<212> TYPE: PRT
<213> ORGANISM: Artificial Sequence
<220> FEATURE:
<223> OTHER INFORMATION: Ranatuerin precursor sequence

<400> SEQUENCE: 21
```

```
Met Phe Thr Leu Lys Lys Ser Leu Leu Leu Phe Phe Leu Gly Thr
1               5                   10                  15

Ile Asn Leu Ser Leu Cys Glu Glu Arg Asp Ala Glu Glu Arg
            20                  25                  30

Arg Asp Asn Pro Asp Glu Arg Asp Val Glu Val Glu Lys Arg Phe Leu
            35                  40                  45

Pro Phe Ile Ala Arg Leu Ala Ala Lys Val Phe Pro Ser Ile Ile Cys
        50                  55                  60

Ser Val Thr Lys Lys Cys
65              70
```

<210> SEQ ID NO 22
<211> LENGTH: 71
<212> TYPE: PRT
<213> ORGANISM: Artificial Sequence
<220> FEATURE:
<223> OTHER INFORMATION: Ranatuerin precursor sequence

<400> SEQUENCE: 22

```
Met Phe Thr Met Lys Lys Ser Leu Leu Leu Phe Phe Leu Gly Thr
1               5                   10                  15

Ile Ser Leu Ser Leu Cys Glu Gln Glu Arg Asn Ala Asp Asp Gln
            20                  25                  30

Gly Glu Val Ile Glu Gln Lys Val Lys Arg Ala Phe Leu Ser Thr Val
            35                  40                  45

Lys Asn Thr Leu Thr Asn Val Ala Gly Thr Met Ile Asp Thr Phe Lys
        50                  55                  60

Cys Lys Ile Thr Gly Val Cys
65              70
```

<210> SEQ ID NO 23
<211> LENGTH: 74
<212> TYPE: PRT
<213> ORGANISM: Artificial Sequence
<220> FEATURE:
<223> OTHER INFORMATION: Ranatuerin precursor sequence

<400> SEQUENCE: 23

```
Met Phe Thr Leu Lys Lys Ser Leu Leu Leu Phe Phe Leu Gly Thr
1               5                   10                  15

Ile Thr Leu Ser Leu Cys Glu Gln Glu Arg Gly Ala Asp Glu Asp Asn
            20                  25                  30

Gly Gly Glu Met Thr Glu Glu Val Lys Arg Gly Leu Phe Leu Asp
            35                  40                  45

Thr Leu Lys Gly Ala Ala Lys Asp Val Ala Gly Lys Leu Leu Glu Gly
        50                  55                  60

Leu Lys Cys Lys Ile Thr Gly Cys Lys Pro
65              70
```

<210> SEQ ID NO 24
<211> LENGTH: 67
<212> TYPE: PRT
<213> ORGANISM: Artificial Sequence
<220> FEATURE:
<223> OTHER INFORMATION: Ranacyclin precursor sequence from R.
      catesbeiana

<400> SEQUENCE: 24

```
Met Phe Thr Met Lys Lys Ser Leu Leu Leu Phe Phe Leu Gly Ile
1               5                   10                  15
```

-continued

Ile Ser Leu Ser Leu Cys Glu Gln Glu Arg Asp Ala Asn Asp Glu Glu
            20                  25                  30

Asp Gly Gly Glu Val Thr Lys Glu Val Val Lys Arg Ser Leu Arg Gly
        35                  40                  45

Cys Trp Thr Lys Ser Phe Pro Pro Gln Pro Cys Leu Gly Lys Arg Leu
    50                  55                  60

Asn Met Asn
65

<210> SEQ ID NO 25
<211> LENGTH: 63
<212> TYPE: PRT
<213> ORGANISM: Artificial Sequence
<220> FEATURE:
<223> OTHER INFORMATION: Ranacyclin precursor sequence from R.
      catesbeiana

<400> SEQUENCE: 25

Met Phe Thr Leu Lys Lys Ser Leu Leu Leu Phe Phe Phe Gly Ile
1               5                   10                  15

Ile Ser Leu Ser Phe Cys Glu Gln Glu Arg Asp Ala Asn Asp Glu Glu
            20                  25                  30

Asp Gly Gly Glu Val Thr Lys Glu Val Val Lys Arg Ser Leu Arg Gly
        35                  40                  45

Cys Trp Thr Lys Ser Tyr Pro Pro Gln Pro Cys Leu Gly Lys Arg
    50                  55                  60

<210> SEQ ID NO 26
<211> LENGTH: 50
<212> TYPE: PRT
<213> ORGANISM: Artificial Sequence
<220> FEATURE:
<223> OTHER INFORMATION: Ranacyclin precursor sequence from R.
      catesbeiana

<400> SEQUENCE: 26

Val Leu Leu Tyr Leu Ile Ile Thr Val Ser Phe Pro Arg Arg Asp Ala
1               5                   10                  15

Asn Asp Glu Asp Gly Gly Glu Val Thr Lys Glu Val Val Lys Arg Ser
            20                  25                  30

Leu Ser Gly Cys Trp Thr Lys Ser Phe Pro Arg Lys Pro Cys Leu Arg
        35                  40                  45

Asn Arg
    50

<210> SEQ ID NO 27
<211> LENGTH: 42
<212> TYPE: PRT
<213> ORGANISM: Artificial Sequence
<220> FEATURE:
<223> OTHER INFORMATION: Catesbeianin-1 precursor sequence from R.
      catesbeiana

<400> SEQUENCE: 27

Met Phe Thr Met Lys Lys Ser Glu Lys Glu Arg Arg Glu Arg Gly Lys
1               5                   10                  15

Arg Met Met Arg Val Met Arg Arg Lys Thr Lys Val Ile Trp Glu Lys
            20                  25                  30

Lys Asp Phe Ile Gly Leu Tyr Ser Ile Asp
        35                  40

<210> SEQ ID NO 28
<211> LENGTH: 51
<212> TYPE: PRT
<213> ORGANISM: Artificial Sequence
<220> FEATURE:
<223> OTHER INFORMATION: Catesbeianin-1 precursor sequence from R. catesbeiana

<400> SEQUENCE: 28

```
Met Arg Lys Arg Met Thr Met Arg Arg Met Lys Lys Lys Ser
1               5                   10                  15

Glu Lys Glu Arg Arg Glu Arg Gly Lys Arg Met Met Arg Val Met Arg
            20                  25                  30

Arg Lys Thr Lys Val Ile Trp Glu Lys Lys Asp Phe Ile Gly Leu Tyr
        35                  40                  45

Ser Ile Asp
    50
```

<210> SEQ ID NO 29
<211> LENGTH: 71
<212> TYPE: PRT
<213> ORGANISM: Artificial Sequence
<220> FEATURE:
<223> OTHER INFORMATION: Palustrin-Ca precursor sequence from R. catesbeiana

<400> SEQUENCE: 29

```
Met Phe Thr Met Lys Lys Ser Leu Leu Leu Phe Phe Leu Gly Thr
1               5                   10                  15

Ile Ser Leu Ser Leu Cys Glu Gln Glu Arg Asp Ala Asp Gly Asp Glu
            20                  25                  30

Gly Glu Val Glu Glu Val Lys Arg Gly Phe Leu Asp Ile Ile Lys Asp
        35                  40                  45

Thr Gly Lys Glu Phe Ala Val Lys Ile Leu Asn Asn Leu Cys Lys
    50                  55                  60

Leu Ala Gly Gly Cys Pro Pro
65                  70
```

<210> SEQ ID NO 30
<211> LENGTH: 54
<212> TYPE: PRT
<213> ORGANISM: Artificial Sequence
<220> FEATURE:
<223> OTHER INFORMATION: Palustrin-Ca precursor sequence from R. catesbeiana

<400> SEQUENCE: 30

```
Met Ile Thr Val Ser Ser Pro Arg Arg Asp Ala Asp Gly Asp Glu Gly
1               5                   10                  15

Glu Val Glu Glu Val Lys Arg Gly Phe Leu Asp Ile Ile Lys Asp Thr
            20                  25                  30

Gly Lys Glu Phe Ala Val Lys Ile Leu Asn Asn Leu Cys Lys Leu
        35                  40                  45

Ala Gly Gly Cys Pro Pro
    50
```

<210> SEQ ID NO 31
<211> LENGTH: 179
<212> TYPE: PRT
<213> ORGANISM: Artificial Sequence
<220> FEATURE:
<223> OTHER INFORMATION: Amolops loloensis Cathelicidin-AL sequence

<400> SEQUENCE: 31

```
Met Gly Leu Ser Ala Thr Leu Trp Phe Leu Met Gly Val Ala Ala Gly
1               5                   10                  15

Ser Met Ala Ser Pro Leu Leu Gln Trp Ser Glu Asp Asp Ile Ser Val
                20                  25                  30

Met Ala Leu Tyr Ser Thr Asp Tyr Tyr Asn Lys Val Ser Gly Glu Asp
            35                  40                  45

Val Leu Tyr Gly Leu Gln Glu Asn Asn Thr Glu Tyr Ile Thr Asp Glu
        50                  55                  60

Lys Ser Arg Phe His Gln Leu Ser Phe Pro Ile Gln Lys Thr Val Cys
65                  70                  75                  80

Gln Lys Ser Asp Asn Ala Leu Thr Asp Asp Cys Ala Phe Lys Glu Gly
                85                  90                  95

Gly Val Val Lys Ser Cys Thr Ser Tyr Phe Phe Glu Glu Asp Asp Arg
                100                 105                 110

Asp Ile Ile Val Val Thr Cys Gln Ser Gln Asp Gly His Arg Glu His
                115                 120                 125

Ser Arg Val Arg Arg Ser Arg Arg Gly Arg Gly Gly Arg Arg Gly
    130                 135                 140

Gly Ser Gly Gly Arg Gly Gly Arg Gly Gly Gly Arg Ser Gly Ala
145                 150                 155                 160

Gly Ser Ser Ile Ala Gly Val Gly Ser Arg Gly Gly Gly Gly Gly Arg
                165                 170                 175

His Tyr Ala
```

<210> SEQ ID NO 32
<211> LENGTH: 181
<212> TYPE: PRT
<213> ORGANISM: Artificial Sequence
<220> FEATURE:
<223> OTHER INFORMATION: R. catesbeiana Cathelicidin-AL sequence that aligns with an Amolops loloensis Cathelicidin-AL sequence

<400> SEQUENCE: 32

```
Met Gly Leu Ser Ala Thr Phe Trp Phe Leu Met Gly Leu Ala Ala Ser
1               5                   10                  15

Ser Met Ala Ser Pro Leu Leu Gln Trp Ser Glu Asp Asp Ala Ala Val
                20                  25                  30

Met Ala Leu Tyr Ser Ala Asp His Tyr Asn Lys Val Ser Gly Glu Asp
            35                  40                  45

Val Leu Tyr Gly Leu Leu Glu Asn Asp Thr Glu Tyr Ile Thr Asp Glu
        50                  55                  60

Lys Ser Arg Phe His Gln Leu Ser Phe Pro Ile Gln Glu Thr Val Cys
65                  70                  75                  80

Gln Lys Ser Asp Asn Asn Ala Pro Thr Asp Asp Cys Ala Phe Lys Glu
                85                  90                  95

Gly Gly Val Val Lys Ser Cys Thr Ser Tyr Phe Phe Glu Glu Asp Asp
                100                 105                 110

Arg Asp Ile Val Val Val Asn Cys Gln Ser Gln Asp Ser His Arg Glu
                115                 120                 125

His Ser Arg Val Arg Arg Ser Arg Ser Gly Arg Gly Gly Gly Gly Arg
    130                 135                 140

Gly Gly Gly Gly Arg Gly Gly Ser Arg Gly Gly Ser Arg Ser Gly Ser
145                 150                 155                 160
```

```
Arg Ser Ser Ile Ala Gly Gly Gly Ser Gly Gly Ser Arg Gly Gly
                165                 170                 175

Gly Thr Arg Tyr Ala
            180

<210> SEQ ID NO 33
<211> LENGTH: 81
<212> TYPE: PRT
<213> ORGANISM: Artificial Sequence
<220> FEATURE:
<223> OTHER INFORMATION: Nanorana parkeri predicted LEAP2 sequence

<400> SEQUENCE: 33

Met Ile Pro Gln Leu Arg Lys Trp Met Ala Ile Phe Val Met Cys Ile
1               5                   10                  15

Val Leu Ile His Gln Leu Glu Gly Ala Pro Met Asn Ser Asn Asp Gly
            20                  25                  30

Ser Lys Thr Ala Leu Arg Leu Arg Arg Met Thr Pro Phe Trp Arg Gly
        35                  40                  45

Leu Ser Leu Arg Pro Val Gly Ala Ser Cys Arg Asp Asp Thr Glu Cys
    50                  55                  60

Leu Thr Arg Leu Cys Arg Asn Gln Arg Cys Ser Leu Lys Thr Phe Ala
65                  70                  75                  80

Asp

<210> SEQ ID NO 34
<211> LENGTH: 81
<212> TYPE: PRT
<213> ORGANISM: Artificial Sequence
<220> FEATURE:
<223> OTHER INFORMATION: R. catesbeiana LEAP2 sequence aligning with
      Nanorana parkeri predicted LEAP2 sequence

<400> SEQUENCE: 34

Met Thr Pro Gln Leu Arg Lys Trp Thr Ala Ile Phe Val Ile Cys Ile
1               5                   10                  15

Val Leu Ile His Gln Leu Glu Gly Ala Pro Met Ser Asn Thr Ala Gly
            20                  25                  30

Ser Lys Thr Leu Leu Arg Leu Arg Arg Met Thr Pro Phe Trp Arg Gly
        35                  40                  45

Leu Ser Leu Arg Pro Val Gly Ala Ser Cys Arg Asp Asp Thr Glu Cys
    50                  55                  60

Leu Thr Arg Leu Cys Arg Lys Glu Arg Cys Ser Leu Lys Thr Phe Ala
65                  70                  75                  80

Asp

<210> SEQ ID NO 35
<211> LENGTH: 12
<212> TYPE: PRT
<213> ORGANISM: Artificial Sequence
<220> FEATURE:
<223> OTHER INFORMATION: P1_CCH, 'natural' antimicrobial peptide

<400> SEQUENCE: 35

Phe Tyr Phe Pro Val Ser Arg Lys Phe Gly Gly Lys
1               5                   10

<210> SEQ ID NO 36
<211> LENGTH: 12
<212> TYPE: PRT
<213> ORGANISM: Artificial Sequence
```

```
<220> FEATURE:
<223> OTHER INFORMATION: P1_CCH_F9R_Y2P, 'synthetic' AMP

<400> SEQUENCE: 36

Phe Pro Phe Pro Val Ser Arg Lys Arg Gly Gly Lys
 1               5                  10

<210> SEQ ID NO 37
<211> LENGTH: 26
<212> TYPE: PRT
<213> ORGANISM: Artificial Sequence
<220> FEATURE:
<223> OTHER INFORMATION: P2_CCH, 'natural' AMP

<400> SEQUENCE: 37

Phe Phe Pro Arg Val Leu Pro Leu Ala Asn Lys Phe Leu Pro Thr Ile
 1               5                  10                  15

Tyr Cys Ala Leu Pro Lys Ser Val Gly Asn
                20                  25

<210> SEQ ID NO 38
<211> LENGTH: 26
<212> TYPE: PRT
<213> ORGANISM: Artificial Sequence
<220> FEATURE:
<223> OTHER INFORMATION: P2_CCH_T15K_P7R, 'synthetic' AMP

<400> SEQUENCE: 38

Phe Phe Pro Arg Val Leu Arg Leu Ala Asn Lys Phe Leu Pro Lys Ile
 1               5                  10                  15

Tyr Cys Ala Leu Pro Lys Ser Val Gly Asn
                20                  25

<210> SEQ ID NO 39
<211> LENGTH: 32
<212> TYPE: PRT
<213> ORGANISM: Artificial Sequence
<220> FEATURE:
<223> OTHER INFORMATION: P3_CCH, 'natural' AMP

<400> SEQUENCE: 39

Gly Leu Leu Asp Ile Ile Lys Asp Thr Gly Lys Thr Thr Gly Ile Leu
 1               5                  10                  15

Met Asp Thr Leu Lys Cys Gln Met Thr Gly Arg Cys Pro Pro Ser Ser
                20                  25                  30

<210> SEQ ID NO 40
<211> LENGTH: 32
<212> TYPE: PRT
<213> ORGANISM: Artificial Sequence
<220> FEATURE:
<223> OTHER INFORMATION: P3_CCH_D8K_Q23C, 'synthetic' AMP

<400> SEQUENCE: 40

Gly Leu Leu Asp Ile Ile Lys Lys Thr Gly Lys Thr Thr Gly Ile Leu
 1               5                  10                  15

Met Asp Thr Leu Lys Cys Cys Met Thr Gly Arg Cys Pro Pro Ser Ser
                20                  25                  30

<210> SEQ ID NO 41
<211> LENGTH: 31
<212> TYPE: PRT
<213> ORGANISM: Artificial Sequence
<220> FEATURE:
<223> OTHER INFORMATION: P4_CCH, 'natural' AMP
```

<400> SEQUENCE: 41

Gly Leu Leu Asp Ile Ile Lys Thr Thr Gly Lys Asp Phe Ala Val Lys
1               5                   10                  15

Ile Leu Asp Asn Leu Lys Cys Lys Leu Ala Gly Gly Cys Pro Pro
            20                  25                  30

<210> SEQ ID NO 42
<211> LENGTH: 31
<212> TYPE: PRT
<213> ORGANISM: Artificial Sequence
<220> FEATURE:
<223> OTHER INFORMATION: P4_CCH_P31K, 'synthetic' AMP

<400> SEQUENCE: 42

Gly Leu Leu Asp Ile Ile Lys Thr Thr Gly Lys Asp Phe Ala Val Lys
1               5                   10                  15

Ile Leu Asp Asn Leu Lys Cys Lys Leu Ala Gly Gly Cys Pro Lys
            20                  25                  30

<210> SEQ ID NO 43
<211> LENGTH: 24
<212> TYPE: PRT
<213> ORGANISM: Artificial Sequence
<220> FEATURE:
<223> OTHER INFORMATION: P5_CCH, 'natural' AMP

<400> SEQUENCE: 43

Phe Phe Pro Ile Ile Ala Arg Leu Ala Ala Lys Val Ile Pro Ser Leu
1               5                   10                  15

Val Cys Ala Val Thr Lys Lys Cys
            20

<210> SEQ ID NO 44
<211> LENGTH: 24
<212> TYPE: PRT
<213> ORGANISM: Artificial Sequence
<220> FEATURE:
<223> OTHER INFORMATION: P5_CCH_A19K, 'synthetic' AMP

<400> SEQUENCE: 44

Phe Phe Pro Ile Ile Ala Arg Leu Ala Ala Lys Val Ile Pro Ser Leu
1               5                   10                  15

Val Cys Lys Val Thr Lys Lys Cys
            20

<210> SEQ ID NO 45
<211> LENGTH: 31
<212> TYPE: PRT
<213> ORGANISM: Artificial Sequence
<220> FEATURE:
<223> OTHER INFORMATION: P6_CCH, 'natural' AMP

<400> SEQUENCE: 45

Gly Leu Trp Glu Thr Ile Lys Thr Thr Gly Lys Ser Ile Ala Leu Asn
1               5                   10                  15

Leu Leu Asp Lys Ile Lys Cys Lys Ile Ala Gly Gly Cys Pro Pro
            20                  25                  30

<210> SEQ ID NO 46
<211> LENGTH: 31
<212> TYPE: PRT
<213> ORGANISM: Artificial Sequence
<220> FEATURE:

<223> OTHER INFORMATION: P6_CCH_S12K, 'synthetic' AMP

<400> SEQUENCE: 46

Gly Leu Trp Glu Thr Ile Lys Thr Thr Gly Lys Lys Ile Ala Leu Asn
1               5                   10                  15

Leu Leu Asp Lys Ile Lys Cys Lys Ile Ala Gly Gly Cys Pro Pro
            20                  25                  30

<210> SEQ ID NO 47
<211> LENGTH: 26
<212> TYPE: PRT
<213> ORGANISM: Artificial Sequence
<220> FEATURE:
<223> OTHER INFORMATION: P7_CCH, 'natural' AMP

<400> SEQUENCE: 47

Ala Thr Ala Trp Arg Ile Pro Pro Pro Gly Met Gln Pro Ile Ile Pro
1               5                   10                  15

Ile Arg Ile Arg Pro Leu Cys Gly Lys Gln
            20                  25

<210> SEQ ID NO 48
<211> LENGTH: 26
<212> TYPE: PRT
<213> ORGANISM: Artificial Sequence
<220> FEATURE:
<223> OTHER INFORMATION: P7_CCH_P9R_R5M, 'synthetic' AMP

<400> SEQUENCE: 48

Ala Thr Ala Trp Met Ile Pro Pro Arg Gly Met Gln Pro Ile Ile Pro
1               5                   10                  15

Ile Arg Ile Arg Pro Leu Cys Gly Lys Gln
            20                  25

<210> SEQ ID NO 49
<211> LENGTH: 12
<212> TYPE: PRT
<213> ORGANISM: Artificial Sequence
<220> FEATURE:
<223> OTHER INFORMATION: P8_CCH, 'natural' AMP

<400> SEQUENCE: 49

Phe Pro Ala Ile Ile Cys Lys Val Ser Lys Asn Cys
1               5                   10

<210> SEQ ID NO 50
<211> LENGTH: 12
<212> TYPE: PRT
<213> ORGANISM: Artificial Sequence
<220> FEATURE:
<223> OTHER INFORMATION: P8_CCH_N11K, 'synthetic' AMP

<400> SEQUENCE: 50

Phe Pro Ala Ile Ile Cys Lys Val Ser Lys Lys Cys
1               5                   10

<210> SEQ ID NO 51
<211> LENGTH: 15
<212> TYPE: PRT
<213> ORGANISM: Artificial Sequence
<220> FEATURE:
<223> OTHER INFORMATION: P9_CCH_2, 'synthetic' AMP

<400> SEQUENCE: 51

Phe Leu Thr Lys Pro Gly Met Thr Phe Gly Lys Leu Leu Gly Lys

```
<210> SEQ ID NO 52
<211> LENGTH: 15
<212> TYPE: PRT
<213> ORGANISM: Artificial Sequence
<220> FEATURE:
<223> OTHER INFORMATION: P10_CCH, 'natural' AMP

<400> SEQUENCE: 52

Ser Asn Arg Asp Phe Phe Lys Val Asn Ile Phe Arg Leu Cys Gly
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: P10_CCH_2, 'synthetic' AMP

<400> SEQUENCE: 53

Ser Asn Arg Lys Phe Phe Lys Val Arg Ile Phe Arg Leu Cys Gly
1               5                   10                  15

<210> SEQ ID NO 54
<211> LENGTH: 25
<212> TYPE: PRT
<213> ORGANISM: Artificial Sequence
<220> FEATURE:
<223> OTHER INFORMATION: P11_CCH, 'natural' AMP

<400> SEQUENCE: 54

Ala Leu Val Ala Lys Ile Gln Lys Phe Pro Val Phe Asn Thr Leu Lys
1               5                   10                  15

Leu Cys Lys Leu Glu Leu Glu Ile Ile
            20                  25

<210> SEQ ID NO 55
<211> LENGTH: 25
<212> TYPE: PRT
<213> ORGANISM: Artificial Sequence
<220> FEATURE:
<223> OTHER INFORMATION: P11_CCH_E21K_E23R, 'synthetic' AMP

<400> SEQUENCE: 55

Ala Leu Val Ala Lys Ile Gln Lys Phe Pro Val Phe Asn Thr Leu Lys
1               5                   10                  15

Leu Cys Lys Leu Lys Leu Arg Ile Ile
            20                  25

<210> SEQ ID NO 56
<211> LENGTH: 13
<212> TYPE: PRT
<213> ORGANISM: Artificial Sequence
<220> FEATURE:
<223> OTHER INFORMATION: P12_CCH, 'natural' AMP

<400> SEQUENCE: 56

Ile Ala Gly Gln Val Ala Ala Lys Gln Lys His Ile
1               5                   10

<210> SEQ ID NO 57
<211> LENGTH: 13
<212> TYPE: PRT
<213> ORGANISM: Artificial Sequence
<220> FEATURE:
```

```
<223> OTHER INFORMATION: P12_CCH2, 'synthetic' AMP

<400> SEQUENCE: 57

Ile Ala Gly Gln Lys Ala Arg Ala Lys Gln Lys His Ile
1               5                   10

<210> SEQ ID NO 58
<211> LENGTH: 20
<212> TYPE: PRT
<213> ORGANISM: Artificial Sequence
<220> FEATURE:
<223> OTHER INFORMATION: P13_CCH, 'natural' AMP

<400> SEQUENCE: 58

Ile Gln Arg Leu Pro Val Ile Asn Met Leu Lys Leu Trp Lys Leu Glu
1               5                   10                  15

Leu Glu Ile Ile
            20

<210> SEQ ID NO 59
<211> LENGTH: 20
<212> TYPE: PRT
<213> ORGANISM: Artificial Sequence
<220> FEATURE:
<223> OTHER INFORMATION: P13_CCH_N8K_E18K, 'synthetic' AMP

<400> SEQUENCE: 59

Ile Gln Arg Leu Pro Val Ile Lys Met Leu Lys Leu Trp Lys Leu Glu
1               5                   10                  15

Leu Lys Ile Ile
            20

<210> SEQ ID NO 60
<211> LENGTH: 21
<212> TYPE: PRT
<213> ORGANISM: Artificial Sequence
<220> FEATURE:
<223> OTHER INFORMATION: P14_CCH, 'natural' AMP

<400> SEQUENCE: 60

Ile Gln Arg Leu Pro Val Ile Val Ile Leu Pro Ser Leu Tyr Cys Val
1               5                   10                  15

Ile Cys Arg Thr Cys
            20

<210> SEQ ID NO 61
<211> LENGTH: 21
<212> TYPE: PRT
<213> ORGANISM: Artificial Sequence
<220> FEATURE:
<223> OTHER INFORMATION: P14_CCH_2, 'synthetic' AMP

<400> SEQUENCE: 61

Ile Gln Arg Leu Pro Val Ile Val Ile Leu Pro Ser Leu Tyr Cys Val
1               5                   10                  15

Ile Cys Arg Lys Lys
            20

<210> SEQ ID NO 62
<211> LENGTH: 35
<212> TYPE: PRT
<213> ORGANISM: Artificial Sequence
<220> FEATURE:
<223> OTHER INFORMATION: P15_CCH, 'natural' AMP
```

```
<400> SEQUENCE: 62

Leu Arg Cys Pro Thr Pro His Tyr Asn Phe Glu Asn Gly Ile Gly Asn
1               5                   10                  15

His Leu Met Trp Asn Ile Ile Trp Leu Asn Ala Gln Gln Met Ser Tyr
            20                  25                  30

Lys Asn Lys
        35

<210> SEQ ID NO 63
<211> LENGTH: 35
<212> TYPE: PRT
<213> ORGANISM: Artificial Sequence
<220> FEATURE:
<223> OTHER INFORMATION: P15_CCH_2, 'synthetic' AMP

<400> SEQUENCE: 63

Leu Arg Cys Pro Thr Pro His Tyr Arg Phe Glu Asn Gly Ile Gly Asn
1               5                   10                  15

His Leu Met Trp Asn Ile Ile Trp Leu Asn Ala Gln Gln Met Ser Tyr
            20                  25                  30

Cys Asn Lys
        35

<210> SEQ ID NO 64
<211> LENGTH: 25
<212> TYPE: PRT
<213> ORGANISM: Artificial Sequence
<220> FEATURE:
<223> OTHER INFORMATION: P16_CCH, 'natural' AMP

<400> SEQUENCE: 64

Ser Asn Arg Asp Phe Phe Met Val Asn Ile Phe Gly Leu Cys Gly Pro
1               5                   10                  15

Phe Gly Ile Met Glu Arg Lys Arg Arg
            20                  25

<210> SEQ ID NO 65
<211> LENGTH: 25
<212> TYPE: PRT
<213> ORGANISM: Artificial Sequence
<220> FEATURE:
<223> OTHER INFORMATION: P16_CCH_2, 'synthetic' AMP

<400> SEQUENCE: 65

Ser Asn Arg Lys Phe Phe Met Val Asn Ile Phe Gly Leu Cys Gly Pro
1               5                   10                  15

Phe Gly Ile Met Lys Arg Lys Arg Arg
            20                  25

<210> SEQ ID NO 66
<211> LENGTH: 12
<212> TYPE: PRT
<213> ORGANISM: Artificial Sequence
<220> FEATURE:
<223> OTHER INFORMATION: P1 variant AMP sequence
<220> FEATURE:
<221> NAME/KEY: MISC_FEATURE
<222> LOCATION: (1)..(9)
<223> OTHER INFORMATION: Xaa is any amino acid

<400> SEQUENCE: 66

Xaa Xaa Xaa Pro Xaa Xaa Xaa Xaa Xaa Gly Gly Lys
1               5                   10
```

```
<210> SEQ ID NO 67
<211> LENGTH: 12
<212> TYPE: PRT
<213> ORGANISM: Artificial Sequence
<220> FEATURE:
<223> OTHER INFORMATION: Group P1 variant AMP sequence
<220> FEATURE:
<221> NAME/KEY: MISC_FEATURE
<222> LOCATION: (5)..(9)
<223> OTHER INFORMATION: Xaa is any amino acid

<400> SEQUENCE: 67

Phe Tyr Phe Pro Xaa Xaa Xaa Xaa Xaa Gly Gly Lys
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Group P1 variant AMP sequence
<220> FEATURE:
<221> NAME/KEY: MISC_FEATURE
<222> LOCATION: (1)..(12)
<223> OTHER INFORMATION: Xaa is any amino acid

<400> SEQUENCE: 68

Xaa Tyr Phe Xaa Xaa Ser Arg Lys Xaa Xaa Xaa Xaa
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Group P1 variant AMP sequence
<220> FEATURE:
<221> NAME/KEY: MISC_FEATURE
<222> LOCATION: (2)..(12)
<223> OTHER INFORMATION: Xaa is any amino acid

<400> SEQUENCE: 69

Phe Xaa Phe Xaa Val Ser Arg Lys Xaa Xaa Xaa Xaa
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Group P1 variant AMP sequence
<220> FEATURE:
<221> NAME/KEY: MISC_FEATURE
<222> LOCATION: (1)..(11)
<223> OTHER INFORMATION: Xaa is any amino acid

<400> SEQUENCE: 70

Xaa Tyr Phe Xaa Xaa Xaa Xaa Lys Phe Xaa Xaa Lys
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Group P1 variant AMP sequence
<220> FEATURE:
<221> NAME/KEY: MISC_FEATURE
<222> LOCATION: (1)..(8)
<223> OTHER INFORMATION: Xaa is any amino acid
```

```
<400> SEQUENCE: 71

Xaa Xaa Xaa Xaa Xaa Xaa Xaa Xaa Phe Gly Gly Lys
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Group P1 variant AMP sequence
<220> FEATURE:
<221> NAME/KEY: MISC_FEATURE
<222> LOCATION: (2)..(12)
<223> OTHER INFORMATION: Xaa is any amino acid

<400> SEQUENCE: 72

Phe Tyr Xaa Pro Val Xaa Arg Xaa Phe Xaa Xaa Xaa
1               5                   10

<210> SEQ ID NO 73
<211> LENGTH: 26
<212> TYPE: PRT
<213> ORGANISM: Artificial Sequence
<220> FEATURE:
<223> OTHER INFORMATION: Group P2 variant AMP sequence
<220> FEATURE:
<221> NAME/KEY: MISC_FEATURE
<222> LOCATION: (5)..(22)
<223> OTHER INFORMATION: Xaa is any amino acid

<400> SEQUENCE: 73

Phe Phe Pro Arg Xaa Xaa Xaa Xaa Xaa Xaa Phe Leu Pro Thr Xaa
1               5                   10                  15

Xaa Xaa Xaa Xaa Xaa Xaa Ser Val Gly Asn
            20                  25

<210> SEQ ID NO 74
<211> LENGTH: 26
<212> TYPE: PRT
<213> ORGANISM: Artificial Sequence
<220> FEATURE:
<223> OTHER INFORMATION: Group P2 variant AMP sequence
<220> FEATURE:
<221> NAME/KEY: MISC_FEATURE
<222> LOCATION: (1)..(26)
<223> OTHER INFORMATION: Xaa is any amino acid

<400> SEQUENCE: 74

Xaa Xaa Xaa Xaa Val Leu Pro Leu Ala Asn Lys Xaa Xaa Xaa Xaa Ile
1               5                   10                  15

Tyr Cys Xaa Xaa Xaa Xaa Xaa Xaa Xaa Xaa
            20                  25

<210> SEQ ID NO 75
<211> LENGTH: 26
<212> TYPE: PRT
<213> ORGANISM: Artificial Sequence
<220> FEATURE:
<223> OTHER INFORMATION: Group P2 variant AMP sequence
<220> FEATURE:
<221> NAME/KEY: MISC_FEATURE
<222> LOCATION: (4)..(23)
<223> OTHER INFORMATION: Xaa is any amino acid

<400> SEQUENCE: 75

Phe Phe Pro Xaa Xaa Leu Pro Leu Ala Asn Xaa Xaa Leu Pro Xaa Xaa
1               5                   10                  15
```

```
Xaa Xaa Xaa Leu Pro Xaa Xaa Val Gly Asn
            20                  25

<210> SEQ ID NO 76
<211> LENGTH: 26
<212> TYPE: PRT
<213> ORGANISM: Artificial Sequence
<220> FEATURE:
<223> OTHER INFORMATION: Group P2 variant AMP sequence
<220> FEATURE:
<221> NAME/KEY: MISC_FEATURE
<222> LOCATION: (1)..(26)
<223> OTHER INFORMATION: Xaa is any amino acid

<400> SEQUENCE: 76

Xaa Xaa Pro Arg Val Leu Xaa Xaa Xaa Xaa Xaa Xaa Xaa Xaa Xaa Xaa
1               5                   10                  15

Xaa Xaa Xaa Xaa Pro Lys Ser Xaa Xaa Xaa
            20                  25

<210> SEQ ID NO 77
<211> LENGTH: 26
<212> TYPE: PRT
<213> ORGANISM: Artificial Sequence
<220> FEATURE:
<223> OTHER INFORMATION: Group P2 variant AMP sequence
<220> FEATURE:
<221> NAME/KEY: MISC_FEATURE
<222> LOCATION: (2)..(26)
<223> OTHER INFORMATION: Xaa is any amino acid

<400> SEQUENCE: 77

Phe Xaa Xaa Xaa Xaa Xaa Xaa Leu Ala Asn Lys Xaa Xaa Xaa Thr Ile
1               5                   10                  15

Tyr Cys Xaa Xaa Xaa Xaa Ser Val Xaa Xaa
            20                  25

<210> SEQ ID NO 78
<211> LENGTH: 26
<212> TYPE: PRT
<213> ORGANISM: Artificial Sequence
<220> FEATURE:
<223> OTHER INFORMATION: Group P2 variant AMP sequence
<220> FEATURE:
<221> NAME/KEY: MISC_FEATURE
<222> LOCATION: (3)..(25)
<223> OTHER INFORMATION: Xaa is any amino acid

<400> SEQUENCE: 78

Phe Phe Xaa Xaa Val Leu Pro Xaa Xaa Xaa Xaa Xaa Leu Xaa Thr Xaa
1               5                   10                  15

Tyr Cys Ala Leu Pro Lys Xaa Val Xaa Asn
            20                  25

<210> SEQ ID NO 79
<211> LENGTH: 26
<212> TYPE: PRT
<213> ORGANISM: Artificial Sequence
<220> FEATURE:
<223> OTHER INFORMATION: Group P2 variant AMP sequence
<220> FEATURE:
<221> NAME/KEY: MISC_FEATURE
<222> LOCATION: (1)..(26)
<223> OTHER INFORMATION: Xaa is any amino acid

<400> SEQUENCE: 79

Xaa Xaa Xaa Xaa Xaa Xaa Xaa Leu Ala Asn Xaa Phe Xaa Pro Xaa Ile
```

```
                1               5                   10                  15

Xaa Xaa Ala Leu Pro Lys Xaa Xaa Gly Xaa
            20                  25

<210> SEQ ID NO 80
<211> LENGTH: 32
<212> TYPE: PRT
<213> ORGANISM: Artificial Sequence
<220> FEATURE:
<223> OTHER INFORMATION: Group P3 variant AMP sequence
<220> FEATURE:
<221> NAME/KEY: MISC_FEATURE
<222> LOCATION: (4)..(27)
<223> OTHER INFORMATION: Xaa is any amino acid

<400> SEQUENCE: 80

Gly Leu Leu Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Cys Pro Pro Ser Ser
            20                  25                  30

<210> SEQ ID NO 81
<211> LENGTH: 32
<212> TYPE: PRT
<213> ORGANISM: Artificial Sequence
<220> FEATURE:
<223> OTHER INFORMATION: Group P3 variant AMP sequence
<220> FEATURE:
<221> NAME/KEY: MISC_FEATURE
<222> LOCATION: (1)..(31)
<223> OTHER INFORMATION: Xaa is any amino acid

<400> SEQUENCE: 81

Xaa Xaa Xaa Xaa Xaa Xaa Lys Xaa Xaa Xaa Lys Xaa Xaa Gly Xaa Leu
1               5                   10                  15

Met Xaa Xaa Xaa Xaa Xaa Xaa Met Xaa Gly Xaa Xaa Pro Pro Xaa Ser
            20                  25                  30

<210> SEQ ID NO 82
<211> LENGTH: 32
<212> TYPE: PRT
<213> ORGANISM: Artificial Sequence
<220> FEATURE:
<223> OTHER INFORMATION: Group P3 variant AMP sequence
<220> FEATURE:
<221> NAME/KEY: MISC_FEATURE
<222> LOCATION: (4)..(32)
<223> OTHER INFORMATION: Xaa is any amino acid

<400> SEQUENCE: 82

Gly Leu Leu Xaa Ile Ile Xaa Xaa Xaa Gly Xaa Thr Thr Gly Ile Leu
1               5                   10                  15

Met Xaa Xaa Leu Xaa Xaa Xaa Met Xaa Gly Xaa Xaa Pro Pro Xaa Xaa
            20                  25                  30

<210> SEQ ID NO 83
<211> LENGTH: 32
<212> TYPE: PRT
<213> ORGANISM: Artificial Sequence
<220> FEATURE:
<223> OTHER INFORMATION: Group P3 variant AMP sequence
<220> FEATURE:
<221> NAME/KEY: MISC_FEATURE
<222> LOCATION: (1)..(30)
<223> OTHER INFORMATION: Xaa is any amino acid

<400> SEQUENCE: 83
```

Xaa Leu Xaa Xaa Xaa Xaa Xaa Xaa Xaa Lys Xaa Xaa Xaa Xaa Xaa
1               5                   10                  15

Xaa Xaa Thr Leu Lys Cys Gln Met Thr Xaa Xaa Cys Xaa Xaa Ser Ser
            20                  25                  30

<210> SEQ ID NO 84
<211> LENGTH: 32
<212> TYPE: PRT
<213> ORGANISM: Artificial Sequence
<220> FEATURE:
<223> OTHER INFORMATION: Group P3 variant AMP sequence
<220> FEATURE:
<221> NAME/KEY: MISC_FEATURE
<222> LOCATION: (4)..(32)
<223> OTHER INFORMATION: Xaa is any amino acid

<400> SEQUENCE: 84

Gly Leu Leu Xaa Ile Ile Lys Xaa Thr Gly Lys Thr Thr Gly Ile Leu
1               5                   10                  15

Met Xaa Xaa Leu Lys Xaa Xaa Xaa Gly Xaa Xaa Xaa Xaa Xaa Xaa
            20                  25                  30

<210> SEQ ID NO 85
<211> LENGTH: 32
<212> TYPE: PRT
<213> ORGANISM: Artificial Sequence
<220> FEATURE:
<223> OTHER INFORMATION: Group P3 variant AMP sequence
<220> FEATURE:
<221> NAME/KEY: MISC_FEATURE
<222> LOCATION: (2)..(28)
<223> OTHER INFORMATION: Xaa is any amino acid

<400> SEQUENCE: 85

Gly Xaa Leu Xaa Ile Ile Lys Xaa Thr Gly Xaa Xaa Thr Xaa Ile Xaa
1               5                   10                  15

Met Xaa Thr Leu Lys Cys Gln Xaa Thr Gly Arg Xaa Pro Pro Ser Ser
            20                  25                  30

<210> SEQ ID NO 86
<211> LENGTH: 32
<212> TYPE: PRT
<213> ORGANISM: Artificial Sequence
<220> FEATURE:
<223> OTHER INFORMATION: Group P3 variant AMP sequence
<220> FEATURE:
<221> NAME/KEY: MISC_FEATURE
<222> LOCATION: (4)..(32)
<223> OTHER INFORMATION: Xaa is any amino acid

<400> SEQUENCE: 86

Gly Leu Leu Xaa Xaa Xaa Lys Xaa Thr Gly Lys Xaa Thr Xaa Ile Xaa
1               5                   10                  15

Xaa Xaa Thr Leu Lys Xaa Gln Xaa Thr Gly Arg Xaa Xaa Xaa Xaa Xaa
            20                  25                  30

<210> SEQ ID NO 87
<211> LENGTH: 32
<212> TYPE: PRT
<213> ORGANISM: Artificial Sequence
<220> FEATURE:
<223> OTHER INFORMATION: Group P3 variant AMP sequence
<220> FEATURE:
<221> NAME/KEY: MISC_FEATURE
<222> LOCATION: (1)..(32)
<223> OTHER INFORMATION: Xaa is any amino acid

<400> SEQUENCE: 87

```
Xaa Xaa Xaa Xaa Ile Ile Xaa Xaa Thr Xaa Xaa Thr Xaa Gly Xaa Leu
1               5                   10                  15

Xaa Xaa Thr Xaa Xaa Cys Gln Xaa Thr Xaa Arg Xaa Xaa Xaa Xaa
            20                  25                  30
```

<210> SEQ ID NO 88
<211> LENGTH: 31
<212> TYPE: PRT
<213> ORGANISM: Artificial Sequence
<220> FEATURE:
<223> OTHER INFORMATION: Group P4 variant AMP sequence
<220> FEATURE:
<221> NAME/KEY: MISC_FEATURE
<222> LOCATION: (4)..(31)
<223> OTHER INFORMATION: Xaa is any amino acid

<400> SEQUENCE: 88

```
Gly Leu Leu Xaa Ile Ile Xaa Xaa Xaa Gly Xaa Xaa Xaa Xaa Xaa Xaa
1               5                   10                  15

Ile Leu Xaa Xaa Leu Xaa Xaa Xaa Leu Ala Gly Gly Xaa Xaa Xaa
            20                  25                  30
```

<210> SEQ ID NO 89
<211> LENGTH: 31
<212> TYPE: PRT
<213> ORGANISM: Artificial Sequence
<220> FEATURE:
<223> OTHER INFORMATION: Group P4 variant AMP sequence
<220> FEATURE:
<221> NAME/KEY: MISC_FEATURE
<222> LOCATION: (4)..(29)
<223> OTHER INFORMATION: Xaa is any amino acid

<400> SEQUENCE: 89

```
Gly Leu Leu Xaa Xaa Xaa Lys Thr Thr Gly Lys Xaa Phe Ala Val Lys
1               5                   10                  15

Ile Leu Xaa Asn Leu Xaa Xaa Xaa Xaa Xaa Xaa Xaa Xaa Pro Pro
            20                  25                  30
```

<210> SEQ ID NO 90
<211> LENGTH: 31
<212> TYPE: PRT
<213> ORGANISM: Artificial Sequence
<220> FEATURE:
<223> OTHER INFORMATION: Group P4 variant AMP sequence
<220> FEATURE:
<221> NAME/KEY: MISC_FEATURE
<222> LOCATION: (1)..(31)
<223> OTHER INFORMATION: Xaa is any amino acid

<400> SEQUENCE: 90

```
Xaa Xaa Xaa Xaa Ile Ile Lys Thr Xaa Xaa Xaa Xaa Phe Ala Val Xaa
1               5                   10                  15

Xaa Xaa Xaa Xaa Xaa Lys Cys Lys Leu Ala Gly Gly Xaa Xaa Xaa
            20                  25                  30
```

<210> SEQ ID NO 91
<211> LENGTH: 31
<212> TYPE: PRT
<213> ORGANISM: Artificial Sequence
<220> FEATURE:
<223> OTHER INFORMATION: Group P4 variant AMP sequence
<220> FEATURE:
<221> NAME/KEY: MISC_FEATURE
<222> LOCATION: (1)..(28)
<223> OTHER INFORMATION: Xaa is any amino acid -continued

<400> SEQUENCE: 91

Xaa Xaa Xaa Xaa Ile Ile Xaa Xaa Xaa Lys Xaa Xaa Xaa Xaa Lys
1               5                   10                  15

Xaa Xaa Xaa Asn Leu Lys Cys Lys Xaa Xaa Xaa Xaa Cys Pro Pro
            20                  25                  30

<210> SEQ ID NO 92
<211> LENGTH: 31
<212> TYPE: PRT
<213> ORGANISM: Artificial Sequence
<220> FEATURE:
<223> OTHER INFORMATION: Group P4 variant AMP sequence
<220> FEATURE:
<221> NAME/KEY: MISC_FEATURE
<222> LOCATION: (4)..(31)
<223> OTHER INFORMATION: Xaa is any amino acid

<400> SEQUENCE: 92

Gly Leu Leu Xaa Xaa Xaa Lys Thr Thr Gly Xaa Xaa Xaa Xaa Xaa
1               5                   10                  15

Xaa Leu Xaa Asn Leu Lys Cys Xaa Xaa Ala Xaa Xaa Cys Xaa Xaa
            20                  25                  30

<210> SEQ ID NO 93
<211> LENGTH: 31
<212> TYPE: PRT
<213> ORGANISM: Artificial Sequence
<220> FEATURE:
<223> OTHER INFORMATION: Group P4 variant AMP sequence
<220> FEATURE:
<221> NAME/KEY: MISC_FEATURE
<222> LOCATION: (4)..(29)
<223> OTHER INFORMATION: Xaa is any amino acid

<400> SEQUENCE: 93

Gly Leu Leu Xaa Xaa Xaa Lys Xaa Xaa Xaa Xaa Phe Ala Val Xaa
1               5                   10                  15

Xaa Leu Xaa Xaa Leu Xaa Xaa Xaa Xaa Xaa Xaa Xaa Pro Pro
            20                  25                  30

<210> SEQ ID NO 94
<211> LENGTH: 24
<212> TYPE: PRT
<213> ORGANISM: Artificial Sequence
<220> FEATURE:
<223> OTHER INFORMATION: Group P5 variant AMP sequence
<220> FEATURE:
<221> NAME/KEY: MISC_FEATURE
<222> LOCATION: (1)..(21)
<223> OTHER INFORMATION: Xaa is any amino acid

<400> SEQUENCE: 94

Xaa Xaa Xaa Xaa Xaa Xaa Xaa Leu Ala Ala Lys Xaa Xaa Xaa Ser Leu
1               5                   10                  15

Val Xaa Xaa Xaa Xaa Lys Lys Cys
            20

<210> SEQ ID NO 95
<211> LENGTH: 24
<212> TYPE: PRT
<213> ORGANISM: Artificial Sequence
<220> FEATURE:
<223> OTHER INFORMATION: Group P5 variant AMP sequence
<220> FEATURE:
<221> NAME/KEY: MISC_FEATURE
<222> LOCATION: (1)..(24)
<223> OTHER INFORMATION: Xaa is any amino acid

<400> SEQUENCE: 95

Xaa Phe Pro Ile Ile Ala Xaa Leu Ala Ala Xaa Val Ile Pro Xaa Leu
1               5                   10                  15

Val Xaa Ala Val Thr Xaa Xaa Xaa
            20

<210> SEQ ID NO 96
<211> LENGTH: 24
<212> TYPE: PRT
<213> ORGANISM: Artificial Sequence
<220> FEATURE:
<223> OTHER INFORMATION: Group P5 variant AMP sequence
<220> FEATURE:
<221> NAME/KEY: MISC_FEATURE
<222> LOCATION: (4)..(24)
<223> OTHER INFORMATION: Xaa is any amino acid

<400> SEQUENCE: 96

Phe Phe Pro Xaa Xaa Ala Xaa Xaa Xaa Lys Xaa Xaa Pro Xaa Xaa
1               5                   10                  15

Xaa Xaa Xaa Xaa Xaa Xaa Xaa Xaa
            20

<210> SEQ ID NO 97
<211> LENGTH: 24
<212> TYPE: PRT
<213> ORGANISM: Artificial Sequence
<220> FEATURE:
<223> OTHER INFORMATION: Group P5 variant AMP sequence
<220> FEATURE:
<221> NAME/KEY: MISC_FEATURE
<222> LOCATION: (1)..(24)
<223> OTHER INFORMATION: Xaa is any amino acid

<400> SEQUENCE: 97

Xaa Xaa Xaa Xaa Xaa Xaa Xaa Leu Ala Ala Xaa Val Ile Pro Xaa Leu
1               5                   10                  15

Xaa Xaa Xaa Xaa Thr Xaa Xaa Xaa
            20

<210> SEQ ID NO 98
<211> LENGTH: 24
<212> TYPE: PRT
<213> ORGANISM: Artificial Sequence
<220> FEATURE:
<223> OTHER INFORMATION: Group P5 variant AMP sequence
<220> FEATURE:
<221> NAME/KEY: MISC_FEATURE
<222> LOCATION: (7)..(16)
<223> OTHER INFORMATION: Xaa is any amino acid

<400> SEQUENCE: 98

Phe Phe Pro Ile Ile Ala Xaa Xaa Xaa Xaa Xaa Xaa Xaa Xaa Xaa Xaa
1               5                   10                  15

Val Cys Ala Val Thr Lys Lys Cys
            20

<210> SEQ ID NO 99
<211> LENGTH: 24
<212> TYPE: PRT
<213> ORGANISM: Artificial Sequence
<220> FEATURE:
<223> OTHER INFORMATION: Group P5 variant AMP sequence
<220> FEATURE:
<221> NAME/KEY: MISC_FEATURE
<222> LOCATION: (1)..(19)

<223> OTHER INFORMATION: Xaa is any amino acid

<400> SEQUENCE: 99

Xaa Xaa Xaa Ile Ile Xaa Arg Xaa Xaa Xaa Lys Val Ile Xaa Ser Xaa
1               5                   10                  15

Val Cys Xaa Val Thr Lys Lys Cys
            20

<210> SEQ ID NO 100
<211> LENGTH: 24
<212> TYPE: PRT
<213> ORGANISM: Artificial Sequence
<220> FEATURE:
<223> OTHER INFORMATION: Group P5 variant AMP sequence
<220> FEATURE:
<221> NAME/KEY: MISC_FEATURE
<222> LOCATION: (11)..(24)
<223> OTHER INFORMATION: Xaa is any amino acid

<400> SEQUENCE: 100

Phe Phe Pro Ile Ile Ala Arg Leu Ala Ala Xaa Val Ile Xaa Ser Leu
1               5                   10                  15

Xaa Cys Ala Val Xaa Xaa Xaa Xaa
            20

<210> SEQ ID NO 101
<211> LENGTH: 31
<212> TYPE: PRT
<213> ORGANISM: Artificial Sequence
<220> FEATURE:
<223> OTHER INFORMATION: Group P6 variant AMP sequence
<220> FEATURE:
<221> NAME/KEY: MISC_FEATURE
<222> LOCATION: (8)..(26)
<223> OTHER INFORMATION: Xaa is any amino acid

<400> SEQUENCE: 101

Gly Leu Trp Glu Thr Ile Lys Xaa Xaa Xaa Lys Xaa Xaa Xaa Xaa Xaa
1               5                   10                  15

Xaa Xaa Xaa Lys Xaa Xaa Xaa Xaa Xaa Xaa Gly Gly Cys Pro Pro
            20                  25                  30

<210> SEQ ID NO 102
<211> LENGTH: 31
<212> TYPE: PRT
<213> ORGANISM: Artificial Sequence
<220> FEATURE:
<223> OTHER INFORMATION: Group P6 variant AMP sequence
<220> FEATURE:
<221> NAME/KEY: MISC_FEATURE
<222> LOCATION: (1)..(31)
<223> OTHER INFORMATION: Xaa is any amino acid

<400> SEQUENCE: 102

Xaa Xaa Xaa Xaa Xaa Xaa Xaa Thr Thr Gly Xaa Xaa Xaa Xaa Xaa Xaa
1               5                   10                  15

Xaa Xaa Xaa Xaa Xaa Lys Cys Lys Xaa Xaa Xaa Xaa Cys Xaa Xaa
            20                  25                  30

<210> SEQ ID NO 103
<211> LENGTH: 31
<212> TYPE: PRT
<213> ORGANISM: Artificial Sequence
<220> FEATURE:
<223> OTHER INFORMATION: Group P6 variant AMP sequence
<220> FEATURE:
<221> NAME/KEY: MISC_FEATURE
<222> LOCATION: (1)..(29)
<223> OTHER INFORMATION: Xaa is any amino acid

<400> SEQUENCE: 103

Xaa Xaa Xaa Xaa Thr Ile Xaa Xaa Xaa Gly Xaa Xaa Ile Ala Leu Xaa
1               5                   10                  15

Leu Leu Xaa Xaa Ile Xaa Xaa Xaa Ile Ala Xaa Xaa Xaa Pro Pro
            20                  25                  30

<210> SEQ ID NO 104
<211> LENGTH: 31
<212> TYPE: PRT
<213> ORGANISM: Artificial Sequence
<220> FEATURE:
<223> OTHER INFORMATION: Group P6 variant AMP sequence
<220> FEATURE:
<221> NAME/KEY: MISC_FEATURE
<222> LOCATION: (6)..(29)
<223> OTHER INFORMATION: Xaa is any amino acid

<400> SEQUENCE: 104

Gly Leu Trp Glu Thr Xaa Lys Thr Thr Xaa Xaa Ser Xaa Xaa Leu Asn
1               5                   10                  15

Leu Leu Asp Lys Ile Xaa Xaa Lys Ile Ala Xaa Xaa Xaa Pro Pro
            20                  25                  30

<210> SEQ ID NO 105
<211> LENGTH: 31
<212> TYPE: PRT
<213> ORGANISM: Artificial Sequence
<220> FEATURE:
<223> OTHER INFORMATION: Group P6 variant AMP sequence
<220> FEATURE:
<221> NAME/KEY: MISC_FEATURE
<222> LOCATION: (1)..(31)
<223> OTHER INFORMATION: Xaa is any amino acid

<400> SEQUENCE: 105

Xaa Xaa Xaa Xaa Xaa Ile Lys Xaa Xaa Gly Lys Ser Ile Ala Leu Xaa
1               5                   10                  15

Xaa Xaa Xaa Lys Xaa Lys Xaa Lys Xaa Xaa Gly Gly Xaa Xaa Xaa
            20                  25                  30

<210> SEQ ID NO 106
<211> LENGTH: 31
<212> TYPE: PRT
<213> ORGANISM: Artificial Sequence
<220> FEATURE:
<223> OTHER INFORMATION: Group P6 variant AMP sequence
<220> FEATURE:
<221> NAME/KEY: MISC_FEATURE
<222> LOCATION: (1)..(31)
<223> OTHER INFORMATION: Xaa is any amino acid

<400> SEQUENCE: 106

Xaa Xaa Xaa Xaa Xaa Xaa Xaa Xaa Xaa Xaa Lys Ser Ile Ala Xaa Asn
1               5                   10                  15

Leu Leu Xaa Xaa Ile Xaa Cys Xaa Ile Ala Gly Gly Xaa Xaa Xaa
            20                  25                  30

<210> SEQ ID NO 107
<211> LENGTH: 26
<212> TYPE: PRT
<213> ORGANISM: Artificial Sequence
<220> FEATURE:
<223> OTHER INFORMATION: Group P7 variant AMP sequence
<220> FEATURE:

<221> NAME/KEY: MISC_FEATURE
<222> LOCATION: (5)..(26)
<223> OTHER INFORMATION: Xaa is any amino acid

<400> SEQUENCE: 107

Ala Thr Ala Trp Xaa Ile Xaa Xaa Xaa Gly Met Xaa Xaa Ile Ile Xaa
1               5                   10                  15

Ile Xaa Ile Xaa Xaa Leu Xaa Gly Xaa Xaa
            20                  25

<210> SEQ ID NO 108
<211> LENGTH: 26
<212> TYPE: PRT
<213> ORGANISM: Artificial Sequence
<220> FEATURE:
<223> OTHER INFORMATION: Group P7 variant AMP sequence
<220> FEATURE:
<221> NAME/KEY: MISC_FEATURE
<222> LOCATION: (1)..(22)
<223> OTHER INFORMATION: Xaa is any amino acid

<400> SEQUENCE: 108

Xaa Xaa Xaa Trp Xaa Ile Xaa Xaa Xaa Gly Met Gln Xaa Xaa Xaa Xaa
1               5                   10                  15

Xaa Xaa Xaa Xaa Xaa Xaa Cys Gly Lys Gln
            20                  25

<210> SEQ ID NO 109
<211> LENGTH: 26
<212> TYPE: PRT
<213> ORGANISM: Artificial Sequence
<220> FEATURE:
<223> OTHER INFORMATION: Group P7 variant AMP sequence
<220> FEATURE:
<221> NAME/KEY: MISC_FEATURE
<222> LOCATION: (1)..(26)
<223> OTHER INFORMATION: Xaa is any amino acid

<400> SEQUENCE: 109

Xaa Xaa Xaa Xaa Xaa Xaa Pro Pro Pro Xaa Xaa Gln Pro Xaa Xaa Pro
1               5                   10                  15

Xaa Xaa Xaa Xaa Pro Xaa Xaa Xaa Xaa Xaa
            20                  25

<210> SEQ ID NO 110
<211> LENGTH: 26
<212> TYPE: PRT
<213> ORGANISM: Artificial Sequence
<220> FEATURE:
<223> OTHER INFORMATION: Group P7 variant AMP sequence
<220> FEATURE:
<221> NAME/KEY: MISC_FEATURE
<222> LOCATION: (4)..(24)
<223> OTHER INFORMATION: Xaa is any amino acid

<400> SEQUENCE: 110

Ala Thr Ala Xaa Xaa Xaa Pro Pro Pro Xaa Xaa Xaa Pro Xaa Xaa Pro
1               5                   10                  15

Xaa Xaa Xaa Xaa Pro Xaa Cys Xaa Lys Gln
            20                  25

<210> SEQ ID NO 111
<211> LENGTH: 26
<212> TYPE: PRT
<213> ORGANISM: Artificial Sequence
<220> FEATURE:
<223> OTHER INFORMATION: Group P7 variant AMP sequence

```
<220> FEATURE:
<221> NAME/KEY: MISC_FEATURE
<222> LOCATION: (1)..(26)
<223> OTHER INFORMATION: Xaa is any amino acid

<400> SEQUENCE: 111

Xaa Xaa Xaa Trp Xaa Ile Xaa Xaa Xaa Gly Met Xaa Xaa Xaa Xaa
1               5                   10                  15

Ile Xaa Ile Xaa Xaa Leu Xaa Gly Xaa Xaa
            20                  25

<210> SEQ ID NO 112
<211> LENGTH: 26
<212> TYPE: PRT
<213> ORGANISM: Artificial Sequence
<220> FEATURE:
<223> OTHER INFORMATION: Group P7 variant AMP sequence
<220> FEATURE:
<221> NAME/KEY: MISC_FEATURE
<222> LOCATION: (1)..(26)
<223> OTHER INFORMATION: Xaa is any amino acid

<400> SEQUENCE: 112

Xaa Xaa Xaa Xaa Xaa Xaa Xaa Xaa Xaa Xaa Xaa Xaa Pro Xaa Xaa Pro
1               5                   10                  15

Xaa Xaa Ile Xaa Xaa Leu Xaa Gly Xaa Xaa
            20                  25

<210> SEQ ID NO 113
<211> LENGTH: 26
<212> TYPE: PRT
<213> ORGANISM: Artificial Sequence
<220> FEATURE:
<223> OTHER INFORMATION: Group P7 variant AMP sequence
<220> FEATURE:
<221> NAME/KEY: MISC_FEATURE
<222> LOCATION: (4)..(24)
<223> OTHER INFORMATION: Xaa is any amino acid

<400> SEQUENCE: 113

Ala Thr Ala Xaa Arg Xaa Xaa Xaa Xaa Xaa Xaa Gln Xaa Ile Ile Xaa
1               5                   10                  15

Ile Arg Ile Arg Xaa Leu Cys Xaa Lys Gln
            20                  25

<210> SEQ ID NO 114
<211> LENGTH: 12
<212> TYPE: PRT
<213> ORGANISM: Artificial Sequence
<220> FEATURE:
<223> OTHER INFORMATION: Group P8 variant AMP sequence
<220> FEATURE:
<221> NAME/KEY: MISC_FEATURE
<222> LOCATION: (6)..(12)
<223> OTHER INFORMATION: Xaa is any amino acid

<400> SEQUENCE: 114

Phe Pro Ala Ile Ile Xaa Xaa Xaa Xaa Xaa Xaa Xaa
1               5                   10

<210> SEQ ID NO 115
<211> LENGTH: 12
<212> TYPE: PRT
<213> ORGANISM: Artificial Sequence
<220> FEATURE:
<223> OTHER INFORMATION: Group P8 variant AMP sequence
<220> FEATURE:
<221> NAME/KEY: MISC_FEATURE
```

```
<222> LOCATION: (2)..(11)
<223> OTHER INFORMATION: Xaa is any amino acid

<400> SEQUENCE: 115

Phe Xaa Xaa Xaa Xaa Cys Xaa Xaa Xaa Lys Xaa Cys
1               5                   10

<210> SEQ ID NO 116
<211> LENGTH: 12
<212> TYPE: PRT
<213> ORGANISM: Artificial Sequence
<220> FEATURE:
<223> OTHER INFORMATION: Group P8 variant AMP sequence
<220> FEATURE:
<221> NAME/KEY: MISC_FEATURE
<222> LOCATION: (1)..(12)
<223> OTHER INFORMATION: Xaa is any amino acid

<400> SEQUENCE: 116

Xaa Xaa Ala Ile Ile Xaa Xaa Val Ser Lys Xaa Xaa
1               5                   10

<210> SEQ ID NO 117
<211> LENGTH: 12
<212> TYPE: PRT
<213> ORGANISM: Artificial Sequence
<220> FEATURE:
<223> OTHER INFORMATION: Group P8 variant AMP sequence
<220> FEATURE:
<221> NAME/KEY: MISC_FEATURE
<222> LOCATION: (1)..(12)
<223> OTHER INFORMATION: Xaa is any amino acid

<400> SEQUENCE: 117

Xaa Pro Ala Xaa Xaa Cys Lys Xaa Xaa Xaa Xaa Xaa
1               5                   10

<210> SEQ ID NO 118
<211> LENGTH: 12
<212> TYPE: PRT
<213> ORGANISM: Artificial Sequence
<220> FEATURE:
<223> OTHER INFORMATION: Group P8 variant AMP sequence
<220> FEATURE:
<221> NAME/KEY: MISC_FEATURE
<222> LOCATION: (3)..(7)
<223> OTHER INFORMATION: Xaa is any amino acid

<400> SEQUENCE: 118

Phe Pro Xaa Xaa Xaa Xaa Xaa Val Ser Lys Asn Cys
1               5                   10

<210> SEQ ID NO 119
<211> LENGTH: 12
<212> TYPE: PRT
<213> ORGANISM: Artificial Sequence
<220> FEATURE:
<223> OTHER INFORMATION: Group P8 variant AMP sequence
<220> FEATURE:
<221> NAME/KEY: MISC_FEATURE
<222> LOCATION: (1)..(12)
<223> OTHER INFORMATION: Xaa is any amino acid

<400> SEQUENCE: 119

Xaa Xaa Xaa Ile Ile Cys Lys Val Ser Xaa Asn Xaa
1               5                   10

<210> SEQ ID NO 120
<211> LENGTH: 15
```

```
<212> TYPE: PRT
<213> ORGANISM: Artificial Sequence
<220> FEATURE:
<223> OTHER INFORMATION: Group P9 variant AMP sequence
<220> FEATURE:
<221> NAME/KEY: MISC_FEATURE
<222> LOCATION: (5)..(15)
<223> OTHER INFORMATION: Xaa is any amino acid

<400> SEQUENCE: 120

Phe Leu Thr Phe Xaa Gly Xaa Xaa Phe Gly Xaa Xaa Xaa Gly Xaa
1               5                   10                  15

<210> SEQ ID NO 121
<211> LENGTH: 15
<212> TYPE: PRT
<213> ORGANISM: Artificial Sequence
<220> FEATURE:
<223> OTHER INFORMATION: Group P9 variant AMP sequence
<220> FEATURE:
<221> NAME/KEY: MISC_FEATURE
<222> LOCATION: (1)..(15)
<223> OTHER INFORMATION: Xaa is any amino acid

<400> SEQUENCE: 121

Xaa Xaa Xaa Xaa Pro Gly Met Xaa Phe Xaa Xaa Leu Leu Xaa Xaa
1               5                   10                  15

<210> SEQ ID NO 122
<211> LENGTH: 15
<212> TYPE: PRT
<213> ORGANISM: Artificial Sequence
<220> FEATURE:
<223> OTHER INFORMATION: Group P9 variant AMP sequence
<220> FEATURE:
<221> NAME/KEY: MISC_FEATURE
<222> LOCATION: (1)..(14)
<223> OTHER INFORMATION: Xaa is any amino acid

<400> SEQUENCE: 122

Xaa Xaa Xaa Xaa Pro Gly Met Xaa Xaa Xaa Lys Xaa Xaa Xaa Lys
1               5                   10                  15

<210> SEQ ID NO 123
<211> LENGTH: 15
<212> TYPE: PRT
<213> ORGANISM: Artificial Sequence
<220> FEATURE:
<223> OTHER INFORMATION: Group P9 variant AMP sequence
<220> FEATURE:
<221> NAME/KEY: MISC_FEATURE
<222> LOCATION: (5)..(15)
<223> OTHER INFORMATION: Xaa is any amino acid

<400> SEQUENCE: 123

Phe Leu Thr Phe Xaa Xaa Xaa Xaa Xaa Xaa Xaa Leu Leu Gly Xaa
1               5                   10                  15

<210> SEQ ID NO 124
<211> LENGTH: 15
<212> TYPE: PRT
<213> ORGANISM: Artificial Sequence
<220> FEATURE:
<223> OTHER INFORMATION: Group P9 variant AMP sequence
<220> FEATURE:
<221> NAME/KEY: MISC_FEATURE
<222> LOCATION: (2)..(14)
<223> OTHER INFORMATION: Xaa is any amino acid

<400> SEQUENCE: 124
```

```
Phe Xaa Xaa Phe Xaa Xaa Xaa Thr Phe Gly Lys Xaa Xaa Xaa Lys
1               5                   10                  15
```

<210> SEQ ID NO 125
<211> LENGTH: 15
<212> TYPE: PRT
<213> ORGANISM: Artificial Sequence
<220> FEATURE:
<223> OTHER INFORMATION: Group P9 variant AMP sequence
<220> FEATURE:
<221> NAME/KEY: MISC_FEATURE
<222> LOCATION: (1)..(7)
<223> OTHER INFORMATION: Xaa is any amino acid

<400> SEQUENCE: 125

```
Xaa Leu Thr Xaa Xaa Xaa Xaa Thr Phe Gly Lys Leu Leu Gly Lys
1               5                   10                  15
```

<210> SEQ ID NO 126
<211> LENGTH: 15
<212> TYPE: PRT
<213> ORGANISM: Artificial Sequence
<220> FEATURE:
<223> OTHER INFORMATION: Group P10 variant AMP sequence
<220> FEATURE:
<221> NAME/KEY: MISC_FEATURE
<222> LOCATION: (1)..(15)
<223> OTHER INFORMATION: Xaa is any amino acid

<400> SEQUENCE: 126

```
Xaa Xaa Xaa Xaa Phe Phe Xaa Val Asn Ile Phe Xaa Leu Xaa Xaa
1               5                   10                  15
```

<210> SEQ ID NO 127
<211> LENGTH: 15
<212> TYPE: PRT
<213> ORGANISM: Artificial Sequence
<220> FEATURE:
<223> OTHER INFORMATION: Group P10 variant AMP sequence
<220> FEATURE:
<221> NAME/KEY: MISC_FEATURE
<222> LOCATION: (3)..(15)
<223> OTHER INFORMATION: Xaa is any amino acid

<400> SEQUENCE: 127

```
Ser Asn Xaa Xaa Xaa Xaa Xaa Val Xaa Xaa Xaa Arg Xaa Xaa Xaa
1               5                   10                  15
```

<210> SEQ ID NO 128
<211> LENGTH: 15
<212> TYPE: PRT
<213> ORGANISM: Artificial Sequence
<220> FEATURE:
<223> OTHER INFORMATION: Group P10 variant AMP sequence
<220> FEATURE:
<221> NAME/KEY: MISC_FEATURE
<222> LOCATION: (1)..(12)
<223> OTHER INFORMATION: Xaa is any amino acid

<400> SEQUENCE: 128

```
Xaa Xaa Xaa Xaa Phe Phe Xaa Xaa Xaa Ile Phe Xaa Leu Cys Gly
1               5                   10                  15
```

<210> SEQ ID NO 129
<211> LENGTH: 15
<212> TYPE: PRT
<213> ORGANISM: Artificial Sequence
<220> FEATURE:
<223> OTHER INFORMATION: Group P10 variant AMP sequence
<220> FEATURE:

```
<221> NAME/KEY: MISC_FEATURE
<222> LOCATION: (3)..(12)
<223> OTHER INFORMATION: Xaa is any amino acid

<400> SEQUENCE: 129

Ser Asn Xaa Xaa Xaa Xaa Lys Xaa Xaa Xaa Xaa Xaa Leu Cys Gly
1               5                   10                  15

<210> SEQ ID NO 130
<211> LENGTH: 15
<212> TYPE: PRT
<213> ORGANISM: Artificial Sequence
<220> FEATURE:
<223> OTHER INFORMATION: Group P10 variant AMP sequence
<220> FEATURE:
<221> NAME/KEY: MISC_FEATURE
<222> LOCATION: (1)..(15)
<223> OTHER INFORMATION: Xaa is any amino acid

<400> SEQUENCE: 130

Xaa Xaa Arg Xaa Xaa Xaa Lys Val Asn Ile Phe Xaa Xaa Cys Xaa
1               5                   10                  15

<210> SEQ ID NO 131
<211> LENGTH: 15
<212> TYPE: PRT
<213> ORGANISM: Artificial Sequence
<220> FEATURE:
<223> OTHER INFORMATION: Group P10 variant AMP sequence
<220> FEATURE:
<221> NAME/KEY: MISC_FEATURE
<222> LOCATION: (2)..(14)
<223> OTHER INFORMATION: Xaa is any amino acid

<400> SEQUENCE: 131

Ser Xaa Xaa Xaa Phe Phe Xaa Val Xaa Ile Xaa Xaa Xaa Xaa Gly
1               5                   10                  15

<210> SEQ ID NO 132
<211> LENGTH: 15
<212> TYPE: PRT
<213> ORGANISM: Artificial Sequence
<220> FEATURE:
<223> OTHER INFORMATION: Group P10 variant AMP sequence
<220> FEATURE:
<221> NAME/KEY: MISC_FEATURE
<222> LOCATION: (2)..(15)
<223> OTHER INFORMATION: Xaa is any amino acid

<400> SEQUENCE: 132

Ser Xaa Arg Asp Phe Phe Lys Xaa Asn Xaa Xaa Arg Xaa Cys Xaa
1               5                   10                  15

<210> SEQ ID NO 133
<211> LENGTH: 25
<212> TYPE: PRT
<213> ORGANISM: Artificial Sequence
<220> FEATURE:
<223> OTHER INFORMATION: Group P11 variant AMP sequence
<220> FEATURE:
<221> NAME/KEY: MISC_FEATURE
<222> LOCATION: (1)..(25)
<223> OTHER INFORMATION: Xaa is any amino acid

<400> SEQUENCE: 133

Xaa Xaa Xaa Xaa Xaa Ile Gln Lys Xaa Xaa Xaa Xaa Asn Thr Leu Lys
1               5                   10                  15

Xaa Xaa Lys Xaa Xaa Leu Xaa Xaa Xaa
            20                  25
```

<210> SEQ ID NO 134
<211> LENGTH: 25
<212> TYPE: PRT
<213> ORGANISM: Artificial Sequence
<220> FEATURE:
<223> OTHER INFORMATION: Group P11 variant AMP sequence
<220> FEATURE:
<221> NAME/KEY: MISC_FEATURE
<222> LOCATION: (6)..(25)
<223> OTHER INFORMATION: Xaa is any amino acid

<400> SEQUENCE: 134

Ala Leu Val Ala Lys Xaa Xaa Xaa Phe Pro Val Phe Xaa Xaa Xaa Xaa
1               5                   10                  15

Leu Cys Xaa Leu Xaa Xaa Xaa Xaa Xaa
            20                  25

<210> SEQ ID NO 135
<211> LENGTH: 25
<212> TYPE: PRT
<213> ORGANISM: Artificial Sequence
<220> FEATURE:
<223> OTHER INFORMATION: Group P11 variant AMP sequence
<220> FEATURE:
<221> NAME/KEY: MISC_FEATURE
<222> LOCATION: (9)..(23)
<223> OTHER INFORMATION: Xaa is any amino acid

<400> SEQUENCE: 135

Ala Leu Val Ala Lys Ile Gln Lys Xaa Xaa Xaa Xaa Xaa Xaa Xaa Xaa
1               5                   10                  15

Xaa Xaa Lys Leu Xaa Xaa Xaa Ile Ile
            20                  25

<210> SEQ ID NO 136
<211> LENGTH: 25
<212> TYPE: PRT
<213> ORGANISM: Artificial Sequence
<220> FEATURE:
<223> OTHER INFORMATION: Group P11 variant AMP sequence
<220> FEATURE:
<221> NAME/KEY: MISC_FEATURE
<222> LOCATION: (1)..(25)
<223> OTHER INFORMATION: Xaa is any amino acid

<400> SEQUENCE: 136

Xaa Xaa Xaa Xaa Xaa Xaa Xaa Lys Xaa Pro Xaa Xaa Asn Thr Leu Lys
1               5                   10                  15

Xaa Cys Lys Xaa Glu Xaa Glu Xaa Xaa
            20                  25

<210> SEQ ID NO 137
<211> LENGTH: 25
<212> TYPE: PRT
<213> ORGANISM: Artificial Sequence
<220> FEATURE:
<223> OTHER INFORMATION: Group P11 variant AMP sequence
<220> FEATURE:
<221> NAME/KEY: MISC_FEATURE
<222> LOCATION: (1)..(25)
<223> OTHER INFORMATION: Xaa is any amino acid

<400> SEQUENCE: 137

Xaa Xaa Xaa Xaa Xaa Xaa Gln Xaa Phe Xaa Val Phe Xaa Thr Leu Lys
1               5                   10                  15

Leu Xaa Lys Leu Xaa Leu Xaa Xaa Xaa 20                  25

<210> SEQ ID NO 138
<211> LENGTH: 25
<212> TYPE: PRT
<213> ORGANISM: Artificial Sequence
<220> FEATURE:
<223> OTHER INFORMATION: Group P11 variant AMP sequence
<220> FEATURE:
<221> NAME/KEY: MISC_FEATURE
<222> LOCATION: (1)..(23)
<223> OTHER INFORMATION: Xaa is any amino acid

<400> SEQUENCE: 138

Xaa Leu Val Ala Lys Ile Xaa Xaa Xaa Pro Val Xaa Asn Xaa Xaa Xaa
1               5                   10                  15

Leu Xaa Xaa Xaa Xaa Leu Xaa Ile Ile
            20                  25

<210> SEQ ID NO 139
<211> LENGTH: 25
<212> TYPE: PRT
<213> ORGANISM: Artificial Sequence
<220> FEATURE:
<223> OTHER INFORMATION: Group P11 variant AMP sequence
<220> FEATURE:
<221> NAME/KEY: MISC_FEATURE
<222> LOCATION: (2)..(22)
<223> OTHER INFORMATION: Xaa is any amino acid

<400> SEQUENCE: 139

Ala Xaa Xaa Ala Xaa Ile Xaa Xaa Phe Xaa Xaa Phe Xaa Xaa Xaa Xaa
1               5                   10                  15

Xaa Cys Xaa Xaa Glu Xaa Glu Ile Ile
            20                  25

<210> SEQ ID NO 140
<211> LENGTH: 13
<212> TYPE: PRT
<213> ORGANISM: Artificial Sequence
<220> FEATURE:
<223> OTHER INFORMATION: Group P12 variant AMP sequence
<220> FEATURE:
<221> NAME/KEY: MISC_FEATURE
<222> LOCATION: (1)..(13)
<223> OTHER INFORMATION: Xaa is any amino acid

<400> SEQUENCE: 140

Xaa Xaa Gly Gln Val Xaa Xaa Xaa Lys Xaa Lys Xaa Xaa
1               5                   10

<210> SEQ ID NO 141
<211> LENGTH: 13
<212> TYPE: PRT
<213> ORGANISM: Artificial Sequence
<220> FEATURE:
<223> OTHER INFORMATION: Group P12 variant AMP sequence
<220> FEATURE:
<221> NAME/KEY: MISC_FEATURE
<222> LOCATION: (3)..(13)
<223> OTHER INFORMATION: Xaa is any amino acid

<400> SEQUENCE: 141

Ile Ala Xaa Xaa Xaa Ala Ala Ala Xaa Xaa Xaa Xaa Xaa
1               5                   10

<210> SEQ ID NO 142
<211> LENGTH: 13

```
<212> TYPE: PRT
<213> ORGANISM: Artificial Sequence
<220> FEATURE:
<223> OTHER INFORMATION: Group P12 variant AMP sequence
<220> FEATURE:
<221> NAME/KEY: MISC_FEATURE
<222> LOCATION: (1)..(10)
<223> OTHER INFORMATION: Xaa is any amino acid

<400> SEQUENCE: 142

Xaa Xaa Gly Xaa Xaa Xaa Xaa Xaa Lys Xaa Lys His Ile
 1               5                  10

<210> SEQ ID NO 143
<211> LENGTH: 13
<212> TYPE: PRT
<213> ORGANISM: Artificial Sequence
<220> FEATURE:
<223> OTHER INFORMATION: Group P12 variant AMP sequence
<220> FEATURE:
<221> NAME/KEY: MISC_FEATURE
<222> LOCATION: (2)..(8)
<223> OTHER INFORMATION: Xaa is any amino acid

<400> SEQUENCE: 143

Ile Xaa Xaa Gln Val Xaa Xaa Xaa Lys Gln Lys His Ile
 1               5                  10

<210> SEQ ID NO 144
<211> LENGTH: 13
<212> TYPE: PRT
<213> ORGANISM: Artificial Sequence
<220> FEATURE:
<223> OTHER INFORMATION: Group P12 variant AMP sequence
<220> FEATURE:
<221> NAME/KEY: MISC_FEATURE
<222> LOCATION: (1)..(11)
<223> OTHER INFORMATION: Xaa is any amino acid

<400> SEQUENCE: 144

Xaa Xaa Xaa Gln Val Xaa Xaa Xaa Xaa Gln Xaa His Ile
 1               5                  10

<210> SEQ ID NO 145
<211> LENGTH: 20
<212> TYPE: PRT
<213> ORGANISM: Artificial Sequence
<220> FEATURE:
<223> OTHER INFORMATION: Group P13 variant AMP sequence
<220> FEATURE:
<221> NAME/KEY: MISC_FEATURE
<222> LOCATION: (1)..(20)
<223> OTHER INFORMATION: Xaa is any amino acid

<400> SEQUENCE: 145

Xaa Xaa Arg Xaa Pro Xaa Xaa Xaa Xaa Lys Leu Trp Lys Xaa Xaa
 1               5                  10                  15

Leu Xaa Xaa Xaa
             20

<210> SEQ ID NO 146
<211> LENGTH: 20
<212> TYPE: PRT
<213> ORGANISM: Artificial Sequence
<220> FEATURE:
<223> OTHER INFORMATION: Group P13 variant AMP sequence
<220> FEATURE:
<221> NAME/KEY: MISC_FEATURE
<222> LOCATION: (3)..(18)
<223> OTHER INFORMATION: Xaa is any amino acid
```

<400> SEQUENCE: 146

Ile Gln Xaa Xaa Xaa Val Xaa Xaa Xaa Leu Xaa Xaa Xaa Xaa Leu Xaa
1               5                   10                  15

Xaa Xaa Ile Ile
            20

<210> SEQ ID NO 147
<211> LENGTH: 20
<212> TYPE: PRT
<213> ORGANISM: Artificial Sequence
<220> FEATURE:
<223> OTHER INFORMATION: Group P13 variant AMP sequence
<220> FEATURE:
<221> NAME/KEY: MISC_FEATURE
<222> LOCATION: (1)..(20)
<223> OTHER INFORMATION: Xaa is any amino acid

<400> SEQUENCE: 147

Xaa Xaa Xaa Leu Xaa Xaa Xaa Asn Met Xaa Xaa Xaa Trp Lys Xaa Xaa
1               5                   10                  15

Xaa Xaa Xaa Xaa
            20

<210> SEQ ID NO 148
<211> LENGTH: 20
<212> TYPE: PRT
<213> ORGANISM: Artificial Sequence
<220> FEATURE:
<223> OTHER INFORMATION: Group P13 variant AMP sequence
<220> FEATURE:
<221> NAME/KEY: MISC_FEATURE
<222> LOCATION: (1)..(20)
<223> OTHER INFORMATION: Xaa is any amino acid

<400> SEQUENCE: 148

Xaa Xaa Xaa Leu Pro Xaa Ile Asn Met Xaa Lys Leu Xaa Xaa Xaa Xaa
1               5                   10                  15

Leu Xaa Xaa Xaa
            20

<210> SEQ ID NO 149
<211> LENGTH: 21
<212> TYPE: PRT
<213> ORGANISM: Artificial Sequence
<220> FEATURE:
<223> OTHER INFORMATION: Group P14 variant AMP sequence
<220> FEATURE:
<221> NAME/KEY: MISC_FEATURE
<222> LOCATION: (5)..(17)
<223> OTHER INFORMATION: Xaa is any amino acid

<400> SEQUENCE: 149

Ile Gln Arg Leu Xaa Xaa Xaa Xaa Xaa Xaa Xaa Ser Leu Tyr Xaa Xaa
1               5                   10                  15

Xaa Cys Arg Thr Cys
            20

<210> SEQ ID NO 150
<211> LENGTH: 21
<212> TYPE: PRT
<213> ORGANISM: Artificial Sequence
<220> FEATURE:
<223> OTHER INFORMATION: Group P14 variant AMP sequence
<220> FEATURE:
<221> NAME/KEY: MISC_FEATURE
<222> LOCATION: (1)..(21)

<223> OTHER INFORMATION: Xaa is any amino acid

<400> SEQUENCE: 150

Xaa Xaa Xaa Leu Pro Val Xaa Val Xaa Leu Pro Ser Leu Tyr Xaa Xaa
1               5                   10                  15

Xaa Xaa Xaa Xaa Xaa
            20

<210> SEQ ID NO 151
<211> LENGTH: 21
<212> TYPE: PRT
<213> ORGANISM: Artificial Sequence
<220> FEATURE:
<223> OTHER INFORMATION: Group P14 variant AMP sequence
<220> FEATURE:
<221> NAME/KEY: MISC_FEATURE
<222> LOCATION: (4)..(21)
<223> OTHER INFORMATION: Xaa is any amino acid

<400> SEQUENCE: 151

Ile Gln Arg Xaa Xaa Xaa Ile Val Ile Xaa Xaa Xaa Xaa Xaa Cys Val
1               5                   10                  15

Ile Xaa Xaa Xaa Xaa
            20

<210> SEQ ID NO 152
<211> LENGTH: 21
<212> TYPE: PRT
<213> ORGANISM: Artificial Sequence
<220> FEATURE:
<223> OTHER INFORMATION: Group P14 variant AMP sequence
<220> FEATURE:
<221> NAME/KEY: MISC_FEATURE
<222> LOCATION: (1)..(17)
<223> OTHER INFORMATION: Xaa is any amino acid

<400> SEQUENCE: 152

Xaa Xaa Xaa Xaa Pro Val Xaa Xaa Xaa Xaa Pro Ser Leu Tyr Xaa Xaa
1               5                   10                  15

Xaa Cys Arg Thr Cys
            20

<210> SEQ ID NO 153
<211> LENGTH: 21
<212> TYPE: PRT
<213> ORGANISM: Artificial Sequence
<220> FEATURE:
<223> OTHER INFORMATION: Group P14 variant AMP sequence
<220> FEATURE:
<221> NAME/KEY: MISC_FEATURE
<222> LOCATION: (5)..(20)
<223> OTHER INFORMATION: Xaa is any amino acid

<400> SEQUENCE: 153

Ile Gln Arg Leu Xaa Val Ile Xaa Ile Leu Xaa Xaa Xaa Xaa Cys Xaa
1               5                   10                  15

Xaa Cys Xaa Xaa Cys
            20

<210> SEQ ID NO 154
<211> LENGTH: 21
<212> TYPE: PRT
<213> ORGANISM: Artificial Sequence
<220> FEATURE:
<223> OTHER INFORMATION: Group P14 variant AMP sequence
<220> FEATURE:
<221> NAME/KEY: MISC_FEATURE

```
<222> LOCATION: (1)..(21)
<223> OTHER INFORMATION: Xaa is any amino acid

<400> SEQUENCE: 154

Xaa Xaa Xaa Leu Pro Xaa Xaa Xaa Xaa Xaa Pro Xaa Xaa Xaa Xaa Val
1               5                   10                  15

Ile Xaa Xaa Thr Xaa
            20

<210> SEQ ID NO 155
<211> LENGTH: 21
<212> TYPE: PRT
<213> ORGANISM: Artificial Sequence
<220> FEATURE:
<223> OTHER INFORMATION: Group P14 variant AMP sequence
<220> FEATURE:
<221> NAME/KEY: MISC_FEATURE
<222> LOCATION: (1)..(11)
<223> OTHER INFORMATION: Xaa is any amino acid

<400> SEQUENCE: 155

Xaa Xaa Xaa Leu Xaa Val Ile Val Ile Leu Xaa Ser Leu Tyr Cys Val
1               5                   10                  15

Ile Cys Arg Thr Cys
            20

<210> SEQ ID NO 156
<211> LENGTH: 35
<212> TYPE: PRT
<213> ORGANISM: Artificial Sequence
<220> FEATURE:
<223> OTHER INFORMATION: Group P15 variant AMP sequence
<220> FEATURE:
<221> NAME/KEY: MISC_FEATURE
<222> LOCATION: (2)..(35)
<223> OTHER INFORMATION: Xaa is any amino acid

<400> SEQUENCE: 156

Leu Xaa Xaa Pro Xaa Pro Xaa Tyr Xaa Phe Xaa Xaa Gly Ile Gly Xaa
1               5                   10                  15

Xaa Xaa Xaa Trp Xaa Xaa Xaa Trp Leu Asn Ala Gln Gln Met Xaa Xaa
            20                  25                  30

Xaa Xaa Xaa
        35

<210> SEQ ID NO 157
<211> LENGTH: 35
<212> TYPE: PRT
<213> ORGANISM: Artificial Sequence
<220> FEATURE:
<223> OTHER INFORMATION: Group P15 variant AMP sequence
<220> FEATURE:
<221> NAME/KEY: MISC_FEATURE
<222> LOCATION: (1)..(35)
<223> OTHER INFORMATION: Xaa is any amino acid

<400> SEQUENCE: 157

Xaa Xaa Cys Pro Thr Pro Xaa Xaa Xaa Phe Xaa Xaa Xaa Xaa Xaa Asn
1               5                   10                  15

His Leu Xaa Xaa Xaa Ile Ile Trp Leu Xaa Xaa Xaa Xaa Met Xaa Xaa
            20                  25                  30

Xaa Xaa Xaa
        35

<210> SEQ ID NO 158
```

```
<211> LENGTH: 35
<212> TYPE: PRT
<213> ORGANISM: Artificial Sequence
<220> FEATURE:
<223> OTHER INFORMATION: Group P15 variant AMP sequence
<220> FEATURE:
<221> NAME/KEY: MISC_FEATURE
<222> LOCATION: (4)..(30)
<223> OTHER INFORMATION: Xaa is any amino acid

<400> SEQUENCE: 158

Leu Arg Cys Xaa Xaa Xaa Xaa Xaa Xaa Glu Asn Gly Xaa Xaa Xaa
1               5                   10                  15

Xaa Xaa Met Trp Asn Xaa Xaa Xaa Xaa Xaa Xaa Xaa Xaa Ser Tyr
            20                  25                  30

Lys Asn Lys
        35

<210> SEQ ID NO 159
<211> LENGTH: 35
<212> TYPE: PRT
<213> ORGANISM: Artificial Sequence
<220> FEATURE:
<223> OTHER INFORMATION: Group P15 variant AMP sequence
<220> FEATURE:
<221> NAME/KEY: MISC_FEATURE
<222> LOCATION: (1)..(34)
<223> OTHER INFORMATION: Xaa is any amino acid

<400> SEQUENCE: 159

Xaa Xaa Xaa Xaa Thr Xaa His Tyr Asn Xaa Glu Asn Gly Ile Gly Asn
1               5                   10                  15

His Leu Met Xaa Asn Xaa Xaa Xaa Xaa Asn Xaa Gln Xaa Xaa Xaa Xaa
            20                  25                  30

Lys Xaa Lys
        35

<210> SEQ ID NO 160
<211> LENGTH: 35
<212> TYPE: PRT
<213> ORGANISM: Artificial Sequence
<220> FEATURE:
<223> OTHER INFORMATION: Group P15 variant AMP sequence
<220> FEATURE:
<221> NAME/KEY: MISC_FEATURE
<222> LOCATION: (2)..(35)
<223> OTHER INFORMATION: Xaa is any amino acid

<400> SEQUENCE: 160

Leu Xaa Cys Xaa Xaa Xaa His Xaa Asn Xaa Xaa Xaa Xaa Xaa Gly Asn
1               5                   10                  15

His Xaa Xaa Trp Xaa Xaa Xaa Trp Leu Xaa Xaa Xaa Xaa Met Ser Xaa
            20                  25                  30

Xaa Asn Xaa
        35

<210> SEQ ID NO 161
<211> LENGTH: 35
<212> TYPE: PRT
<213> ORGANISM: Artificial Sequence
<220> FEATURE:
<223> OTHER INFORMATION: Group P15 variant AMP sequence
<220> FEATURE:
<221> NAME/KEY: MISC_FEATURE
<222> LOCATION: (1)..(35)
<223> OTHER INFORMATION: Xaa is any amino acid
```

<400> SEQUENCE: 161

Xaa Arg Xaa Pro Xaa Pro His Xaa Xaa Phe Xaa Xaa Xaa Xaa Xaa
1               5                   10                  15

Xaa Xaa Xaa Xaa Xaa Ile Ile Xaa Xaa Xaa Ala Xaa Gln Xaa Ser Tyr
                20                  25                  30

Xaa Xaa Xaa
        35

<210> SEQ ID NO 162
<211> LENGTH: 25
<212> TYPE: PRT
<213> ORGANISM: Artificial Sequence
<220> FEATURE:
<223> OTHER INFORMATION: Group P16 variant AMP sequence
<220> FEATURE:
<221> NAME/KEY: MISC_FEATURE
<222> LOCATION: (4)..(25)
<223> OTHER INFORMATION: Xaa is any amino acid

<400> SEQUENCE: 162

Ser Asn Arg Xaa Xaa Xaa Met Xaa Xaa Xaa Xaa Gly Leu Xaa Gly Pro
1               5                   10                  15

Xaa Xaa Ile Met Xaa Xaa Xaa Xaa Xaa
            20                  25

<210> SEQ ID NO 163
<211> LENGTH: 25
<212> TYPE: PRT
<213> ORGANISM: Artificial Sequence
<220> FEATURE:
<223> OTHER INFORMATION: Group P16 variant AMP sequence
<220> FEATURE:
<221> NAME/KEY: MISC_FEATURE
<222> LOCATION: (1)..(25)
<223> OTHER INFORMATION: Xaa is any amino acid

<400> SEQUENCE: 163

Xaa Xaa Xaa Xaa Phe Phe Met Xaa Xaa Xaa Xaa Xaa Cys Xaa Xaa
1               5                   10                  15

Phe Gly Xaa Xaa Xaa Xaa Lys Xaa Xaa
            20                  25

<210> SEQ ID NO 164
<211> LENGTH: 25
<212> TYPE: PRT
<213> ORGANISM: Artificial Sequence
<220> FEATURE:
<223> OTHER INFORMATION: Group P16 variant AMP sequence
<220> FEATURE:
<221> NAME/KEY: MISC_FEATURE
<222> LOCATION: (5)..(21)
<223> OTHER INFORMATION: Xaa is any amino acid

<400> SEQUENCE: 164

Ser Asn Arg Asp Xaa Xaa Xaa Xaa Xaa Ile Phe Gly Leu Xaa Gly Pro
1               5                   10                  15

Xaa Xaa Ile Met Xaa Arg Lys Arg Arg
            20                  25

<210> SEQ ID NO 165
<211> LENGTH: 25
<212> TYPE: PRT
<213> ORGANISM: Artificial Sequence
<220> FEATURE:
<223> OTHER INFORMATION: Group P16 variant AMP sequence
<220> FEATURE:

```
<221> NAME/KEY: MISC_FEATURE
<222> LOCATION: (2)..(25)
<223> OTHER INFORMATION: Xaa is any amino acid

<400> SEQUENCE: 165

Ser Xaa Xaa Xaa Xaa Xaa Val Asn Xaa Xaa Xaa Xaa Cys Xaa Xaa
1               5                   10                  15

Phe Gly Xaa Xaa Glu Xaa Xaa Xaa Xaa
            20                  25

<210> SEQ ID NO 166
<211> LENGTH: 25
<212> TYPE: PRT
<213> ORGANISM: Artificial Sequence
<220> FEATURE:
<223> OTHER INFORMATION: Group P16 variant AMP sequence
<220> FEATURE:
<221> NAME/KEY: MISC_FEATURE
<222> LOCATION: (1)..(23)
<223> OTHER INFORMATION: Xaa is any amino acid

<400> SEQUENCE: 166

Xaa Xaa Xaa Xaa Xaa Xaa Xaa Val Asn Ile Phe Xaa Xaa Xaa Xaa Pro
1               5                   10                  15

Xaa Xaa Xaa Xaa Xaa Arg Xaa Arg Arg
            20                  25

<210> SEQ ID NO 167
<211> LENGTH: 71
<212> TYPE: PRT
<213> ORGANISM: Artificial Sequence
<220> FEATURE:
<223> OTHER INFORMATION: antimicrobial peptide

<400> SEQUENCE: 167

Lys Ser Lys Leu Ser Leu Lys Lys Gln Gly Thr Ile His Leu Asp Ala
1               5                   10                  15

Gln Ser Ser Cys Asp Val Met His Phe Pro Lys Cys Asp Leu Ala Pro
            20                  25                  30

Asn Val Gln Arg Gln Ala Trp Leu Phe Lys Val Ala Ser Lys Glu Ala
        35                  40                  45

Lys Glu Leu Arg Tyr Tyr Leu Leu Asn Pro Tyr Leu Asp Val Ser Ala
    50                  55                  60

Arg Asn Val Gly Ser Lys Val
65                  70

<210> SEQ ID NO 168
<211> LENGTH: 47
<212> TYPE: PRT
<213> ORGANISM: Artificial Sequence
<220> FEATURE:
<223> OTHER INFORMATION: Antimicribial peptide

<400> SEQUENCE: 168

Lys Ala Gly Glu Gly Glu Arg Gly Glu Arg Glu Val Leu Asn His Gln
1               5                   10                  15

Lys Thr Ile Leu Glu Pro Ser Ser Cys Pro Leu Ile Ser Pro His Ser
            20                  25                  30

Thr Gly Leu Gly His Arg Pro Ser Leu Phe Arg Leu Thr Leu Ala
        35                  40                  45

<210> SEQ ID NO 169
<211> LENGTH: 42
```

<212> TYPE: PRT
<213> ORGANISM: Artificial Sequence
<220> FEATURE:
<223> OTHER INFORMATION: Antimircrobial Peptide

<400> SEQUENCE: 169

Leu Lys Gly Ile Lys Asn Ala Ala Gln Leu Leu Arg Phe Pro Pro Asn
1               5                   10                  15

Cys Lys Leu Cys Ser Cys Thr Val Phe Val His Lys Asp His Cys Val
            20                  25                  30

Val Gln Glu Ala Ser Gly Val Phe Arg Phe
        35                  40

<210> SEQ ID NO 170
<211> LENGTH: 47
<212> TYPE: PRT
<213> ORGANISM: Artificial Sequence
<220> FEATURE:
<223> OTHER INFORMATION: Antimicrobial Peptide

<400> SEQUENCE: 170

Asn Ala Ala Arg Asp His Ser Ala Thr Arg Cys Lys Gln Arg Ser Ala
1               5                   10                  15

Arg Leu Gln Ile Ala Ala Gln Asp Tyr Arg Ser Gln Ser Ala Arg
            20                  25                  30

Leu Gln Ile Ala Thr Gln Arg Lys Ile Thr Asp Arg Asn Thr Ala
        35                  40                  45

<210> SEQ ID NO 171
<211> LENGTH: 15
<212> TYPE: PRT
<213> ORGANISM: Artificial Sequence
<220> FEATURE:
<223> OTHER INFORMATION: Antimicrobial Peptide

<400> SEQUENCE: 171

Leu Lys Pro Ser Asn Ile Gln Val Lys Leu Gln Tyr Ile Tyr Trp
1               5                   10                  15

<210> SEQ ID NO 172
<211> LENGTH: 122
<212> TYPE: PRT
<213> ORGANISM: Artificial Sequence
<220> FEATURE:
<223> OTHER INFORMATION: Antimicrobial peptide precursor

<400> SEQUENCE: 172

Met Asn Cys Gly Ser Phe Pro Cys Asp Ala Cys Asp Val Cys Glu Tyr
1               5                   10                  15

Val Asp Ala Lys Thr Lys Leu Lys Leu Pro Asn Gly Arg Trp His Ser
            20                  25                  30

Ile Gln Phe Arg Val Thr Cys Gln Thr Pro Gly Val Ile Tyr Leu Ala
        35                  40                  45

Gln Cys Leu Cys Gly Gly Phe Tyr Ile Gly Lys Thr Lys Arg Gln Phe
    50                  55                  60

Phe Lys Arg Ile Arg Asp His Ile Lys Pro Ile Arg Lys Asn Lys Met
65                  70                  75                  80

Asp Thr Ala Ile Ser Arg His Val Gly Ile His His Asn Phe Asn Pro
                85                  90                  95

Gln Phe Ile Lys Phe Ser Ala Leu Glu His Ile Pro Gln Thr Leu Ala
            100                 105                 110

Val Ala Ala Leu Ile Ala Ser Cys Tyr Asn
        115                 120

<210> SEQ ID NO 173
<211> LENGTH: 29
<212> TYPE: PRT
<213> ORGANISM: Artificial Sequence
<220> FEATURE:
<223> OTHER INFORMATION: Antimicrobial peptide precursor

<400> SEQUENCE: 173

Met Glu Glu Ile Val Phe Pro Leu Gln His Pro Phe His Leu Asp Cys
1               5                   10                  15

Leu Phe Phe Leu Leu Arg His Leu Ser Trp Glu Lys Thr
            20                  25

<210> SEQ ID NO 174
<211> LENGTH: 43
<212> TYPE: PRT
<213> ORGANISM: Artificial Sequence
<220> FEATURE:
<223> OTHER INFORMATION: Antimicrobial peptide precursor

<400> SEQUENCE: 174

Met Ser Ile Lys Lys Glu Glu Met Ile Gln Val Lys Gly Met Leu
1               5                   10                  15

Lys Trp Lys Asn Asp Phe Tyr Gln Leu Leu Glu Arg Phe Ser Val Leu
            20                  25                  30

Cys Leu Glu Lys Asn Pro Glu Met Leu Lys Leu
        35                  40

<210> SEQ ID NO 175
<211> LENGTH: 35
<212> TYPE: PRT
<213> ORGANISM: Artificial Sequence
<220> FEATURE:
<223> OTHER INFORMATION: Antimicrobial peptide precursor

<400> SEQUENCE: 175

Met Ile Gln Val Lys Gly Met Leu Lys Trp Lys Asn Asp Phe Tyr Gln
1               5                   10                  15

Leu Leu Glu Arg Phe Ser Val Leu Cys Leu Glu Lys Asn Pro Glu Met
            20                  25                  30

Leu Lys Leu
        35

<210> SEQ ID NO 176
<211> LENGTH: 27
<212> TYPE: PRT
<213> ORGANISM: Artificial Sequence
<220> FEATURE:
<223> OTHER INFORMATION: Antimicrobial peptide precursor

<400> SEQUENCE: 176

Met Pro Lys Lys Lys Glu Glu Thr Ile Gln Met Lys Gly Met Leu Lys
1               5                   10                  15

Trp Lys Asn Asp Phe Phe Gln Leu Leu His Ala
            20                  25

<210> SEQ ID NO 177
<211> LENGTH: 41
<212> TYPE: PRT
<213> ORGANISM: Artificial Sequence
<220> FEATURE:

```
<223> OTHER INFORMATION: Antimicrobial peptide precursor

<400> SEQUENCE: 177

Met Ser Gly Ser Arg Ile Gly Leu Pro Leu Ala Leu Phe Pro Val Thr
1               5                   10                  15

Phe Val Lys Ile Ser Leu Phe Ile Leu Leu Ser Ser Ser Ser Ala
            20                  25                  30

Phe Leu Leu Gly Glu His Ser Tyr Cys
        35                  40

<210> SEQ ID NO 178
<211> LENGTH: 85
<212> TYPE: PRT
<213> ORGANISM: Artificial Sequence
<220> FEATURE:
<223> OTHER INFORMATION: Antimicrobial peptide precursor

<400> SEQUENCE: 178

Met Ser Ser Pro Arg Arg Asp Ala Asn Glu Glu Arg Arg Asp Asp
1               5                   10                  15

Pro Asp Glu Arg Asp Val Glu Val Glu Lys Arg Leu Leu Pro Val Thr
            20                  25                  30

Thr Ser Glu Asn Val Leu Val His Arg Gly Gly Gln Lys Ala Gly Met
            35                  40                  45

Asp His Arg Glu Val Thr Gln Gly Trp Arg Glu Asp Leu Gly His Gln
        50                  55                  60

Glu Glu Leu Ser Leu Asn Leu Gln Glu Asn Asn Gly Gly His Pro Gln
65                  70                  75                  80

Phe Met Pro Phe Gln
                85
```